United States Patent [19]
Unger

[11] Patent Number: 5,922,304
[45] Date of Patent: Jul. 13, 1999

[54] GASEOUS PRECURSOR FILLED MICROSPHERES AS MAGNETIC RESONANCE IMAGING CONTRAST AGENTS

[75] Inventor: Evan C. Unger, Tucson, Ariz.

[73] Assignee: Imarx Pharmaceutical Corp., Tucson, Ark.

[21] Appl. No.: 08/401,974

[22] Filed: Mar. 9, 1995

Related U.S. Application Data

[63] Continuation-in-part of application No. 08/212,553, Mar. 11, 1994., and a continuation-in-part of application No. 08/076,250, Jun. 11, 1993., which is a continuation-in-part of application No. 07/716,899, Jun. 18, 1991., and a continuation-in-part of application No. 07/717,084, Jun. 18, 1991., Pat. No. 5,228,446, said application No. 07/716,899, is a continuation-in-part of application No. 07/569,828, Aug. 20, 1991., Pat. No. 5,088,499, which is a continuation-in-part of application No. 07/455,707, Dec. 22, 1989., abandoned, said application No. 07/717,084, is a continuation-in-part of application No. 07/569,828, Aug. 20, 1990., Pat. No. 5,088,499, which is a continuation-in-part of application No. 07/455,707, Dec. 22, 1989., abandoned, and a continuation-in-part of application No. 08/076,239, Jun. 11, 1993., Pat. No. 5,469,854, which is a continuation-in-part of application No. 07/716,899, Jun. 18, 1991., abandoned, and a continuation-in-part of application No. 07/717,084, Jun. 18, 1991., Pat. No. 5,228,446, said application No. 07/716,899, is a continuation-in-part of application No. 07/569,828, Aug. 20, 1990., Pat. No. 5,088,499, which is a continuation-in-part of application No. 07/455,707, Dec. 22, 1989., abandoned, said application No. 07/717,084, is a continuation-in-part of application No. 07/569,828, Aug. 20, 1990., Pat. No. 5,088,499, which is a continuation-in-part of application No. 07/455,707, Dec. 22, 1989., abandoned, and a continuation-in-part of application No. 08/307,305, Sep. 16, 1994., Pat. No. 5,773,024, which is a continuation-in-part of application No. 08/212,553, Mar. 11, 1994., abandoned, and a continuation-in-part of application No. 08/159,687, Nov. 30, 1993., Pat. No. 5,585,112, which is a continuation-in-part of application No. 08/160,232, Nov. 30, 1993., Pat. No. 5,542,935, said application No. 08/159,687, is a continuation-in-part of application No. 08/159,674, Nov. 30, 1993., abandoned, and a continuation-in-part of application No. 08/159,687, Nov. 30, 1993., Pat. No. 5,585,112, which is a continuation-in-part of application No. 08/160,232, Nov. 30, 1993., Pat. No. 5,542,935, and a continuation-in-part of application No. 08/159,674, Nov. 30, 1993., abandoned, and a continuation-in-part of application No. 08/160,232, Nov. 30, 1993., Pat. No. 5,542,935, which is a continuation-in-part of application No. 08/159,687, Nov. 30, 1993., Pat. No. 5,585,112, and a continuation-in-part of application No. 08/159,674, Nov. 30, 1993., abandoned

[51] Int. Cl.$^6$ .......................... A61B 5/055; A61K 49/04
[52] U.S. Cl. .................. 424/9.3; 424/9.321; 424/9.32; 424/9.37; 424/9.52
[58] Field of Search ............................ 424/9.321, 9.32, 424/9.3, 9.52, 9.51, 450, 498, 9.37; 128/662.02, 653.4; 600/458

[56] References Cited

U.S. PATENT DOCUMENTS

| | | | |
|---|---|---|---|
| 3,015,128 | 1/1962 | Sommerville et al. | 18/2.6 |
| 3,293,114 | 12/1966 | Kenaga et al. | 162/168 |

(List continued on next page.)

FOREIGN PATENT DOCUMENTS

| | | |
|---|---|---|
| 641363 | 3/1990 | Australia . |
| B-30351/89 | 3/1993 | Australia . |

(List continued on next page.)

OTHER PUBLICATIONS

Sigel, H., ed., *Metal Ions in Biological Systems: Antibiotics and Their Complexes*, vol. 19 (Marcel Dekker, N.Y.),(1985).

(List continued on next page.)

*Primary Examiner*—Jose'G. Dees
*Assistant Examiner*—Michael G. Hartley
*Attorney, Agent, or Firm*—Woodcock Washburn Kurtz Mackiewicz & Norris LLP

[57] ABSTRACT

Novel gas filled microspheres useful as magnetic resonance imaging (MRI) contrast agents are provided.

43 Claims, 11 Drawing Sheets

U.S. PATENT DOCUMENTS

| | | | |
|---|---|---|---|
| 3,479,811 | 11/1969 | Walters | 57/153 |
| 3,488,714 | 1/1970 | Walters et al. | 161/161 |
| 3,532,500 | 10/1970 | Priest et al. | 96/91 |
| 3,594,326 | 7/1971 | Himmel et al. | 252/316 |
| 3,615,972 | 10/1971 | Morehouse et al. | 156/79 |
| 3,650,831 | 3/1972 | Jungermann et al. | 134/27 |
| 3,732,172 | 5/1973 | Herbig et al. | 252/316 |
| 3,873,564 | 3/1975 | Schneider et al. | 260/309.6 |
| 3,945,956 | 3/1976 | Gerner | 260/2.5 B |
| 3,960,583 | 6/1976 | Netting et al. | 106/122 |
| 3,968,203 | 7/1976 | Spitzer et al. | 424/47 |
| 4,027,007 | 5/1977 | Messina | 424/46 |
| 4,089,801 | 5/1978 | Schneider | 252/316 |
| 4,108,806 | 8/1978 | Cohrs et al. | 521/54 |
| 4,138,383 | 2/1979 | Rembaum et al. | 260/29.7 H |
| 4,162,282 | 7/1979 | Fulwyler et al. | 264/9 |
| 4,179,546 | 12/1979 | Garner et al. | 521/56 |
| 4,192,859 | 3/1980 | Mackaness et al | 424/5 |
| 4,224,179 | 9/1980 | Schneider | 252/316 |
| 4,229,360 | 10/1980 | Schneider et al. | 260/403 |
| 4,265,251 | 5/1981 | Tickner | 128/660 |
| 4,276,885 | 7/1981 | Tickner et al. | 128/660 |
| 4,310,505 | 1/1982 | Baldeschwieler et al. | 424/1 |
| 4,310,506 | 1/1982 | Baldeschwieler et al. | 424/1 |
| 4,315,514 | 2/1982 | Drewes et al. | 128/653 |
| 4,331,654 | 5/1982 | Morris | 424/38 |
| 4,342,826 | 8/1982 | Cole | 435/7 |
| 4,344,929 | 8/1982 | Bonsen et al. | 424/15 |
| 4,420,442 | 12/1983 | Sands | 264/13 |
| 4,421,562 | 12/1983 | Sands et al. | 106/75 |
| 4,426,330 | 1/1984 | Sears | 260/403 |
| 4,428,924 | 1/1984 | Millington | 424/4 |
| 4,442,843 | 4/1984 | Rasor et al. | 128/660 |
| 4,466,442 | 8/1984 | Hilmann et al. | 128/653 |
| 4,533,254 | 8/1985 | Cook et al. | 366/176 |
| 4,534,899 | 8/1985 | Sears | 260/403 |
| 4,540,629 | 9/1985 | Sands et al. | 428/402 |
| 4,544,545 | 10/1985 | Ryan et al. | 424/1.1 |
| 4,549,892 | 10/1985 | Baker et al. | 65/21.4 |
| 4,569,836 | 2/1986 | Gordon | 424/1.1 |
| 4,572,203 | 2/1986 | Feinstein | 128/661 |
| 4,586,512 | 5/1986 | Do-huu et al. | 128/660 |
| 4,603,044 | 7/1986 | Geho et al. | 424/9 |
| 4,615,879 | 10/1986 | Runge et al. | 424/9 |
| 4,620,546 | 11/1986 | Aida et al. | 128/660 |
| 4,646,756 | 3/1987 | Watmough et al. | 128/804 |
| 4,657,756 | 4/1987 | Rasor et al. | 424/9 |
| 4,658,828 | 4/1987 | Dory | 128/660 |
| 4,675,310 | 6/1987 | Chapman et al. | 514/6 |
| 4,681,119 | 7/1987 | Rasor et al. | 128/660 |
| 4,684,479 | 8/1987 | D'Arrigo | 252/307 |
| 4,689,986 | 9/1987 | Carson et al. | 73/19 |
| 4,718,433 | 1/1988 | Feinstein | 128/660 |
| 4,728,575 | 3/1988 | Gamble et al. | 428/402.2 |
| 4,728,578 | 3/1988 | Higgins et al. | 428/46 |
| 4,731,239 | 3/1988 | Gordon | 424/9 |
| 4,737,323 | 4/1988 | Martin et al. | 264/4.3 |
| 4,774,958 | 10/1988 | Feinstein | 128/660.01 |
| 4,775,522 | 10/1988 | Clark, Jr. | 424/9 |
| 4,776,991 | 10/1988 | Farmer et al. | 264/4.3 |
| 4,781,871 | 11/1988 | West, III et al. | 264/4.3 |
| 4,789,501 | 12/1988 | Day et al. | 252/645 |
| 4,790,891 | 12/1988 | Halliday et al. | 149/2 |
| 4,822,534 | 4/1989 | Lencki et al. | 264/4.3 |
| 4,830,858 | 5/1989 | Payne et al. | 424/450 |
| 4,844,882 | 7/1989 | Widder et al. | 424/9 |
| 4,863,717 | 9/1989 | Keana | 424/9 |
| 4,865,836 | 9/1989 | Long, Jr. | 424/5 |
| 4,877,561 | 10/1989 | Iga et al. | 264/4.3 |
| 4,893,624 | 1/1990 | Lele | 128/399 |
| 4,895,719 | 1/1990 | Radhakrishnan | 424/45 |
| 4,898,734 | 2/1990 | Mathiowitz et al. | 424/426 |
| 4,900,540 | 2/1990 | Ryan et al. | 424/9 |
| 4,921,706 | 5/1990 | Roberts et al. | 424/450 |
| 4,927,623 | 5/1990 | Long, Jr. | 424/5 |
| 4,933,121 | 6/1990 | Law et al. | 264/4.3 |
| 4,938,947 | 7/1990 | Nicolau et al. | 424/1.1 |
| 4,957,656 | 9/1990 | Cerny et al. | 252/311 |
| 4,981,692 | 1/1991 | Popescu et al. | 424/422 |
| 4,985,550 | 1/1991 | Charpiot et al. | 536/18.4 |
| 4,987,154 | 1/1991 | Long, Jr. | 514/772 |
| 4,993,415 | 2/1991 | Long | 128/653 A |
| 4,996,041 | 2/1991 | Arai et al. | 424/9 |
| 5,000,960 | 3/1991 | Wallach | 424/450 |
| 5,004,611 | 4/1991 | Leigh | 424/450 |
| 5,008,050 | 4/1991 | Cullis et al. | 264/4.3 |
| 5,013,556 | 5/1991 | Woodle et al. | 424/450 |
| 5,019,370 | 5/1991 | Jay et al. | 424/4 |
| 5,036,003 | 7/1991 | Olander et al. | 435/70.1 |
| 5,045,304 | 9/1991 | Schneider et al. | 424/9 |
| 5,049,388 | 9/1991 | Knight et al. | 424/450 |
| 5,078,994 | 1/1992 | Nair et al. | 424/501 |
| 5,088,499 | 2/1992 | Unger | 128/662.2 |
| 5,114,703 | 5/1992 | Wolf et al. | 424/5 |
| 5,123,414 | 6/1992 | Unger | 128/654 |
| 5,135,000 | 8/1992 | Akselrod et al. | 128/662.02 |
| 5,137,928 | 8/1992 | Erbel et al. | 521/56 |
| 5,141,738 | 8/1992 | Rasor et al. | 424/2 |
| 5,147,631 | 9/1992 | Glajch et al. | 424/9 |
| 5,149,319 | 9/1992 | Unger | 604/22 |
| 5,171,755 | 12/1992 | Kaufman | 514/759 |
| 5,186,992 | 2/1993 | Shell et al. | 128/654 |
| 5,190,982 | 3/1993 | Erbel et al. | 541/56 |
| 5,192,549 | 3/1993 | Barenolz et al. | 424/450 |
| 5,194,266 | 3/1993 | Abra et al. | 424/450 |
| 5,195,520 | 3/1993 | Schlief et al. | 128/660.02 |
| 5,196,183 | 3/1993 | Yudelson et al. | 424/9 |
| 5,198,255 | 3/1993 | Meybeck et al. | 424/450 |
| 5,205,287 | 4/1993 | Erbel et al. | 128/632 |
| 5,205,290 | 4/1993 | Unger | 128/653.4 |
| 5,209,720 | 5/1993 | Unger | 604/22 |
| 5,213,804 | 5/1993 | Martin et al. | 424/450 |
| 5,215,680 | 6/1993 | D'Arrigo | 252/307 |
| 5,219,538 | 6/1993 | Henderson et al. | 428/402.2 |
| 5,228,446 | 7/1993 | Unger et al. | 128/662.02 |
| 5,230,882 | 7/1993 | Unger | 424/9 |
| 5,247,935 | 9/1993 | Cline et al. | 128/653.2 |
| 5,271,928 | 12/1993 | Schneider et al. | 424/9 |
| 5,281,408 | 1/1994 | Unger | 424/4 |
| 5,305,757 | 4/1994 | Unger et al. | 128/662.02 |
| 5,310,540 | 5/1994 | Giddey et al. | 424/9 |
| 5,315,997 | 5/1994 | Widder et al. | 128/653.3 |
| 5,315,998 | 5/1994 | Tachibana et al. | 128/660.01 |
| 5,316,771 | 5/1994 | Barenholz et al. | 424/450 |
| 5,334,381 | 8/1994 | Unger | 424/9 |
| 5,344,930 | 9/1994 | Riess et al. | 544/84 |
| 5,350,571 | 9/1994 | Kaufmann et al. | 424/9 |
| 5,352,435 | 10/1994 | Unger | 424/9 |
| 5,354,549 | 10/1994 | Klaveness et al. | 424/3 |
| 5,358,702 | 10/1994 | Unger | 424/9 |
| 5,362,478 | 11/1994 | Desai et al. | 424/9 |
| 5,380,519 | 1/1995 | Schneider et al. | 424/9 |
| 5,393,524 | 2/1995 | Quay | 424/9 |
| 5,409,688 | 4/1995 | Quay | 242/9 |
| 5,410,516 | 4/1995 | Uhlendorf et al. | 367/7 |
| 5,413,774 | 5/1995 | Schneider et al. | 424/9.51 |
| 5,425,366 | 6/1995 | Reinhardt et al. | 128/662.02 |
| 5,433,204 | 7/1995 | Olson | 128/661.08 |
| 5,445,813 | 8/1995 | Schneider et al. | 424/9.51 |
| 5,456,900 | 10/1995 | Unger | 424/9.4 |
| 5,469,854 | 11/1995 | Unger et al. | 128/662.02 |
| 5,470,582 | 11/1995 | Supersaxo et al. | 424/489 |

| | | | |
|---|---|---|---|
| 5,487,390 | 1/1996 | Cohen et al. | 128/662.02 |
| 5,496,535 | 3/1996 | Kirkland | 424/9.37 |
| 5,498,421 | 3/1996 | Grinstaff et al. | 424/450 |
| 5,501,863 | 3/1996 | Rössling et al. | 424/489 |
| 5,502,094 | 3/1996 | Moore et al. | 524/145 |
| 5,505,932 | 4/1996 | Grinstaff et al. | 424/9.3 |
| 5,527,521 | 6/1996 | Unger | 424/93 |
| 5,529,766 | 6/1996 | Klaveness et al. | 424/9.52 |
| 5,531,980 | 7/1996 | Schneider et al. | 424/9.52 |
| 5,536,489 | 7/1996 | Lohrmann et al. | 424/9.52 |
| 5,536,490 | 7/1996 | Klaveness et al. | 424/9.52 |
| 5,540,909 | 7/1996 | Schutt | 424/9.52 |
| 5,542,935 | 8/1996 | Unger et al. | 604/190 |
| 5,547,656 | 8/1996 | Unger | 424/9.4 |
| 5,552,133 | 9/1996 | Lambert et al. | 424/9.52 |
| 5,556,610 | 9/1996 | Yan et al. | 424/9.52 |
| 5,558,092 | 9/1996 | Unger et al. | 128/660.03 |
| 5,558,094 | 9/1996 | Quay | 128/662.02 |
| 5,558,853 | 9/1996 | Quay | 424/9.5 |
| 5,558,854 | 9/1996 | Quay | 424/9.52 |
| 5,558,855 | 9/1996 | Quay | 424/9.5 |
| 5,558,856 | 9/1996 | Klaveness et al. | 424/9.37 |
| 5,560,364 | 10/1996 | Porter | 128/66.202 |
| 5,562,893 | 10/1996 | Lohrmann | 424/9.52 |
| 5,567,413 | 10/1996 | Klaveness et al. | 424/9.51 |
| 5,567,414 | 10/1996 | Schneider et al. | 424/9.52 |
| 5,567,765 | 10/1996 | Moore et al. | 524/801 |
| 5,569,449 | 10/1996 | Klaveness et al. | 424/9.51 |
| 5,573,751 | 11/1996 | Quay | 424/9.52 |
| 5,578,292 | 11/1996 | Schneider et al. | 424/9.51 |
| 5,585,112 | 12/1996 | Unger et al. | 424/450 |
| 5,595,723 | 1/1997 | Quay | 424/9.5 |
| 5,605,673 | 2/1997 | Schutt et al. | 424/9.51 |
| 5,606,973 | 3/1997 | Lambert et al. | 128/662.02 |
| 5,614,169 | 3/1997 | Klaveness et al. | 424/9.52 |
| 5,620,689 | 4/1997 | Allen et al. | 424/178.1 |
| 5,626,833 | 5/1997 | Schutt et al. | 424/9.52 |
| 5,639,443 | 6/1997 | Schutt et al. | 424/9.52 |
| 5,643,553 | 7/1997 | Schneider et al. | 424/9.52 |
| 5,672,585 | 9/1997 | Pierschbacher et al. | 514/11 |
| 5,676,928 | 10/1997 | Klaveness et al. | 424/9.32 |
| 5,686,060 | 11/1997 | Schneider et al. | 424/9.52 |
| 5,707,606 | 1/1998 | Quay | 424/9.52 |
| 5,707,607 | 1/1998 | Quay | 424/9.52 |
| B1 4,229,360 | 11/1991 | Schneider et al. | 260/403 |

FOREIGN PATENT DOCUMENTS

| | | |
|---|---|---|
| 0 007 752 B1 | 10/1982 | European Pat. Off. . |
| 0 107 559 | 5/1984 | European Pat. Off. . |
| 0 243 947 | 4/1987 | European Pat. Off. . |
| 0 231 091 | 8/1987 | European Pat. Off. . |
| 0 272 091 | 6/1988 | European Pat. Off. . |
| 0 320 433 A2 | 12/1988 | European Pat. Off. . |
| 0 324 938 | 7/1989 | European Pat. Off. . |
| 0 338 971 | 10/1989 | European Pat. Off. . |
| 357 163 A1 | 3/1990 | European Pat. Off. . |
| 0 361 894 | 4/1990 | European Pat. Off. . |
| 0 216 730 | 1/1991 | European Pat. Off. . |
| 0 467 031 A2 | 5/1991 | European Pat. Off. . |
| 441 468 A2 | 8/1991 | European Pat. Off. . |
| 0 357 164 B1 | 10/1991 | European Pat. Off. . |
| 0 458 745 A1 | 11/1991 | European Pat. Off. . |
| 0 314 764 B1 | 9/1992 | European Pat. Off. . |
| 0 554 213 A1 | 8/1993 | European Pat. Off. . |
| 0 586 875 | 3/1994 | European Pat. Off. . |
| 72 255 A2 | 8/1996 | European Pat. Off. . |
| 62 286534 | 12/1987 | Japan . |
| 63-60943 | 3/1988 | Japan . |
| 1044680 | 10/1966 | United Kingdom . |
| 2193095 | 2/1988 | United Kingdom . |
| WO 80/02365 | 11/1980 | WIPO . |
| WO 82/01642 | 5/1982 | WIPO . |

| | | | |
|---|---|---|---|
| 85/01161 | 3/1985 | WIPO . | |
| WO 86/00238 | 1/1986 | WIPO . | |
| WO 86/01103 | 2/1986 | WIPO . | |
| WO 89/05040 | 6/1989 | WIPO . | |
| WO 90/01952 | 3/1990 | WIPO . | |
| WO 90/04384 | 5/1990 | WIPO . | |
| WO 90/04943 | 5/1990 | WIPO . | |
| WO 91/00086 | 1/1991 | WIPO . | |
| WO 91/12823 | 9/1991 | WIPO . | |
| WO 91/15244 | 10/1991 | WIPO . | |
| WO 92/10166 | 6/1992 | WIPO . | |
| WO 92/11873 | 7/1992 | WIPO . | |
| WO 92/17212 | 10/1992 | WIPO . | |
| WO 92/17514 | 10/1992 | WIPO . | |
| WO92/17213 | 10/1992 | WIPO . | |
| WO92/17436 | 10/1992 | WIPO . | |
| WO92/21382 | 12/1992 | WIPO . | |
| WO 93/00993 | 1/1993 | WIPO . | |
| WO 93/05819 | 1/1993 | WIPO . | |
| WO 93/06869 | 4/1993 | WIPO . | |
| WO 93/13808 | 7/1993 | WIPO . | A61K 49/00 |
| WO 93/13809 | 7/1993 | WIPO . | |
| 9317718 | 9/1993 | WIPO . | A61K 49/00 |
| WO93/18070 | 9/1993 | WIPO . | |
| WO 93/20802 | 10/1993 | WIPO . | |
| WO 94/06477 | 3/1994 | WIPO . | |
| WO 94/07539 | 4/1994 | WIPO . | |
| WO 94/09829 | 5/1994 | WIPO . | |
| WO94/16739 | 8/1994 | WIPO . | |
| WO 94/21302 | 9/1994 | WIPO . | |
| WO 94/28780 | 12/1994 | WIPO . | |
| WO 95/06518 | 3/1995 | WIPO . | |
| WO 95/07072 | 3/1995 | WIPO . | |
| WO 95/23615 | 9/1995 | WIPO . | |
| WO 96/04018 | 2/1996 | WIPO . | |
| WO 96/09793 | 4/1996 | WIPO . | |
| WO 96/36286 | 11/1996 | WIPO . | |

OTHER PUBLICATIONS

Nayar et al., "Generation of Large Unilamellar Vesicles From Long–chain Saturated Phosphatidylcholines by Extrusion Technique", *Biochimica et Biophysica Acta,* vol. 986, pp. 200–206 (1989).

Hope et al., "Generation of Multilamellar and Unilamellar Phospholipid Vesicles", *Chemistry and Physics of Lipids,* vol. 40, pp. 89–107 (1986).

Mattrey et al., "Perfluorochemicals as US Contrast Agents for Tumor–Imaging and Hepatosplenography: Preliminary Clinical Results", *Radiology,* vol. 163, pp. 339–343 (1987).

Mattrey et al., "Perfluoroctylbromide: A Liver/Spleen–Specific and Tumor Imaging Ultrasound Contrast Material", *Radiology,* vol. 145, pp. 759–762 (1982).

Keller et al., "Successful Left Ventricular Opacification Following Peripheral Venous Injection of Sonicated Contrast Agent: An Experimental Evaluation", *LV Contrast Echocardiography,* vol. 114, No. 3, pp. 570–575 (1987).

Feinstein et al., "Two–Dimensional Contrast Echocardiography, I: In Vitro Development and Quantitative Analysis of Echo Contrast Agents", *JACC,* vol. 3, No. 1, pp. 14–20 (1984).

Ten Cate et al., "Two–Dimensional Contrast Echocardiography, II: Transpulmonary Studies", *JACC,* vol. 3, No. 1, pp. 21–27 (1984).

Unger et al., "Hepatic Metastases: Liposomal Gd–DTPA–enhanced MR Imaging", *Radiology,* vol. 171, pp. 81–85 (1989).

Deamer et al., "Permeability of Lipid Bilayers to Water and Ionic Solutes", *Chemistry and Physics of Lipids,* vol. 40, pp. 167–188 (1986).

Gutknecht et al., "Diffusion of Carbon Dioxide Through Lipid Bilayer Membranes: Effect of Carbonic Anhydrase, Bicarbonate, and Unstirred Layers", *Chemical Abstracts,* 87:34772q (1977).

Scarpa et al., "Cation Permeability of Liposomes as a Function of the Chemical Composition of the Lipid Bilayers", *Biochimica et Biophysica Acta,* vol. 241, pp. 789–797 (1971).

MacNaughton et al., "Effects of Gaseous Anesthetics and Inert Gases on the Phase Transition in Smectic Mesophases of Dipalmitoyl Phosphatidylcholine", *Biochimica et Biophysica Acta,* vol. 597, pp. 193–198 (1980).

Tilcock et al., "Liposomal Gd–DTPA: Preparation and Characterization of Relaxivity", *Radiology,* vol. 171, pp. 77–80 (1989).

Mann et al., "Formation of Iron Oxides in Unilamellar Vesicles", *Journal of Colloid and Interface Science,* vol. 122, No.2, pp. 326–335 (1988).

Anderson et al., "Manganese (III) Complexes in Oxidative Decarboxylation of Acids", *J. Am. Chem. Soc.,* vol. 92, No.8, pp. 2450–2460 (1970).

Muhlradt et al., "Vitamin B6 Analogs: An Improved Synthesis of 5–Deoxypyridoxal", *New Compounds,* vol. 10, pp. 129–130 (1967).

Chapman D., "Physiochemical Properties of Phospholipids and Lipid Water Systems", *Liposome Technology,* Gregoriadis, G., ed., vol. 1, pp. 1–19 (CRC Press, Boca Raton, FL, 1984).

Violante et al., "Particulate Suspensions as Ultrasonic Contrast Agents for Liver And Spleen", *Inv. Rad.,* vol. 23, pp. S294–S297, Sep. 1988.

Fritzsch et al., "Preclinical and Clinical Results with an Ultrasonic Contrast Agent", *Inv. Rad.,* vol. 23, pp. S302–S305, Sep. 1988.

Brochure, *Experience,* Sonicator™, Heat Systems–Ultrasonics, Inc. (1987).

M. Ostro, "Liposomes", Marcel Dekker, New York, pp. 102–103 (1983).

Fukuda et al., "Polymer–Encased Vesicles Derived from Diotadecyldimethylammonium Methacrylate", *J. Am. Chem. Soc.,* vol. 108, pp. 2321–2327 (1986).

Regen, "Polymerized Vesicles", *J. Am. Chem. Soc.,* vol. 102, pp. 6638–6640 (1989).

Rose, A. and Rose, E., "The Condensed Chemical Dictionary", Reinhold Publishing, New York, pp. 728 and 743 (1966).

A.G. Belykh, *Farmakol Toksikol. (MOSC),* vol. 44(3), pp. 322–326 (1981) (abstract).

J. Vion–Dury et al., *J. Pharmacol. Exper. Ther.,* vol. 250(3), pp. 1113–1118 (1989) (abstract).

M.R. Zalutsky et al., *Invest. Radiol.,* vol. 22(2), pp. 141–147 (1987) (abstract).

Crowe et al., *Archives of Biochemistry and Biophysics,* vol. 242, pp. 240–247 (1985).

Crowe et al., *Archives of Biochemistry and Biophysics,* vol. 220, pp. 477–484 (1983).

Dorland's Illustrated Medical Dictionary, p. 946, 27th ed. (W.B. Saunders Company, Philadelphia 1988).

*Liposome Technology,* Gregoriadis, G., ed., vol. I, pp. 1–18, 29–35, 51–65 and 79–107 (CRC Press Inc., Boca Raton, FL, (1984).

Madden et al., *Chemistry and Physics of Lipids,* vol. 53, pp. 37–46 (1990).

Sinkula et al., *J. Pharm. Sci.,* vol. 64, pp. 181–210 (1975).

Shiina et al., "Hyperthermiaby Low–frequency Synthesized Ultrasound", *IEEE Engineering,* pp. 879–880, vol. 2 (abstract), (1987).

McAvoy et al., *IEEE Engineering, Ultrasonics Symposium Proceedings,* vol. 2, pp. 677–1248 (abstract), (1989).

Chapman et al., "Biomembrane Phase Transitions", *J. Biol. Chem.,* 1974, 249:2512–2521.

Hug et al., "Liposomes for the Transformation of Eukaryotic Cells", *Biochimica et Biophysica Acta,* 1991, 1097:1–17.

Marsh, *CRC Handbook of Lipid Bilayers* (CRC Press, Boca Raton, FL 1990) pp. 139–141.

Szoka et al., "Procedure for Preparation of Liposomes With Large Internal Aqueous Space . . . ", *Proc. Natl. Acad. Sci.* 1978, 75:4194–4198.

Acoustic Imaging; AI5200; Convex Curved Linear Array Ultrasound Transducers Operator's Manual, Nov. 20, 1989, 4700–0003–1C, p. 4.

Bangham et al., "Diffusion of Univalent Ions across the Lamellae of Swollen Phospholipids", *J. Mol. Biol.,* 1965, 13:238–252.

Carson et al., *Ultrasound in Med. & Biol.* 3, 1978, 341–350.

Chiellini et al., *Polymers in Medicine II: Biomedical and Pharmaceutical Applications,* (Plenum Press, New York and London) pp. 387–396, (1983).

deGier et al., "Relations Between Liposomes and Biomembranes", *Annals of The New York Academy of Sciences,* 1978, 308:85–99.

Felgner et al., "Lipofection: A highly efficient, lipid–mediated DNA–transfection procedure", *Proc. Natl. Acad. Sci.,* 1987, 84:7413–7417.

Gabizon et al., "Liposome formulations with prolonged circulation time in blood and enhanced uptake by tumors", *Proc. Natl. Acad. Sci.,* 1988, 85:6949–6953.

Garelli, et al., *Biochimica et Biophysica Acta,* vol. 1127:41–48 (1992).

Kawai et al., "New Procedure for DNA Transfection with Polycation and Dimethyl Sulfoxide", *Molecular and Cellular Biology,* 1984, 4:1172–1174.

Kuo et al., "Metallocene Antitumor Agents. Solution and Solid–State Molybdenocene Coordination . . . ", *J. Am. Chem. Soc.,* 1991, 113:9027–9045.

*Mammalian Cell Biotechnology: A Practical Approach,* M. Butler, 1991 (Oxford University Press, New York), pp. 57–70.

Mathiowitz et al., "Photochemical Rupture of Microcapsules: A Model System", *Journal of Applied Polymer Science,* 1981, 26:809–822.

May et al., "Cationic Liposomes Enable Bovine Herpesvirus Type 2 DNA to Infect Cells", *Acta virol.,* 1991, 35:107.

Poznansky et al., "Biologica Approaches to the Controlled Delivery of Drugs: A Critical Review", *Pharmacol, Rev.,* 1984, 36:277–336.

Sato et al., "Recent Aspects in the Use of Liposomes in Biotechnology and Medicine", *Prog. Lipid Res.* 1992, 4:345–372.

Simons et al., "Antisense c–myb oligonucleotides inhibit intimal arterial smooth muscle cell accumulation in vivo", *Nature,* 1992, 359:67–70.

Thompson, Larry, "At Age 2, Gene Therapy Enters a Growth Phase", *Science* 1992, 258:744–746.

Trubetskoy et al. "Cationic liposomes enhance targeted delivery and expression of exogenous DNA . . . ", Biochimica et Biophysica Acta 1992, 131:311–313.

Umemura et al., "Studies on Sonodynamic Cancer Therapy", *IEEE,* 1992, O–7803–0785, pp. 354–355.

Williams, "Human Gene Therapy: Searching for Better Vectors", *ASM News* [American Society for Microbology] 1992, 58:67–69.

Woodle et al., "Versatility in lipid compositions showing prolonged circulation . . . ", *Biochimica et Biophysica Acta* 1992, 1105:193–200.

Zhou et al., "Targeted delivery of DNA by liposomes and polymers", *J. of Controlled Release* 1992, 19:269–274.

Mathiowitz et al., "Polyanhydride Microspheres as Drug Carriers", *Journal of Applied Polymer Science,* vol. 35, pp. 755–774 (1988).

Sankaram et al., "Cholesterol–Induced Fluid–Phase Immiscibility in Membranes", *Proc. Natl. Acad. Sci.,* vol. 88, pp. 8686–8690 (1991).

*Scientific Apparatus Catalog 92/93* (VWR Scientific, 1991), "Syringes", pp. 1511–1513; "Filtration, Syringe Filters", pp. 766–768; "Filtration, Membranes", pp. 750–753; "Filtration, Filter Holders", p. 744, (1991).

Gramiak et al., *Radiology,* "Detection of Intracardiac Blood Flow by Pulsed Echo–Ranging", pp. 415–418 (1971).

Feigenbaum et al., *Circulation,* "Identification of Ultrasound Echoes from the Left Ventricle by Use of Intracardiac Injections of Indocyanine Green", vol. XL1, pp. 615–621 (1970).

Santaella, et al., *FEBS 13463,* "Extended In Vivo Blood Circulation Time of Fluorinated Liposomes", vol. 336, No. 3, pp. 481–484 (1993).

Kost, et al, *Polymers in Medicine II,* Ultrasonic Modulated Drug Delivery Systems, pp. 387–396, (1988).

Brown and Langer, *Annual Review Medicine,* 1988, 39:221 29, Annual Review, Inc., "Transdermal Delivery of Drugs", pp. 221–229.

Moseley, et al., *Microbubbles: A Novel MR Susceptibility Contrast Agent,* abstract, 1991 Napa, California Meeting of the Society for Magnetic Resonance in Medicine.

Ter–Pogossian, *Physical Principles and Instrumentation,* "Computed Body Tomography", Chapter 1, pp. 1–7, (1985).

Aronberg, *Techniques,* "Computed Body Tomography", Chapter 2, pp. 9–36, (1985).

Miller *Ultrasonics* (Sep. 1981), "Ultrasonic detection of resonant cavitation bubbles in a flow tube by their second-–harmonic emissions," pp. 217–224.

Dittrich, "Cardiac Muscle Ischemia and Infarction", *The Second Annual Int. Symposium on Contrast Agents and Diagnostic Ultrasound,* Atlantic City, NJ (May 7, 1996) (Abstract).

Pantely, "Intravenous Contrast Echocardiography–Tissue Imaging & Quantification of Coronary Blood Flow", *The Second Annual Int. Symposium on Contrast Agents in Diagnostic Ultrasound,* Atlantic City, NJ (May 7, 1996) (Abstract).

Lincoff et al., "Intravitreal Expansion of Perfluorocarbon Bubbles", *Arch. Ophthalmol.,* 1980, 98, 1646.

Lincoff et al., "Intravitreal Longevity of Three Perfluorocarbon Gases", *Arch. Ophthalmol.,* 1980, 98, 1610–1611.

Lincoff et al., "The Perfluorocarbon Gases in the Treatment of Retinal Detachment", *Ophthalmology,* 1983, 90(5), 546–551.

Gardner et al., "A Survey of Intraocular Gas Use in North America", *Arch. Ophthalmol.,* 1988, 106, 1188–1189.

Unger et al., "Liposomal MR Contrast Agents", *J. Liposome Research,* 1994, 4(2), 811–834.

Schutt et al., "Osmotically Stabilized Microbubble Sonographic Contrast Agents", *Acad. Radiol.,* 1996, 3 (Suppl. 2), S188–S190.

Frézard et al., "Permeability and stability in buffer and in human serum of fluorinated phospholipid–based liposomes", *Biochimica et Biophysica Acta,* 1994, 1192, 61–70.

Frézard et al., "Fluorinated Phospholipid–Based Vesicles as Potential Drug Carriers: Encapsulation/Sustaining of Drugs and Stability in Human Serum", *Art, Cells, Blood Subs., and Immob. Biotech.,* 1994, 22(4), 1403–1408.

Chang et al., Semipermeable Aqueous Microcapsules *Canadian J. Of Phys. And Pharm,* 1966, 44, 115–128.

Chang, "Semipermeable Microcapsules", *Science,* 1964, 146, 524–525.

Deasy, Microencapsulation and Related Drug Processes, 1983, 20 (Ch. 9 & 10), 195–240 (Marcell Dekker, Inc., NY).

Yeung et al., "Preparation of Microencapsulated Liposomes", *J. Microencapsulation,* 1988, 5, 331–337.

Mattrey et al., Gas Emulsions as Ultrasound Contrast Agents; Preliminary Results in Rabbits and Dogs, *Investigative Radiology,* 1994, vol. 29, (Jun. Supp. 2), S139–S141.

Meltzer et al., Transmission of Ultrasonic Contrast Through the Lungs, *Ultrasound in Med. & Biol.,* 1981, 7(4), 377–384.

PR Newswire, Apr. 1, 1986.

Swanson et al., "Enhancement Agents for Ultrasound: Fundamentals", *Pharmaceuticals In Medical Imaging,* 1990, Ch. 22, 682–687.

Ophir et al., "Contrast Agents in Diagnostic Ultrasound", *Ultrasound in Med. & Biol.,* vol. 15, No. 4, pp. 319–333 (1989).

Jacobs, P., "Intraocular gas measurement using A–scan ultrasound", *Current Eye Research,* 1986, 5, 575–578.

Villanueva et al., "Characterization of Spatial Patters of Flow Within the Reperfused Myocardium by Myocardial Contrast Echocardiography", *Circulation,* vol. 88, No. 6, pp. 2596–2606 (Dec. 1993).

Desir et al., "Assessment of regional myocardial perfusion with myocardial contrast echocardiography in a canine model of varying degrees of coronary stenosis", *Am. Heart J.,* Jan., 1994, 127(1), 56–63.

Sekins et al., "Lung Cancer Hyperthermia via Ultrasound and PFC Liquids", Published in *Proceedings of 5th International Symposium on Hyperthermic Oncology, Kyoto, Japan,* Aug. 29–Sep. 3, 1998, 3 pages.

Pietersen, "A New Warning System for Fires of Electrical Origin", *CERN European Organization for Nuclear Research, Health and Safety Division,* Mar., 1977, 1–5.

Feinstein, Steven B., "Myocardial Perfusion Imaging: Contrast Echocardiography Today and Tomorrow," *Journal of the American College of Cardiology,* 8(1):251–253 (1986).

Keller et al., "The Behavior of Sonicated Albumin Microbubbles Within the Microcirulation: A Basis for Their Use During Myocardial Contrast Echocardiography", *Circulation Res.,* 65(2):458–465 (1989).

Lincoff et al., "Perfluoro–n–butane: A Gas for Maximum Duration Retinal Tamponade," *Arch Ophthalmology,* 101:460–462 (1983).

*Remington's Pharmaceutical Sciences,* John Hoover, managing ed., Mack Publishing Company, Easton, PA, pp. 295–298; 736; 1242–1244 (1975).

*Handbook of Pharmaceutical Excipients,* American Pharmaceutical Association, Washington, D.C. and The Pharmaceutical Society of Great Britain, London, England, pp. 181–183 (1986).

Miller et al., "Physiochemical Approaches to the Mode of Action of General Anesthetics," *J. Amer. Soc. Anesthesiologists,* 36(4):339–351 (1972).

"Properties and Applications of the 'Freon' Fluorocarbons" in DuPont Freon Technical Bulletin B–2 (E.I. DuPont de Nemours and Company, Wilmington, DE), pp. 1–11 (1964).

"'Freon' Fluorocarbons: Properties and Applications" in DuPont Technical Bulletin G–1 (E.I. DuPont de Nemours and Company, Wilmington, DE), pp. 1–10 (1987).

"Encyclopedia of Polymer Science and Engineering," John Wiley & Sons, New York, 1:164–169 (1985).

"Concise Encyclopedia of Polymer Science and Engineering," J. Kroschwitz, ed., John Wiley & Sons, New York, pp. 12–13 (1990).

Wheatley et al., "Contrast Agents for Diagnostic Ultrasound: Development and Evaluation of Polymer–Coated Microbubbles," *Biomaterials,* 11:713–717 (1990).

THE SMALLEST DIVISION ON THE SCALE SHOWN EQUALS 10 MICRONS

THE SMALLEST DIVISION ON THE SCALE SHOWN EQUALS 10 MICRONS

GASEOUS PRECURSOR FILLED MICROSPHERES AS MAGNETIC RESONANCE IMAGING CONTRAST AGENTS

REFERENCE TO COPENDING APPLICATIONS

This application is a continuation-in-part of U.S. Ser. No. 08/212,553 filed Mar. 11, 1994, now abandoned.

This application is also a continuation-in-part of U.S. Ser. No. 08/076,250 filed Jun. 11, 1993, now U.S. Pat. No. 5,580,575, which is a continuation-in-part of U.S. Ser. No. 07/716,899 filed Jun. 18, 1991, now abandoned, and U.S. Ser. No. 07/717,084 filed Jun. 18, 1991, now U.S. Pat. No. 5,228,446, both of which are continuations-in-part of U.S. Ser. No. 07/569,828 filed Aug. 20, 1990, now U.S. Pat. No. 5,088,499, which in turn is a continuation-in-part of U.S. Ser. No. 07/455,707 filed Dec. 22, 1989, now abandoned. Ser. No. 08/076,250 discloses therapeutic drug delivery systems comprising gas filled microspheres containing a therapeutic agent, with particular emphasis on the use of ultrasound techniques to monitor and determine the presence of said microspheres in a patient's body, and then to rupture said microspheres in order to release said therapeutic agent in the region of the patient's body where said microspheres are found.

This application is also a continuation-in-part of U.S. Ser. No. 08/076,239 filed Jun. 11, 1993, now U.S. Pat. No. 5,469,854, which is a continuation-in-part of U.S. Ser. No. 07/716,899 filed Jun. 18, 1991, now abandoned, and U.S. Ser. No. 07/717,084 filed Jun. 18, 1991, now U.S. Pat. No. 5,229,446, both of which are continuations-in-part of U.S. Ser. No. 07/569,828 filed Aug. 20, 1990, now U.S. Pat. No. 5,088,499, which in turn is a continuation-in-part of U.S. Ser. No. 07/455,707 filed Dec. 22, 1989, now abandoned. Ser. No. 08/076,239 discloses methods and apparatus for preparing gas filled microspheres suitable for use as contrast agents for ultrasonic imaging or as drug delivery agents.

This application is also a continuation-in-part of U.S. Ser. No. 08/307,305 filed Sep. 16, 1994, U.S. Pat. No. 5,773,024, which is a continuation-in-part of U.S. Ser. No. 08/212,553, filed Mar. 11, 1994, now abandoned, and U.S. Ser. No. 08/159,687 filed Nov. 30, 1993, now U.S. Pat. No. 5,585, 112, which is a continuation-in-part of U.S. Ser. No. 08/160, 232, filed Nov. 30, 1993, now U.S. Pat. No. 5,542,935 and U.S. Ser. No. 08/159,674 filed Nov. 30, 1993, now abandoned.

This application is also a continuation-in-part of U.S. Ser. No. 08/159,687 filed Nov. 30, 1993, now U.S. Pat. No. 5,585,112, which is a continuation-in-part of U.S. Ser. No. 08/160,232 filed Nov. 30, 1993, now U.S. Pat. No. 5,542, 935, and U.S. Ser. No. 08/159,674 filed Nov. 30, 1993, now abandoned.

This application is also a continuation-in-part of U.S. Ser. No. 08/160,232, filed Nov. 30, 1993, now U.S. Pat. No. 5,542,935, which is a continuation-in-part of U.S. Ser. No. 08/159,687 filed Nov. 30, 1993, now U.S. Pat. No. 5,585, 112, and U.S. Ser. No. 08/159,674 filed Nov. 30, 1993, now abandoned.

Application Ser. Nos. 08/307,305, 08/159,687 and 08/160,232 disclose novel therapeutic delivery systems and methods of preparing gas and gaseous precursor filled microspheres and multiphase lipid and gas compositions useful in diagnostic and therapeutic applications.

Benefit of the filing dates of applications Ser. Nos. 08/212, 553, 08/307,305, 08/159,687, 08/160,232, 08/076,239 and 08/076,250 and their parentage is hereby claimed, and they are incorporated herein by reference in their entirety.

Reference is also made to application Ser. No. 07/507,125 filed Apr. 10, 1990, which discloses the use of biocompatible polymers, either alone or in admixture with one or moire contrast agents such as paramagnetic, superparamagnetic or proton density contrast agents. The polymers or polymer/ contrast agent admixtures may optionally be admired with one or more biocompatible gases to increase the relaxivity of the resultant preparation.

BACKGROUND OF THE INVENTION

1. Field of the Invention

This invention relates to the field of magnetic resonance imaging, more specifically to the use of stabilized gas filled microspheres as contrast media for magnetic resonance imaging (MRI).

There are a variety of imaging techniques that have been used to diagnose disease in humans. One of the first imaging techniques employed was X-rays. In X-rays, the images produced of the patients' body reflect the different densities of body structures. To improve the diagnostic utility of this imaging technique, contrast agents are employed to increase the density of tissues of interest as compared to surrounding tissues to make the tissues of interest more visible on X-ray. Barium and iodinated contrast media, for example, are used extensively for X-ray gastrointestinal studies to visualize the esophagus, stomach, intestines and rectum. Likewise, these contrast agents are used for X-ray computed tomographic studies (that is, computer assisted tomography or CAT) to improve visualization of the gastrointestinal tract and to provide, for example, a contrast between the tract and the structures adjacent to it, such as the vessels or lymph nodes. Such contrast agents permit one to increase the density inside the esophagus, stomach, intestines and rectum, and allow differentiation of the gastrointestinal system from surrounding structures.

Magnetic resonance imaging (MRI) is a relatively new imaging technique which, unlike X-rays, does not utilize ionizing radiation. Like computer assisted tomography (CAT), MRI can make cross-sectional images of the body, however MRI has the additional advantage of being able to make images in any scan plane (i.e., axial, coronal, sagittal or orthogonal). Unfortunately, the full utility of MRI as a diagnostic modality for the body is hampered by the need for new or better contrast agents. Without suitable agents, it is often difficult using MRI to differentiate the target tissue from adjacent tissues. If better contrast agents were available, the overall usefulness of MRI as an imaging tool would improve, and the diagnostic accuracy of this modality would be greatly enhanced.

MRI employs a magnetic field, radio frequency energy and magnetic field gradients to make images of the body. The contrast or signal intensity differences between tissues mainly reflect the T1 (longitudinal) and T2 (transverse) relaxation values and the proton density (effectively, the free water content) of the tissues. In changing the signal intensity in a region of a patient by the use of a contrast medium, several possible approaches are available. For example, a contrast medium could be designed to change either the T1, the T2 or the proton density.

2. Brief Description of the Prior Art

In the past, attention has mainly been focused on paramagnetic contrast media for MRI. Paramagnetic contrast agents contain unpaired electrons which act as small local magnets within the main magnetic field to increase the rate of longitudinal (T1) and transverse (T2) relaxation. Most paramagnetic contrast agents are metal ions which in most cases are toxic. In order to decrease toxicity, these metal ions are generally chelated using ligands. The resultant paramagnetic metal ion complexes have decreased toxicity. Metal oxides, most notably iron oxides, have also been tested as MRI contrast agents. While small particles of iron oxide, e.g., under 20 nm diameter, may have paramagnetic relaxation properties, their predominant effect is through bulk susceptibility. Therefore magnetic particles have their predominant effect on T2 relaxation. Nitroxides are another class of MRI contrast agent which are also paramagnetic. These have relatively low relaxivity and are generally less effective than paramagnetic ions as MRI contrast agents. All of these contrast agents can suffer from some toxic effects in certain use contexts and none of them are ideal for use as perfusion contrast agents by themselves.

The existing MRI contrast agents suffer from a number of limitations. For example, positive contrast agents are known to exhibit increased image noise arising from intrinsic peristaltic motions and motions from respiration or cardiovascular action. Positive contrast agents such as Gd-DTPA are subject to the further complication that the signal intensity depends upon the concentration of the agent as well as the pulse sequence used. Absorption of contrast agent from the gastrointestinal tract, for example, complicates interpretation of the images, particularly in the distal portion of the small intestine, unless sufficiently high concentrations of the paramagnetic species are used (Kornmesser et al., *Magn. Reson. Imaging*, 6:124 (1988)). Negative contrast agents, by comparison, are less sensitive to variation in pulse sequence and provide more consistent contrast. However at high concentrations, particulates such as ferrites can cause magnetic susceptibility artifacts which are particularly evident, for example, in the colon where the absorption of intestinal fluid occurs and the superparamagnetic material may be concentrated. Negative contrast agents typically exhibit superior contrast to fat, however on T1-weighted images, positive contrast agents exhibit superior contrast versus normal tissue. Since most pathological tissues exhibit longer T1 and T2 than normal tissue, they will appear dark on T1-weighted and bright on T2-weighted images This would indicate that an ideal contrast agent should appear bright on T1-weighted images and dark on T2-weighted images. Many of the currently available MRI contrast media fail to meet these dual criteria.

Toxicity is another problem with the existing contrast agents. With any drug there is some toxicity, the toxicity generally being dose related. With the ferrites there are often symptoms of nausea after oral administration, as well as flatulence and a transient rise in serum iron. The paramagnetic contrast agent Gd-DTPA is an organometallic complex of gadolinium coupled with the complexing agent diethylene triamine pentaacetic acid. Without coupling, the free gadolinium ion is highly toxic. Furthermore, the peculiarities of the gastrointestinal tract, for example, wherein the stomach secretes acids and the intestines release alkalines, raise the possibility of decoupling and separation of the free gadolinium or other paramagnetic agent from the complex as a result of these changes in pH during gastrointestinal use. Certainly, minimizing the dose of paramagnetic agents is important for minimizing any potential toxic effects.

New and/or better contrast agents useful in magnetic resonance imaging are needed. The present invention is directed, inter alia, to this important end.

In the work on MRI contrast agents described above for application Ser. No. 07/507,125, filed Apr. 10, 1990, it has been disclosed how gas can be used in combination with polymer compositions and paramagnetic or superparamagnetic agents as MRI contrast agents. Therein it has been shown how the gas stabilized by said polymers would function as an effective susceptibility contrast agent to decrease signal intensity on T2 weighted images; and that such systems are particularly effective for use as gastrointestinal MRI contrast media.

Widder et al. published application EP-A-0 324 938 discloses stabilized microbubble-type ultrasonic imaging agents produced from heat-denaturable biocompatible protein, e.g., albumin, hemoglobin, and collagen.

There is also mentioned a presentation believed to have been made by Moseley et al., at a 1991 Napa, Calif. meeting of the Society for Magnetic Resonance in Medicine, which is summarized in an abstract entitled "Microbubbles: A Novel MR Susceptibility Contrast Agent". The microbubbles which are utilized comprise air coated with a shell of human albumin. The stabilized gas filled microspheres of the present invention are not suggested.

For intravascular use, however, the inventors have found that for optimal results, it is advantageous that any gas be stabilized with flexible compounds. Proteins such as albumin may be used to stabilize the bubbles but the resulting bubble shells may be brittle and inflexible. This is undesirable for several reasons. Firstly, a brittle coating limits the capability of the bubble to expand and collapse. As the bubble encounters different pressure regions within the body (e.g., moving from the venous system into the arteries upon circulation through the heart) a brittle shell may break and the gas will be lost. This limits the effective period of time for which useful contrast can be obtained in vivo from the bubbles contrast agents. Also such brittle, broken fragments can be potentially toxic. Additionally the inflexible nature of brittle coatings such as albumin, and stiff resulting bubbles make it extremely difficult to measure pressure in vivo.

Quay published application WO 93/05819 discloses that gases with high Q numbers are ideal for forming stable gases, but the disclosure is limited to stable gases, rather than their stabilization and encapsulation, as in the present invention. In a preferred embodiment described on page 31, sorbitol is used to increase viscosity, which in turn is said to extend the life of a microbubble in solution. Also, it is not an essential requirement of the present invention that the gas involved have a certain Q number or diffusibility factor.

Lanza et al. published application WO 93/20802 discloses acoustically reflective oligolamellar liposomes, which are multilamellar liposomes with increased aqueous space between bilayers or have liposomes nested within bilayers in a nonconcentric fashion, and thus contain internally separated bilayers. Their use as ultrasonic contrast agents to enhance ultrasonic imaging, and in monitoring a drug delivered in a liposome administered to a patient, is also described.

D'Arrigo U.S. Pat. Nos. 4,684,479 and 5,215,680 disclose gas-in-liquid emulsions and lipid-coated microbubbles, respectively.

In accordance with the present invention it has been discovered that stabilized gas filled microspheres are extremely effective, non-toxic contrast agents for MRI.

SUMMARY OF THE INVENTION

The present invention is directed to a contrast medium useful for magnetic resonance imaging, said contrast medium comprising stabilized gas filled microspheres, wherein the gas is a biocompatible gas, e.g., nitrogen or perfluoropropane, but may also be derived from a gaseous precursor, e.g., perfluorooctylbromide, and the microspheres are stabilized by being formed from a stabilizing compound, e.g., a biocompatible lipid or polymer. The present invention may be carried out, often with considerable attendant advantage, by using gaseous precursors to form the gas of the gas filled microspheres. These gaseous precursors may be activated by a number of factors, but preferably are temperature activated. Such a gaseous precursor is a compound which, at a selected activation or transition temperature, changes phases from a liquid to a gas. Activation thus takes place by increasing the temperature of the compound from a point below, to a point above the activation or transition temperature The lipid may be in the form of a monolayer or bilayer, and the mono- or bilayer lipids may be used to form a series of concentric mono- or bilayers. Thus, the lipid may be used to form a unilamellar liposome (comprised of one monolayer or bilayer lipid), an oligolamellar liposome (comprised of two or three monolayer or bilayer lipids) or a multilamellar liposome (comprised of more than three monolayer or bilayer lipids). Preferably, the biocompatible lipid comprises a phospholipid. Optionally, the contrast medium may include paramagnetic and/or superparamagnetic contrast agents, preferably encapsulated by the microspheres. Also, optionally, the contrast medium may further comprise a liquid fluorocarbon compound, e.g., a perfluorocarbon, to further stabilize the microspheres. Preferably the fluorocarbon liquid is encapsulated by the microspheres.

The present invention also concerns a method for preparing stabilized gas or gaseous precursor filled lipid based microspheres for use as a magnetic resonance imaging contrast medium, comprising the step of agitating an aqueous suspension of the lipid (that is, the lipid stabilizing compound), in the presence of a gas or gaseous precursor, resulting in gas or gaseous precursor filled microspheres. Desirably, the agitation step is carried out at a temperature below the gel to liquid crystalline phase transition temperature of the lipid in order to achieve a preferred end product.

Where a gaseous precursor is used, the gaseous precursor filled microsphere composition is generally maintained at a temperature at which the gaseous precursor is liquid until administration to the patient. At the time of administration the temperature may, if desired, be raised to activate the gaseous precursor to form a gas and the resultant gas filled microsphere then administered to the patient. Alternatively, the gaseous precursor filled microspheres may, if desired, be administered without raising the temperature, and the gaseous precursor allowed to form a gas as a result of the temperature of the patient. The composition may be agitated, if necessary, prior to administration.

The present invention further pertains to a method of providing an image of an internal region of a patient, especially an image of the vasculature (including the cardiovascular region), particularly during perfusion, and of the gastrointestinal region of said patient, said method comprising (i) administering to the patient the foregoing contrast medium, and (ii) scanning the patient using magnetic resonance imaging to obtain visible images of said region.

Finally, the present invention also encompasses a method for diagnosing the presence of diseased tissue in a patient, especially in the vasculature (including the cardiovascular region), particularly during perfusion; and in the gastrointestinal region of said patient, said method comprising (i) administering to the patient the foregoing contrast medium, and (ii) scanning the patient using magnetic resonance imaging to obtain visible images of any diseased tissue in the region.

These and other aspects of the invention will become more apparent from the following detailed description when taken in conjunction with the following drawings.

BRIEF DESCRIPTION OF THE FIGURES

FIG. 5 is a graphic representation of the relationship between $1/T_2$ (in seconds) versus gas concentrations for several different gases. Samples of gas filled microspheres were prepared using different gases. The gas filled microspheres were then scanned by magnetic resonance using a Brinker Biospec II 4.7 Tesla scanner (Bruker, Billerica, Mass.). T2 measurements were performed by scanning the samples with Spin Echo Sequences TR=800 msec and TE=30, 45, 60, 75 and 90 msec and gradient echo sequences for signal intensity measurements with TR=60 msec, TE=8 with a 40% flip.

DETAILED DESCRIPTION OF THE INVENTION

Figure 1A:
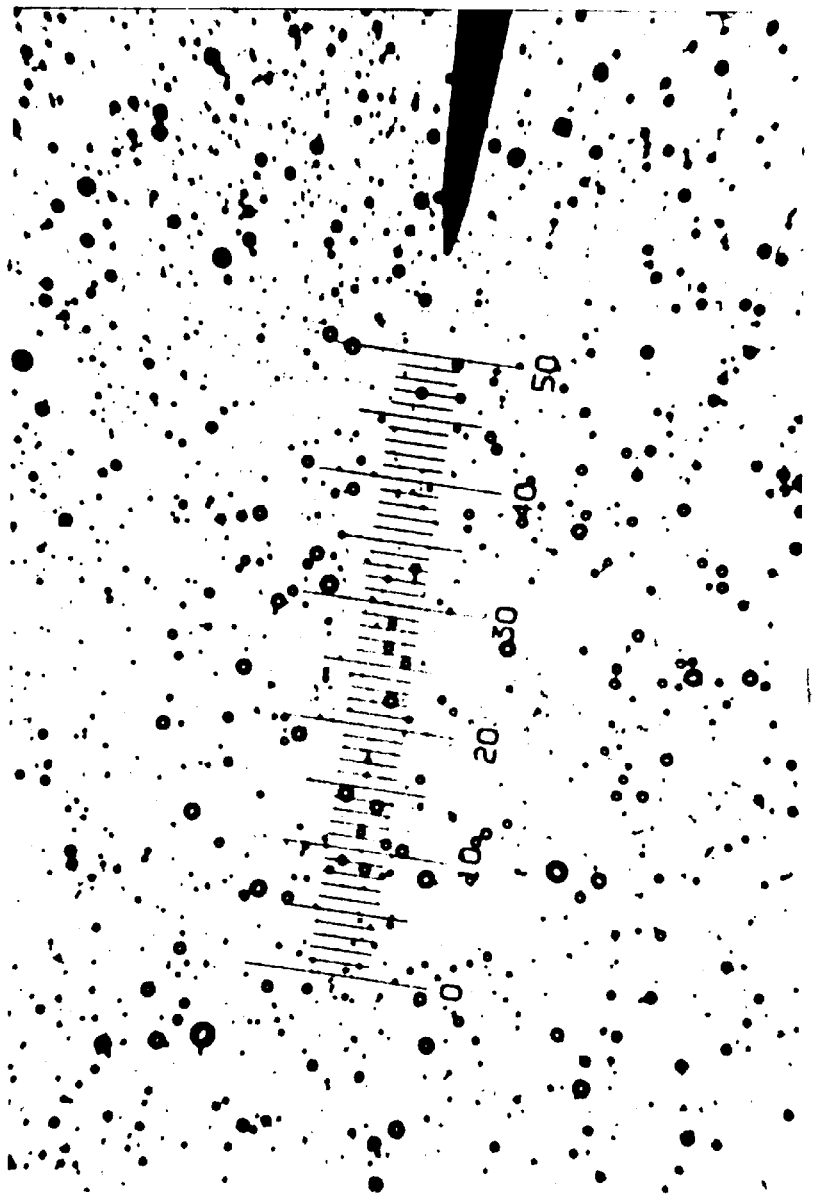
FIGS. 1A and B are photomicrographs of stabilized gas filled microspheres having an approximate mean diameter of 10 microns.
Figure 1B:
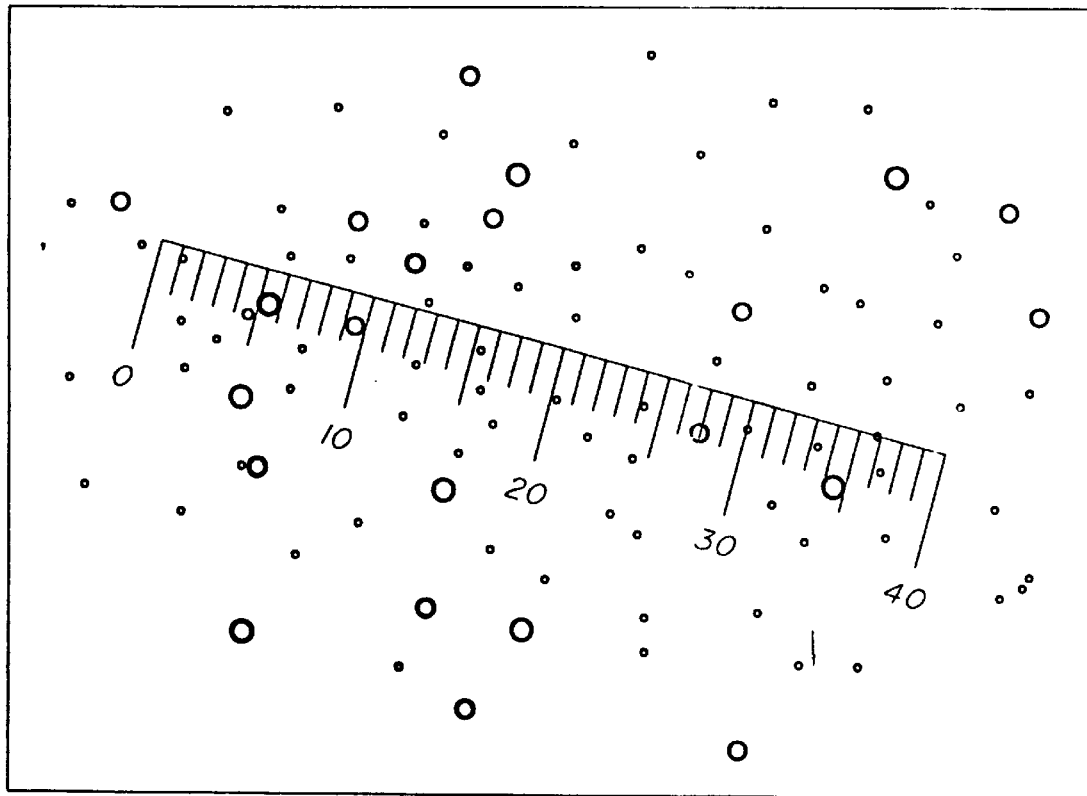

The present invention is directed, inter alia, to stabilized gas filled microspheres. While not intending to be bound by any particular theory of operation, the present invention is believed to rely, at least in part, on the fact that gas, liquid and solid phases have different magnetic susceptibilities. At the interface of gas and water, for example, the magnetic domains are altered and this results in dephasing of the spins of, e.g., the hydrogen nuclei. In imaging this is seen as a decrease in signal intensity adjacent to the gas/water interface. This effect is more marked on T2 weighted images and most prominent on gradient echo pulse sequences. The effect is increased by using narrow bandwidth extended read-out pulse sequences. The longer the echo time on a gradient echo pulse sequence, the greater the effect (i.e., the greater the degree and size of signal loss).

The stabilized gas filled microspheres of the present invention are believed to rely on this phase magnetic susceptibility difference, as well as on the other characteristics described in more detail herein, to provide high performance level magnetic resonance imaging contrast agents. The microspheres are formed from, i.e., created out of, a matrix of stabilizing compounds which permit the gas filled microspheres to be established and thereafter retain their size and shape for the period of time required to be useful in magnetic resonance imaging. These stabilizing compounds are most typically those which have a hydrophobic/hydrophilic character which allows them to form monolayers or bilayers, etc., and microspheres, in the presence of water. Thus, water, saline or some other water-based medium, often referred to hereafter as a diluent, is generally an aspect of the stabilized gas filled microsphere contrast medium of the present invention.

The stabilizing compound may, in fact, be a mixture of compounds which contribute various desirable attributes to the stabilized microspheres. For example, compounds which assist in the dissolution or dispersion of the fundamental stabilizing compound have been found advantageous. A further element of the stabilized microspheres is a gas, which can be a gas at the time the microspheres are made, or can be a gaseous precursor which, responsive to an activating factor, such as temperature, is transformed from the liquid phase to the gas phase. The various aspects of the stabilized gas filled contrast media of the present invention will now be described, starting with the gases which comprise the microspheres.

Gases and Gaseous Precursors

The microspheres of the invention encapsulate a gas and/or gaseous precursor. The term "gas filled and/or gaseous precursor filled", as used herein, means that the microspheres to which the present invention is directed, have an interior volume that is comprised of at least about 10% gas and gaseous precursor, preferably at least about 25% gas and gaseous precursor, more preferably at least about 50% gas and gaseous precursor, even more preferably at least about 75% gas and gaseous precursor, and most preferably at least about 90% gas and gaseous precursor. In use, where the presence of gas is important, it is preferred that the interior microsphere volume comprise at least about 10% gas, preferably at least about 25%, 50%, 75%, and most preferably at least about 90% gas.

Any of the various biocompatible gases and gaseous precursors may be employed in the gas and gaseous precursor filled microspheres of the present invention Such gases include, for example, air, nitrogen, carbon dioxide, oxygen, argon, fluorine, xenon, neon, helium, or any and all combinations thereof. Of such gases, nitrogen is preferred. Likewise, various fluorinated gaseous compounds, such as various perfluorocarbon, hydrofluorocarbon, and sulfur hexafluoride gases may be utilized in the preparation of the gas filled microspheres. Also, the gases discussed in Quay, published application WO 93/05819, including the high "IQ" factor gases described therein, the disclosures of which are hereby incorporated herein by reference in their entirety, may be employed. Further, paramagnetic gases or gases such as $^{17}O$ may be used. Of all of the gases, perfluorocarbons and sulfur hexafluoride are preferred. Suitable perfluorcarbon gases include, for example, perfluorobutane, perfluorocyclobutane, perfluoromethane, perfluoroethane, perfluoropropane, and perfluoropentane, most preferably perfluoropropane. Also preferred are a mixture of different types of gases, such as a perfluorocarbon gas and another type of gas such as oxygen, etc. Indeed, it is believed that a combination of gases may be particularly useful in magnetic resonance imaging applications. Table 3 in the Examples below shows the R2 (1/T2/mmol/L.sec−1) for different gases in lipid microspheres (the higher the R2 relaxation values, the more effective as an MRI contrast medium). As Table 3 shows, there may be dramatic differences in the relaxivity of different gas filled microspheres.

Notwithstanding the requirement that the gas and gaseous precursor filled microspheres be made from stabilizing compounds, it is preferred that a rather highly stable gas be utilized as well. By highly stable gas is meant a gas selected from those gases which will have low (limited) solubility and diffusability in aqueous media. Gases such as perfluorocarbons are less diffusible and relatively insoluble and as such are easier to stabilize into the form of bubbles in aqueous media.

The use of gaseous precursors is an optional embodiment of the present invention. In particular, perfluorocarbons have been found to be suitable for use as gaseous precursors. As the artisan will appreciate, a given perfluorocarbon may be used as a gaseous precursor, i.e., in the liquid state when the microspheres of the present invention are first made, or may be used as a gas directly, i.e., in the gas state, to make the gas and gaseous precursor filled microspheres. Whether such a perfluorocarbon is a gas or liquid depends, of course, on its liquid/gas phase transition temperature, or boiling point. For example, one of the more preferred perfluorocarbons is perfluoropentane, which has a liquid/gas phase transition temperature or boiling point of 27° C., which means that it will be a liquid at ordinary room temperature, but will become a gas in the environment of the human body, where the temperature will be above its liquid/gas phase transition temperature or boiling point. Thus, under normal circumstance, perfluoropentane is a gaseous precursor. As further examples, there is perfluorobutane and perflurohexane, the next closest homologs of perfluoropentane. The liquid/gas phase transition temperature of perfluorobutane is 4° C. and that of perfluorohexane is 57° C., making the former potentially a gaseous precursor, but generally more useful as a gas, while the latter would generally be a gaseous precursor, except under unusual circumstances, because of its high boiling point.

Another aspect of the present invention is the use of a fluorinated compound, especially a perfluorocarbon compound, which will be in the liquid state at the temperature of use of the microspheres of the present invention, to assist or enhance the stability of said gas and gaseous precursor filled microspheres. Such fluorinated compounds include various liquid fluorinated compounds, such as fluorinated surfactants manufactured by the DuPont Company (Wilmington, Del.), e.g., Zonyl™, as well as liquid perfluorocarbons. Preferably the fluorinated compounds are perfluorocarbons. Suitable perfluorocarbons useful as additional stabilizing agents include perfluorooctylbromide (PFOB), perfluorodecalin, perfluorododecalin, perfluorooctyliodide, perfluorotripropylamine, and perfluorotributylamine. In general, perfluorocarbons over six carbon atoms in length will not be gaseous, i.e., in the gas state, but rather will be liquids, i.e., in the liquid state, at normal human body temperature. These compounds may, however, additionally be utilized in preparing the stabilized gas and gaseous precursor filled microspheres used in the present invention. Preferably this perfluorocarbon is perfluorooctylbromide or perfluorohexane, which is in the liquid state at room temperature. The gas which is present may be, e.g., nitrogen or perfluoropropane, or may be derived from a gaseous precursor, which may also be a perfluorocarbon, e.g., perfluoropentane. In that case, the microspheres of the present invention would be prepared from a mixture of perfluorocarbons, which for the examples given, would be perfluoropropane (gas) or perfluoropentane (gaseous precursor) and perfluorooctylbromide (liquid). Although not intending to be bound by any theory, it is believed that the liquid fluorinated fluorinated compound is situated at the interface between the gas and the membrane surface of the microsphere. There is thus formed a further stabilizing layer of liquid fluorinated compound on the internal surface of the stabilizing compound, e.g., a biocompatible lipid used to form the microsphere, and this perfluorocarbon layer also serves the purpose of preventing the gas from diffusing through the microsphere membrane. A gaseous precursor, within the context of the present invention, is a liquid at the temperature of manufacture and/or storage, but becomes a gas at least at or during the time of use.

Thus, it has been discovered that a liquid fluorinated compound, such as a perfluorocarbon, when combined with a gas or gasesous precursor ordinarily used to make the microspheres of the present invention, may confer an added degree of stability not otherwise obtainable with the gas or gaseous precursor alone. Thus, it is within the scope of the present invention to utilize a gas or gaseous precursor, such as a perfluorocarbon gaseous precursor, e.g., perfluoropentane, together with a perfluorocarbon which remains liquid after administration to a patient, i.e., whose liquid to gas phase transition temperature is above the body temperature of the patient, e.g., perfluoroctylbromide.

Any biocompatible gas or gaseous precursor may be used to form the stabilized gas and gaseous precursor filled microspheres. By "biocompatible" is meant a gas or gaseous precursor which, when introduced into the tissues of a human patient, will not result in any degree of unacceptable toxicity, including allergenic responses and disease states, and preferably are inert. Such a gas or gaseous precursor should also be suitable for making gas and gaseous precursor filled microspheres, as described herein.

The size of the gas or gaseous precursor filled microspheres becomes stabilized when the stabilizing compounds described herein are employed; and the size of the microspheres can then be adjusted for the particular intended MRI end use. For example, magnetic resonance imaging of the vasculature may require microspheres that are no larger that about 30µ in diameter, and that are preferably smaller, e.g., no larger than about 12µ in diameter. The size of the gas filled microspheres can be adjusted, if desired, by a variety of procedures including microemulsification, vortexing, extrusion, filtration, sonication, homogenization, repeated freezing and thawing cycles, extrusion under pressure through pores of defined size, and similar methods.

For intravascular use the microspheres are generally under 30µ in mean diameter, and are preferably under about 12µ in mean diameter. For targeted intravascular use, e.g., to bind to a certain tissue such as a tumor, the microspheres can be appreciably under a micron, even under 100 nm diameter. For enteric, i.e., gastrointestinal use the microspheres can be much larger, e.g., up to a millimeter in size, but microspheres between 20µ and 100µ in mean diameter are preferred.

As noted above, the embodiments of the present invention may also include, with respect to their preparation, formation and use, gaseous precursors that can be activated by temperature. Further below is set out a table listing a series of gaseous precursors which undergo phase transitions from liquid to gaseous states at relatively close to normal body temperature (37° C.) or below, and the size of the emulsified droplets that would be required to form a microbubble of a maximum size of 10 microns.

TABLE I

Physical Characteristics of Gaseous Precursors and Diameter of Emulsified Droplet to Form a 10 µm Microsphere*

| Compound | Molecular Weight | Boiling Point (° C.) | Density | Diameter (µm) of emulsified droplet to make 10 micron microsphere |
|---|---|---|---|---|
| perfluoro pentane | 288.04 | 57.73 | 1.7326 | 2.9 |
| 1-fluorobutane | 76.11 | 32.5 | 6.7789 | 1.2 |
| 2-methyl butane (isopentane) | 72.15 | 27.8 | 0.6201 | 2.6 |
| 2-methyl 1-butene | 70.13 | 31.2 | 0.6504 | 2.5 |
| 2-methyl-2-butene | 70.13 | 38.6 | 0.6623 | 2.5 |
| 1-butene-3-yne-2-methyl | 66.10 | 34.0 | 0.6801 | 2.4 |
| 3-methyl-1-butyne | 68.12 | 29.5 | 0.6660 | 2.5 |
| octafluoro cyclobutane | 200.04 | −5.8 | 1.48 | 2.8 |
| decafluoro butane | 238.04 | −2 | 1.517 | 3.0 |
| hexafluoro ethane | 138.01 | −78.1 | 1.607 | 2.7 |

*Source: Chemical Rubber Company Handbook of Chemistry and Physics, Robert C. Weast and David R. Lide, eds., CRC Press, Inc. Boca Raton, Florida (1989–1990).

There is also set out below a list composed of potential gaseous precursors that may be used to form microspheres of defined size. However, the list is not intended to be limiting, since it is possible to use other gaseous precursors for that purpose. In fact, for a variety of different applications, virtually any liquid can be used to make gaseous precursors so long as it is capable of undergoing a phase transition to the gas phase upon passing through the appropriate temperature, so that at least at some point in use it provides a gas. Suitable gaseous precursors for use in the present invention are the following: hexafluoro acetone, isopropyl acetylene, allene, tetrafluoroallene, boron trifluoride, isobutane, 1,2-butadiene, 2,3-butadiene, 1,3-butadiene, 1,2,3-trichloro-2-fluoro-1,3-butadiene, 2-methyl-1,3-butadiene, hexafluoro-1,3-butadiene, butadiyne, 1-fluoro-butane, 2-methyl-butane, decafluorobutane, 1-butene, 2-butene, 2-methyl-1-butene, 3-methyl-1-butene, perfluoro-1-butene, perfluoro-2-butene, 4-phenyl-3-butene-2-one, 2-methyl-1-butene-3-yne, butyl nitrate, 1-butyne, 2-butyne, 2-chloro-1,1,1,4,4,4-hexafluorobutyne, 3-methyl-1-butyne, perfluoro-2-butyne, 2-bromobutyraldehyde, carbonyl sulfide, crotononitrile, cyclobutane, methylcyclobutane, octafluoro-cyclobutane, perfluorocyclobutene, 3-chlorocyclopentene, octafluorocyclopentene-cyclopropane, 1,2-dimethyl-cyclopropane, 1,1-dimethylcyclopropane, 1,2-dimethyl-cyclopropane, ethylcyclopropane, methylcyclopropane, diacetylene, 3-ethyl-3-methyl diaziridine, 1,1,1-trifluorodiazoethane, dimethyl amine, hexafluorodimethylamine, dimethylethylamine, bis(dimethylphosphine)amine, perfluorohexane, 2,3-dimethyl-2-norbornane, perfluorodimethylamine, dimethyloxonium chloride, 1,3-dioxolane-2-one, 4-methyl-1,1,1,2-tetrafluoroethane, 1,1,1-trifluoroethane, 1,1,2,2-tetrafluoroethane, 1,1,2-trichloro-1,2,2-trifluoroethane, 1,1-dichloroethane, 1,1-dichloro-1,2,2,2-tetrafluoroethane, 1,2-difluoroethane, 1-chloro-1,1,2,2,2-pentafluoroethane, 2-chloro-1,1-difluoroethane, 1,1-dichloro-2-fluoroethane, 1-chloro-1,1,2,2-tetrafluoroethane, 2-chloro-1,1-difluoroethane, chloroethane, chloropentafluoroethane, dichlorotrifluoroethane, fluoroethane, hexafluoroethane, nitropentafluoroethane, nitrosopentafluoroethane, perfluoroethylamine, ethyl vinyl ether, 1,1-dichloroethane, 1,1-dichloro-1,2-difluoroethane, 1,2-difluoroethane, methane, trifluoromethanesulfonylchloride, trifluoromethanesulfonylfluoride, bromodifluoronitrosomethane, bromofluoromethane, bromochlorofluoromethane, bromotrifluoromethane, chlorodifluoronitromethane, chlorodinitromethane, chlorofluoromethane, chlorotrifluoromethane, chlorodifluoromethane, dibromodifluoromethane, dichlorodifluoromethane, dichlorofluoromethane, difluoromethane, difluoroiodomethane, disilanomethane, fluoromethane, iodomethane, iodotrifluoromethane, nitrotrifluoromethane, nitrosotrifluoromethane, tetrafluoromethane, trichlorofluoromethane, trifluoromethane, 2-methylbutane, methyl ether, methyl isopropyl ether, methyllactate, methylnitrite, methylsulfide, methyl vinyl ether, neon, neopentane, nitrogen ($N_2$), nitrous oxide, 1,2,3-nonadecane-tricarboxylic acid-2-hydroxytrimethylester, 1-nonene-3-yne, oxygen ($O_2$), 1,4-pentadiene, n-pentane, perfluoropentane, 4-amino-4-methylpentan-2-one, 1-pentene, 2-pentene (cis), 2-pentene (trans), 3-bromopent-1-ene, perfluoropent-1-ene, tetrachlorophthalic acid, 2,3,6-trimethylpiperidine, propane, 1,1,1,2,2,3-hexafluoropropane, 1,2-epoxypropane, 2,2-difluoropropane, 2-aminopropane, 2-chloropropane, heptafluoro-1-nitropropane, heptafluoro-1-nitrosopropane, perfluoropropane, propene, hexafluoropropane, 1,1,1,2,3,3-hexafluoro-2,3 dichloropropane, 1-chloropropane, chloropropane-(trans), 2-chloropropane, 3-fluoropropane, propyne, 3,3,3-trifluoropropyne, 3-fluorostyrene, sulfur hexafluoride, sulfur (di)-decafluoride($S_2F_{10}$), 2,4-diaminotoluene, trifluoroacetonitrile, trifluoromethyl peroxide, trifluoromethyl sulfide, tungsten hexafluoride, vinyl acetylene, vinyl ether, and xenon.

The perfluorocarbons, as already indicated, are preferred for use as the gas or gaseous precursors, as well as additional stabilizing components. Included in such perfluorocarbon compositions are saturated perfluorocarbons, unsaturated perfluorocarbons, and cyclic perfluorocarbons. The saturated perfluorocarbons, which are usually preferred, have the formula $C_nF_{2n+2}$, where n is from 1 to 12, preferably 2 to 10, more preferably 4 to 8, and most preferably 5. Examples of suitable saturated perfluorocarbons are the following: tetrafluoromethane, hexafluoroethane, octafluoropropane, decafluorobutane, dodecafluoropentane, perfluorohexane, and perfluoroheptane. Cyclic perfluorocarbons, which have the formula $C_nF_{2n}$, where n is from 3 to 8, preferably 3 to 6, may also be preferred, and include, e.g., hexafluorocyclopropane, octafluorocyclobutane, and decafluorocyclopentane.

It is part of the present invention to optimize the utility of the microspheres by using gases of limited solubility. By limited solubility, is meant the ability of the gas to diffuse out of the microspheres by virtue of its solubility in the surrounding aqueous medium. A greater solubility in the aqueous medium imposes a gradient with the gas in the microsphere such that the gas will have a tendency to diffuse out of said microsphere. A lesser solubility in the aqueous milieu, will, on the other hand, decrease or eliminate the gradient between the microsphere and the interface such that the diffusion of the gas out of the microsphere will be impeded. Preferably, the gas entrapped in the microsphere has a solubility less than that of oxygen, i.e., 1 part gas in 32 parts water. See *Matheson Gas Data Book,* 1966, Matheson Company Inc. More preferably, the gas entrapped in the microsphere possesses a solubility in water less than that of air; and even more preferably, the gas entrapped in the microsphere possesses a solubility in water less than that of nitrogen.

Stabilizing Compounds

One or more stabilizing compounds are employed to form the microspheres, and to assure continued encapsulation of the gases or gaseous precursors. Even for relatively insoluble, non-diffusible gases such as perfluoropropane or sulfur hexafluoride, improved microsphere preparations are obtained when one or more stabilizing compounds are utilized in the formation of the gas and gaseous precursor filled microspheres. These compounds maintain the stability and the integrity of the microspheres with regard to their size, shape and/or other attributes.

The terms “stable” or “stabilized”, as used herein, means that the microspheres are substantially resistant to degradation, i.e., are resistant to the loss of microsphere structure or encapsulated gas or gaseous precursor for a useful period of time. Typically, the microspheres of the invention have a good shelf life, often retaining at least about 90 percent by volume of its original structure for a period of at least about two or three weeks under normal ambient conditions, although it is preferred that this period be at least a month, more at least preferably two months, even more preferably at least six months, still more preferably eighteen months, and most preferably three years. Thus, the gas and gaseous precursor filled microspheres typically have a good shelf life, sometimes even under adverse conditions, such as temperatures and pressures which are above or below those experienced under normal ambient conditions.

The stability of the microspheres of the present invention is attributable, at least in part, to the materials from which said microspheres are made, and it is often not necessary to employ additional stabilizing additives, although it is optional and often preferred to do so; and such additional stabilizing agents and their characteristics are explained in more detail herein. The materials from which the microspheres used in the present invention are constructed are preferably biocompatible lipid or polymer materials, and of these, the biocompatible lipids are especially preferred. In addition, because of the ease of formulation, i.e., the ability to produce the microspheres just prior to administration, these microspheres may be conveniently made on site.

The lipids and polymers employed in preparing the microspheres of the invention are biocompatible. By “biocompatible” is meant a lipid or polymer which, when introduced into the tissues of a human patient, will not result in any degree of unacceptable toxicity, including allergenic responses and disease states. Preferably the lipids or polymers are inert.

-Biocompatible Lipids

For the biocompatible lipid materials, it is preferred that such lipid materials be what is often referred to as "amphiphilic" in nature (i.e., polar lipid), by which is meant any composition of matter which has, on the one hand, lipophilic, i e., hydrophobic properties, while on the other hand, and at the same time, having lipophobic, i.e., hydrophilic properties.

Hydrophilic groups may be charged moieties or other groups having an affinity for water. Natural and synthetic phospholipids are examples of lipids useful in preparing the stabilized microspheres used in the present invention. They contain charged phosphate "ahead" groups which are hydrophilic, attached to long hydrocarbon tails, which are hydrophobic. This structure allows the phospholipids to achieve a single bilayer (unilamellar) arrangement in which all of the water-insoluble hydrocarbon tails are in contact with one another, leaving the highly charged phosphate head regions free to interact with a polar aqueous environment. It will be appreciated that a series of concentric bilayers are possible, i.e., oligolamellar and multilamellar, and such arrangements are also contemplated to be an aspect of the present invention. The ability to form such bilayer arrangements is one feature of the lipid materials useful in the present invention.

The lipid may alternatively be in the form of a monolayer, and the monolayer lipids may be used to form a single monolayer (unilamellar) arrangement. Alternatively, the monolayer lipid may be used to form a series of concentric monolayers, i.e., oligolamellar or multilamellar, and such arrangements are also considered to be within the scope of the invention.

It has also been found advantageous to achieving the stabilized microspheres of the present invention that they be prepared at a temperature below the gel to liquid crystalline phase transition temperature of a lipid used as the stabilizing compound. This phase transition temperature is the temperature at which a lipid bilayer will convert from a gel state to a liquid crystalline state. See, for example, Chapman et al., *J. Biol. Chem.* 1974 249, 2512–2521.

It is believed that, generally, the higher the gel state to liquid crystalline state phase transition temperature, the more impermeable the gas and gaseous precursor filled microspheres are at any given temperature. See Derek Marsh, *CRC Handbook of Lipid Bilayers* (CRC Press, Boca Raton, Fla. 1990), at p. 139 for main chain melting transitions of saturated diacyl-sn-glycero-3phosphocholines. The gel state to liquid crystalline state phase transition temperatures of various lipids will be readily apparent to those skilled in the art and are described, for example, in Gregoriadis, ed., *Liposome Technology*, Vol. I, 1–18 (CRC Press, 1984). The following table lists some of the representative lipids and their phase transition temperatures:

TABLE 2

Saturated Diacyl sn-Glycero(3)Phosphocholines:
Main Chain Phase Transition Temperatures

| Carbons in Acyl Chains | Main Phase Transition Temperature ° C. |
|---|---|
| 1,2-(12:0) | −1.0 |
| 1,2-(13:0) | 13.7 |
| 1,2-(14:0) | 23.5 |
| 1,2-(15:0) | 34.5 |
| 1,2-(16:0) | 41.4 |

TABLE 2-continued

Saturated Diacyl sn-Glycero(3)Phosphocholines:
Main Chain Phase Transition Temperatures

| Carbons in Acyl Chains | Main Phase Transition Temperature ° C. |
|---|---|
| 1,2-(17:0) | 48.2 |
| 1,2-(18:0) | 55.1 |
| 1,2-(19:0) | 61.8 |
| 1,2-(20:0) | 64.5 |
| 1,2-(21:0) | 71.1 |
| 1,2-(22:0) | 74.0 |
| 1,2-(23:0) | 79.5 |
| 1,2-(24:0) | 80.1 |

*Derek March, "CRC Handbook of Lipid Bilayers", CRC Press, Boca Raton, Florida (1990), page 139.

It has been found possible to enhance the stability of the microspheres used in the present invention by incorporating at least a small amount, i.e., about 1 to about 10 mole percent of the total lipid, of a negatively charged lipid into the lipid from which the gas and gaseous precursor filled microspheres are to be formed. Suitable negatively charged lipids include, e.g., phosphatidylserine, phosphatidic acid, and fatty acids. Such negatively charged lipids provide added stability by counteracting the tendency of the microspheres to rupture by fusing together, i.e., the negatively charged lipids tend to establish a uniform negatively charged layer on the outer surface of the microsphere, which will be repulsed by a similarly charged outer layer on the other microspheres. In this way, the microspheres will tend to be prevented from coming into touching proximity with each other, which would often lead to a rupture of the membrane or skin of the respective microspheres and consolidation of the contacting microspheres into a single, larger microsphere. A continuation of this process of consolidation will, of course, lead to significant degradation of the microspheres.

The lipid material or other stabilizing compound used to form the microspheres is also preferably flexible, by which is meant, in the context of gas and gaseous precursor filled microspheres, the ability of a structure to alter its shape, for example, in order to pass through an opening having a size smaller than the microsphere.

In selecting a lipid for preparing the stabilized microspheres used in the present invention, a wide variety of lipids will be found to be suitable for their construction. Particularly useful are any of the materials or combinations thereof known to those skilled in the art as suitable for liposome preparation. The lipids used may be of either natural, synthetic or semi-synthetic origin.

Lipids which may be used to prepare the gas and gaseous precursor filled microspheres used in the present invention include but are not limited to: lipids such as fatty acids, lysolipids, phosphatidylcholine with both saturated and unsaturated lipids including dioleoylphosphatidylcholine; dimyristoylphosphatidylcholine; dipentadecanoylphosphatidylcholine; dilauroylphosphatidylcholine; dipalmitoylphosphatidylcholine (DPPC); distearoylphosphatidylcholine (DSPC); phosphatidylethanolamines such as dioleoylphosphatidylethanolamine and dipalmitoylphosphatidylethanolamine (DPPE); phosphatidylserine; phosphatidylglycerol; phosphatidylinositol; sphingolipids such as sphingomyelin; glycolipids such as ganglioside GM1 and GM2; glucolipids; sulfatides; glycosphingolipids; phosphatidic acids such as dipalymitoylphosphatidic acid (DPPA); palmitic acid; stearic acid; arachidonic acid; oleic acid; lipids bearing polymers such as polyethyleneglycol, i.e., PEGylated lipids, chitin, hyaluronic acid or polyvinylpyrrolidone; lipids bearing sulfonated mono-, di-, oligo- or polysaccharides; cholesterol, cholesterol sulfate and cholesterol hemisuccinate; tocopherol hemisuccinate; lipids with ether and ester-linked fatty acids; polymerized lipids (a wide variety of which are well known in the art); diacetyl phosphate; dicetyl phosphate; stearylamine; cardiolipin; phospholipids with short chain fatty acids of 6–8 carbons in length; synthetic phospholipids with asymmetric acyl chains (e.g., with one acyl chain of 6 carbons and another acyl chain of 12 carbons); ceramides; non-ionic liposomes including niosomes such as polyoxyethylene fatty acid esters, polyoxyethylene fatty alcohols, polyoxyethylene fatty alcohol ethers, polyoxyethylated sorbitan fatty acid esters, glycerol polyethylene glycol oxystearate, glycerol polyethylene glycol ricinoleate, ethoxylated soybean sterols, ethoxylated castor oil, polyoxyethylene-polyoxypropylene polymers, and polyoxyethylene fatty acid stearates; sterol aliphatic acid esters including cholesterol sulfate, cholesterol butyrate, cholesterol iso-butyrate, cholesterol palmitate, cholesterol stearate, lanosterol acetate, ergosterol palmitate, and phytosterol n-butyrate; sterol esters of sugar acids including cholesterol glucuroneide, lanosterol glucuronide, 7-dehydrocholesterol glucuronide, ergosterol glucuronide, cholesterol gluconate, lanosterol gluconate, and ergosterol gluconate; esters of sugar acids and alcohols including lauryl glucuronide, stearoyl glucuronide, myristoyl glucuronide, lauryl gluconate, myristoyl gluconate, and stearoyl gluconate; esters of sugars and aliphatic acids including sucrose laurate, fructose laurate, sucrose palmitate, sucrose stearate, glucuronic acid, gluconic acid, accharic acid, and polyuronic acid; saponins including sarsasapogenin, smilagenin, hederagenin, oleanolic acid, and digitoxigenin; glycerol dilaurate, glycerol trilaurate, glycerol dipalmitate, glycerol and glycerol esters including glycerol tripalmitate, glycerol distearate, glycerol tristearate, glycerol dimyristate, glycerol trimyristate; longchain alcohols including n-decyl alcohol, lauryl alcohol, myristyl alcohol, cetyl alcohol, and n-octadecyl alcohol; 6-(5-cholesten-3β-yloxy)-1-thio-β-D-galactopyranoside; digalactosyldiglyceride; 6-(5-cholesten-3β-yloxy)hexyl-6-amino-6-deoxy-1-thio-β-D-galactopyranoside; 6-(5-cholesten-3β-yloxy)hexyl-6-amino-6-deoxy-1-thio-α-D-mannopyranoside; 12-(((7'-diethylaminocoumarin-3-yl)carbonyl)methylamino)-octadecanoic acid; N-[12-(((7'-diethylaminocoumarin-3-yl)carbonyl)methyl-amino) octadecanoyl]-2-aminopalmitic acid; cholesteryl)4'-trimethylammonio)butanoate; N-succinyldioleoylphosphatidylethanolamine; 1,2-dioleoyl-sn-glycerol; 1,2-dipalmitoyl-sn-3-succinylglycerol; 1,3-dipalmitoyl-2-succinylglycerol; 1-hexadecyl-2-palmitoyl-glycerophosphoethanolamine and palmitoylhomocysteine, and/or combinations thereof.

If desired, a variety of cationic lipids such as DOTMA, N-[1-(2,3-dioleoyloxy)propyl]-N,N,N-trimethylammoium chloride; DOTAP, 1,2-dioleoyloxy-3-(trimethylammonio) propane; and DOTB, 1,2-dioleoyl-3-(4'-trimethyl-ammonio) butanoyl-sn-glycerol may be used. In general the molar ratio of cationic lipid to non-cationic lipid in the liposome may be, for example, 1:1000, 1:100, preferably, between 2:1 to 1:10, more preferably in the range between 1:1 to 1:2.5 and most preferably 1:1 (ratio of mole amount cationic lipid to mole amount non-cationic lipid, e.g., DPPC). A wide variety of lipids may comprise the non-cationic lipid when cationic lipid is used to construct the microsphere. Preferably, this non-cationic lipid is dipalmitoylphosphatidylcholine, dipalmitoylphosphatidylethanolamine or dioleoylphosphatidylethanolamine. In lieu of cationic lipids as described above, lipids bearing cationic polymers such as polylysine or polyarginine, as well as alkyl phosphonates, alkyl phosphinates, and alkyl phosphites, may also be used to construct the microspheres.

The most preferred lipids are phospholipids, preferably DPPC, DPPE, DPPA and DSPC, and most preferably DPPC.

In addition, examples of saturated and unsaturated fatty acids that may be used to prepare the stabilized microspheres used in the present invention, in the form of gas and gaseous precursor filled mixed micelles, may include molecules that may contain preferably between 12 carbon atoms and 22 carbon atoms in either linear or branched form. Hydrocarbon groups consisting of isoprenoid units and/or prenyl groups can be used as well. Examples of saturated fatty acids that are suitable include, but are not limited to, lauric, myristic, palmitic, and stearic acids; examples of unsaturated fatty acids that may be used are, but are not limited to, lauroleic, physeteric, myristoleic, palmitoleic, petroselinic, and oleic acids; examples of branched fatty acids that may be used are, but are not limited to, isolauric, isomyristic, isopalmitic, and isostearic acids. In addition, to the saturated and unsaturated groups, gas and gaseous precursor filled mixed micelles can also be composed of 5 carbon isoprenoid and prenyl groups.

-Biocompatible Polymers

The biocompatible polymers useful as stabilizing compounds for preparing the gas and gaseous precursor filled microspheres used in the present invention can be of either natural, semi-synthetic (modified natural) or synthetic origin. As used herein, the term polymer denotes a compound comprised of two or more repeating monomeric units, and preferably 10 or more repeating monomeric units. The phrase semi-synthetic polymer (or modified natural polymer), as employed herein, denotes a natural polymer that has been chemically modified in some fashion. Exemplary natural polymers suitable for use in the present invention include naturally occurring polysaccharides. Such polysaccharides include, for example, arabinans, fructans, fucans, galactans, galacturonans, glucans, mannans, xylans (such as, for example, inulin), levan, fucoidan, carrageenan, galatocarolose, pectic acid, pectin, amylose, pullulan, glycogen, amylopectin, cellulose, dextran, pustulan, chitin, agarose, keratan, chondroitan, dermatan, hyaluronic acid, alginic acid, xanthan gum, starch and various other natural homopolymer or heteropolymers such as those containing one or more of the following aldoses, ketoses, acids or amines: erythrose, threose, ribose, arabinose, xylose, lyxose, allose, altrose, glucose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Exemplary semi-synthetic polymers include carboxymethylcellulose, hydroxymethylcellulose, hydroxypropylmethylcellulose, methylcellulose, and methoxycellulose. Exemplary synthetic polymers suitable for use in the present invention include polyethylenes (such as, for example, polyethylene glycol, polyoxyethylene, and polyethylene terephthlate), polypropylenes (such as, for example, polypropylene glycol), polyurethanes (such as, for example, polyvinyl alcohol (PVA), polyvinylchloride and polyvinylpyrrolidone), polyamides including nylon, polystyrene, polylactic acids, fluorinated hydrocarbons, fluorinated carbons (such as, for example, polytetrafluoroethylene), and polymethylmethacrylate, and derivatives thereof. Methods for the preparation of such polymer-based microspheres will be readily apparent to those skilled in the art, once armed with the present disclosure, when the present disclosure is coupled with information known in the art, such as that described and referred to in Unger, U.S. Pat. No. 5,205,290, the disclosures of which are hereby incorporated herein by reference, in their entirety.

Preferably, when intended to be used in the gastrointestinal tract, the polymer employed is one which has a relatively high water binding capacity. When used, for example, in the gastrointestinal region, a polymer with a high water binding capacity binds a large amount of free water, enabling the polymer to carry a large volume of liquid through the gastrointestinal tract, thereby filling and distending the tract. The filled and distended gastrointestinal tract permits a clearer picture of the region. In addition, where imaging of the gastrointestinal region is desired, preferably the polymer employed is also one which is not substantially degraded within and absorbed from the gastrointestinal region. Minimization of metabolism and absorption within the gastrointestinal tract is preferable, so as to avoid the removal of the contrast agent from the tract as well as avoid the formation of gas within the tract as a result of this degradation. Moreover, particularly where gastrointestinal usage is contemplated, polymers are preferably such that they are capable of displacing air and minimizing the formation of large air bubbles within the polymer composition.

Particularly preferred embodiments of the present invention include microspheres wherein the stabilizing compound from which the stabilized gas and gaseous precursor filled microspheres are formed comprises three components, (1) a neutral (e.g., nonionic or zwitterionic) lipid, (2) a negatively charged lipid, and (3) a lipid bearing a hydrophilic polymer. Preferably, the amount of said negatively charged lipid will be greater than 1 mole percent of total lipid present, and the amount of lipid bearing a hydrophilic polymer will be greater than 1 mole percent of total lipid present. It is also preferred that said negatively charged lipid be a phosphatidic acid. The lipid bearing a hydrophilic polymer will desirably be a lipid covalently bound to said polymer, and said polymer will preferably have a weight average molecular weight of from about 400 to about 100,000. Said hydrophilic polymer is preferably selected from the group consisting of polyethyleneglycol, polypropyleneglycol, polyvinylalcohol, and polyvinylpyrrolidone and copolymers thereof. The PEG or other polymer may be bound to the DPPE or other lipid through a covalent linkage, such as through an amide, carbamate or amine linkage. Alternatively, ester, ether, thioester, thioamide or disulfide (thioester) linkages may be used with the PEG or other polymer to bind the polymer to, for example, cholesterol or other phospholipids. Where the hydrophilic polymer is polyethyleneglycol, a lipid bearing such a polymer will be said to be "PEGylated", which has reference to the abbreviation for polyethyleneglycol: "PEG". Said lipid bearing a hydrophilic polymer is preferably dipalmitoylphosphatidylethanolamine-polyethyleneglycol 5000, i.e., a dipalmitoylphosphatidylethanolamine lipid having a polyethyleneglycol polymer of a mean weight average molecular weight of about 5000 attached thereto (DPPE-PEG5000); or distearoyl-phosphatidylethanolamine-polyethyleneglycol 5000.

Preferred embodiments of the microsphere contemplated by the present invention would include, e.g., 77.5 mole percent dipalmitoylphophatidylcholine (DPPC), with 12.5 mole percent of dipalmitoylphosphatidic acid (DPPA), and with 10 mole percent of dipalmitoylphosphatidylethanolamine-polyethyleneglycol-5000 (DPPE/PEG5000). These compositions in a 82/10/8 ratio of mole percentages, respectively, is also preferred. The DPPC component is effectively neutral, since the phosphtidyl portion is negatively charged and the choline portion is positively charged. Consequently, the DPPA component, which is negatively charged, is added to enhance stabilization in accordance with the mechanism described further above regarding negatively charged lipids as an additional agent. The third component, DPPE/PEG, provides a PEGylated material bound to the lipid membrane or skin of the microsphere by the DPPE moiety, with the PEG moiety free to surround the microsphere membrane or skin, and thereby form a physical barrier to various enzymatic and other endogenous agents in the body whose function is to degrade such foreign materials. It is also theorized that the PEGylated material, because of its structural similarity to water, is able to defeat the action of the macrophages of the human immune system, which would otherwise tend to surround and remove the foreign object. The result is an increase in the time during which the stabilized microspheres can function as MRI contrast media.

Other and Auxiliary Stabilizing Compounds

It is also contemplated to be a part of the present invention to prepare stabilized gas and gaseous precursor filled microspheres using compositions of matter in addition to the biocompatible lipids and polymers described above, provided that the microspheres so prepared meet the stability and other criteria set forth herein. These compositions may be basic and fundamental, i.e., form the primary basis for creating or establishing the stabilized gas and gaseous precursor filled microspheres. On the other hand, they may be auxiliary, i.e., act as subsidiary or supplementary agents which either enhance the functioning of the basic stabilizing compound or compounds, or else contribute some desired property in addition to that afforded by the basic stabilizing compound.

However, it is not always possible to determine whether a given compound is a basic or an auxiliary agent, since the functioning of the compound in question is determined empirically, i.e., by the results produced with respect to producing stabilized microspheres. As examples of how these basic and auxiliary compounds may function, it has been observed that the simple combination of a biocompatible lipid and water or saline when shaken will often give a cloudy solution subsequent to autoclaving for sterilization. Such a cloudy solution may function a contrast agent, but is aesthetically objectionable and may imply instability in the form of undissolved or undispersed lipid particles. Thus, propylene glycol may be added to remove this cloudiness by facilitating dispersion or dissolution of the lipid particles. The propylene glycol may also function as a thickening agent which improves microsphere formation and stabilization by increasing the surface tension on the microsphere membrane or skin. It is possible that the propylene glycol further functions as an additional layer that coats the membrane or skin of the microsphere, thus providing additional stabilization. As examples of such further basic or auxiliary stabilizing compounds, there are conventional surfactants which may be used; see D'Arrigo U.S. Pat. Nos. 4,684,479 and 5,215,680.

Additional auxiliary and basic stabilizing compounds include such agents as peanut oil, canola oil, olive oil, safflower oil, corn oil, or any other oil commonly known to be ingestible which is suitable for use as a stabilizing compound in accordance with the requirements and instructions set forth in the instant specification.

In addition, compounds used to make mixed micelle systems may be suitable for use as basic or auxiliary stabilizing compounds, and these include, but are not limited to: lauryltrimethylammonium bromide (dodecyl-), cetyltrimethylammonium bromide (hexadecyl-), myristyltrimethylammonium bromide (tetradecyl-), alkyldimethylbenzylammonium chloride (alkyl=$C_{12}$, $C_{14}$, $C_{16}$,), benzyldimethyldodecylammonium bromide/chloride, benzyldimethyl hexadecylammonium bromide/chloride, benzyldimethyl tetradecylammonium bromide/chloride, cetyldimethylethylammonium bromide/chloride, or cetylpyridinium bromide/chloride.

It has been found that the gas and gaseous precursor filled microspheres used in the present invention may be controlled according to size, solubility and heat stability by choosing from among the various additional or auxiliary stabilizing agents described herein. These agents can affect these parameters of the microspheres not only by their physical interaction with the lipid coatings, but also by their ability to modify the viscosity and surface tension of the surface of the gas and gaseous precursor filled microsphere. Accordingly, the gas and gaseous precursor filled microspheres used in the present invention may be favorably modified and further stabilized, for example, by the addition of one or more of a wide variety of (a) viscosity modifiers, including, but not limited to carbohydrates and their phosphorylated and sulfonated derivatives; and polyethers, preferably with molecular weight ranges between 400 and 100,000; di- and trihydroxy alkanes and their polymers, preferably with molecular weight ranges between 200 and 50,000; (b) emulsifying and/or solubilizing agents may also be used in conjunction with the lipids to achieve desired modifications and further stabilization; such agents include, but are not limited to, acacia, cholesterol, diethanolamine, glyceryl monostearate, lanolin alcohols, lecithin, mono- and di-glycerides, mono-ethanolamine, oleic acid, oleyl alcohol, poloxamer (e.g., poloxamer 188, poloxamer 184, and poloxamer 181), polyoxyethylene 50 stearate, polyoxyl 35 castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan mono-laurate, sorbitan mono-oleate, sorbitan mono-palmitate, sorbitan monostearate, stearic acid, trolamine, and emulsifying wax; (c) suspending and/or viscosity-increasing agents that may be used with the lipids include, but are not limited to, acacia, agar, alginic acid, aluminum mono-stearate, bentonite, magma, carbomer 934P, carboxymethylcellulose, calcium and sodium and sodium 12, carrageenan, cellulose, dextran, gelatin, guar gum, locust bean gum, veegum, hydroxyethyl cellulose, hydroxypropyl methylcellulose, magnesium-aluminum-silicate, methylcellulose, pectin, polyethylene oxide, povidone, propylene glycol alginate, silicon dioxide, sodium alginate, tragacanth, xanthum gum, α-d-gluconolactone, glycerol and mannitol; (d) synthetic suspending agents may also be utilized such as polyethyleneglycol (PEG), polyvinylpyrrolidone (PVP), polyvinylalcohol (PVA), polypropylene glycol, and polysorbate; and (e) tonicity raising agents may be included; such agents include but are not limited to sorbitol, propyleneglycol and glycerol.

Aqueous Diluents

As mentioned earlier, where the microspheres are lipid in nature, a particularly desired component of the stabilized microspheres is an aqueous environment of some kind, which induces the lipid, because of its hydrophobic/hydrophilic nature, to form microspheres, the most stable configuration which it can achieve in such an environment. The diluents which can be employed to create such an aqueous environment include, but are not limited to water, either deionized or containing any number of dissolved salts, etc., which will not interfere with creation and maintenance of the stabilized microspheres or their use as MRI contrast agents; and normal saline and physiological saline.

Paramagnetic and Superparamagnetic Contrast Agents

In a further embodiment of the present invention, the stabilized gas filled microsphere based contrast medium of the invention may further comprise additional contrast agents such as conventional contrast agents, which may serve to increase the efficacy of the contrast medium for MRI. Many such contrast agents are well known to those skilled in the art and include paramagnetic and superparamagnetic contrast agents.

Exemplary paramagnetic contrast agents suitable for use in the subject invention include stable free radicals (such as, for example, stable nitroxides), as well as compounds comprising transition, lanthanide and actinide elements, which may, if desired, be in the form of a salt or may be covalently or noncovalently bound to complexing agents (including lipophilic derivatives thereof) or to proteinaceous macromolecules.

Preferable transition, lanthanide and actinide elements include Gd(III), Mn(II), Cu(II), Cr(III), Fe(II), Fe(III), Co(II), Er(II), Ni(II), Eu(III) and Dy(III). More preferably, the elements include Gd(III), Mn(II), Cu(II), Fe(II), Fe(III), Eu(III) and Dy(III), especially Mn(II) and Gd(III).

These elements may, if desired, be in the form of a salt, such as a manganese salt, e.g., manganese chloride, manganese carbonate, manganese acetate, and organic salts of manganese such as manganese gluconate and manganese hydroxylapatite; and such as an iron salt, e.g., iron sulfides and ferric salts such as ferric chloride.

These elements may also, if desired, be bound, e.g., covalently or noncovalently, to complexing agents (including lipophilic derivatives thereof) or to proteinaceous macromolecules. Preferable complexing agents include, for example, diethylenetriamine-pentaacetic acid (DTPA), ethylene-diaminetetraacetic acid (EDTA), 1,4,7,10-tetraazacyclododecane-N,N',N',N'''-tetraacetic acid (DOTA), 1,4,7,10-tetraazacyclododecane-N,N',N''-triacetic acid (DO3A), 3,6,9-triaza-12-oxa-3,6,9-tricarboxymethylene-10-carboxy-13-phenyl-tridecanoic acid (B-19036), hydroxybenzylethylene-diamine diacetic acid (HBED), N,N'-bis(pyridoxyl-5-phosphate)ethylene diamine, N,N'-diacetate (DPDP), 1,4,7-triazacyclononane-N,N',N''-triacetic acid (NOTA), 1,4,8,11-tetraazacyclotetradecane-N,N'N'',N'''-tetraacetic acid (TETA), kryptands (that is, macrocyclic complexes), and desferrioxamine. More preferably, the complexing agents are EDTA, DTPA, DOTA, DO3A and kryptands, most preferably DTPA. Preferable lipophilic complexes thereof include alkylated derivatives of the complexing agents EDTA, DOTA, etc., for example, EDTA-DDP, that is, N,N'-bis-(carboxy-decylamidomethyl-N-2,3-dihydroxypropyl) ethylenediamine-N,N'-diacetate; EDTA-ODP, that is N,N'-bis(carboxy-octadecylamido-methyl-N-2,3-dihydroxypropyl)ethylenediamine-N,N'-diacetate; EDTA-LDP N,N'-Bis-(carboxylaurylamidomethyl-N-2,3-dihydroxypropyl)-ethylenediamine-N,N'-diacetate; etc.; such as those described in U.S. Ser. No. 887,290, filed May 22, 1992, the disclosures of which are hereby incorporated herein by reference in its entirety. Preferable proteinaceous macromolecules include albumin, collagen, polyarginine, polylysine, polyhistidine, γ-globulin and β-globulin. More preferably, the proteinaceous macromolecules comprise albumin, polyarginine, polylysine, and polyhistidine.

Suitable complexes thus include Mn(II)-DTPA, Mn(II)-EDTA, Mn(II)-DOTA, Mn(II)-DO3A, Mn(II)-kryptands, Gd(III)-DTPA, Gd(III)-DOTA, Gd(III)-DO3A, Gd(III)-kryptands, Cr(III)-EDTA, Cu(II)-EDTA, or iron-desferrioxamine, especially Mn(II)-DTPA or Gd(III)-DTPA.

Nitroxides are paramagnetic contrast agents which increase both T1 and T2 relaxation rates by virtue of one unpaired electron in the nitroxide molecule. The paramagnetic effectiveness of a given compound as an MRI contrast agent is at least partly related to the number of unpaired electrons in the paragmagnetic nucleus or molecule, specifically to the square of the number of unpaired electrons. For example, gadolinium has seven unpaired electrons and a nitroxide molecule has only one unpaired electron; thus gadolinium is generally a much stronger MRI contrast agent than a nitroxide. However, effective correlation time, another important parameter for assessing the effectiveness of contrast agents, confers potential increased relaxivity to the nitroxides. When the effective correlation time is very close to the proton Larmour frequency, the relaxation rate may increase dramatically. When the tumbling rate is slowed, e.g., by attaching the paramagnetic contrast agent to a large structure, it will tumble more slowly and thereby more effectively transfer energy to hasten relaxation of the water protons. In gadolinium, however, the electron spin relaxation time is rapid and will limit the extent to which slow rotational correlation times can increase relaxivity. For nitroxides, however, the electron spin correlation times are more favorable and tremendous increases in relaxivity may be attained by slowing the rotational correlation time of these molecules. The gas filled microspheres of the present invention are ideal for attaining the goals of slowed rotational correlation times and resultant improvement in relaxivity. Although not intending to be bound by any particular theory of operation, it is contemplated that since the nitroxides may be designed to coat the perimeters of the gas filled microspheres, e.g., by making alkyl derivatives thereof, that the resulting correlation times can be optimized. Moreover, the resulting contrast medium of the present invention may be viewed as a magnetic sphere, a geometric configuration which maximizes relaxivity.

If desired, the nitroxides may be alkylated or otherwise derivitized, such as the nitroxides 2,2,5,5-tetramethyl-1-pyrrolidinyloxy, free radical, and 2,2,6,6-tetramethyl-1-piperidinyloxy, free radical (TMPO), Exemplary superparamagnetic contrast agents suitable for use in the subject invention include metal oxides and sulfides which experience a magnetic domain, ferro- or ferrimagnetic compounds, such as pure iron, magnetic iron oxide (such as magnetite), γ-$Fe_2O_3$, manganese ferrite, cobalt ferrite and nickel ferrite.

The contrast agents, such as the paramagnetic and superparamagnetic contrast agents described above, may be employed as a component within the microspheres or in the contrast medium comprising the microspheres. They may be entrapped within the internal space of the microspheres, administered as a solution with the microspheres or incorporated into the stabilizing compound forming the microsphere wall.

For example, if desired, the paramagnetic or superparamagnetic agents may be delivered as alkylated or other derivatives incorporated into the stabilizing compound, especially the lipidic walls of the microspheres. In particular, the nitroxides 2,2,5,5-tetramethyl-1-pyrrolidinyloxy, free radical and 2,2,6,6-tetramethyl-1-piperidinyloxy, free radical, can form adducts with long chain fatty acids at the positions of the ring which are not occupied by the methyl groups, via a number of different linkages, e.g., an acetyloxy group. Such adducts are very amenable to incorporation into the stabilizing compounds, especially those of a lipidic nature, which form the walls of the microspheres of the present invention.

Mixtures of any one or more of the paramagnetic agents and/or superparamagnetic agents in the contrast media may similarly be used.

The paramagnetic and superparamagnetic agents described above may also be coadministered separately, if desired.

The gas filled microspheres used in the present invention may not only serve as effective carriers of the superparamagnetic agents, e.g., iron oxides, but also appear to magnify the effect of the susceptibility contrast agents. Superparamagnetic contrast agents include metal oxides, particularly iron oxides but including manganese oxides, and as iron oxides, containing varying amounts of manganese, cobalt and nickel which experience a magnetic domain. These agents are nano or microparticles and have very high bulk susceptibilities and transverse relaxation rates. The larger particles, e.g., 100 nm diameter, have much higher R2 relaxivities than R1 relaxivities but the smaller particles, e.g., 10 to 15 nm diameter have somewhat lower R2 relaxivities, but much more balanced R1 nd R2 values. The smallest particles, e.g., monocrystalline iron oxide particles, 3 to 5 nm in diameter, have lower R2 relaxivities, but probably the most balanced R1 and R2 relaxation rates. Ferritin can also be formulated to encapsulate a core of very high relaxation rate superparamagnetic iron. It has been discovered that stabilized gas filled microspheres used in the present invention can increase the efficacy and safety of these conventional iron oxide based MRI contrast agents.

The iron oxides may simply be incorporated into the stabilizing compounds from which the microspheres are made. Particularly, the iron oxides may be incorporated into the walls of the lipid based microspheres, e.g., adsorbed onto the surfaces of the microspheres, or entrapped within the interior of the microspheres as described in U.S. Pat. No. 5,088,499, issued Feb. 18, 1992. Although there is no intention to limit the present invention to any particular theory as to its mode of action, it is believed that the microspheres increase the efficacy of the superparamagnetic contrast agents by several mechanisms. First, it is believed that the microspheres function so as to increase the apparent magnetic concentration of the iron oxide particles. Second, it is believed that the microspheres increase the apparent rotational correlation time of the MRI contrast agents, both paramagnetic and superparamagnetic agents, so that relaxation rates are increased. Finally, the microspheres appear to operate by way of a novel mechanism which increases the apparent magnetic domain of the contrast medium and is believed to operate in the manner described immediately below.

The microspheres may be thought of as flexible spherical domains of differing susceptibility from the suspending medium, i.e., the aqueous suspension of the contrast medium and the gastrointestinal fluids in the case of gastrointestinal administration, and blood or other body fluids in the cases of intravascular injection or injection into another body space. When considering ferrites or iron oxide particles, it should be noted that these agents have a particle size dependent effect on contrast, i.e., it depends on the particle diameter of the iron oxide particle. This phenomenon is very common and is often referred to as the "secular" relaxation of the water molecules. Described in more physical terms, this relaxation mechanism is dependent upon the effective size of the molecular complex in which a paramagnetic atom, or paramagnetic molecule, or molecules, may reside. One physical explanation may be described in the following Solomon-Bloembergen equations which define the paramagnetic contributions to the $T_1$ and $T_2$ relaxation times of a spin ½ nucleus with gyromagnetic ratio g perturbed by a paramagnetic ion:

$$1/T_1M = (2/15)\ S(S+1)\ y^2 g^2 \beta^2/r^6 [3\tau_c/(1+\omega_I^{2+sc\ T_c^2}) + 7\tau_c/(1+\omega_s^{2+sc} T_c^2)] + (2/3)\ S(S+1)A^2/h^2\ [\tau_e/(1+\omega_s 2\tau_e^2)]$$

and $$1/T_2M = (1/15)\ S(S+1)\ y^2 g^2 \beta^2/r^6 [4\tau_c + 3\tau_c/(1+\omega_I^{2+sc\ T_c^2}) + 13\tau_c/(1+w_s^{2+sc\ T_c^2})] + (1/3)\ S(S+1)A^2/h^2 [\tau_e/(1+\omega_s 2\tau_e^2)]$$

where:
S=electron spin quantum number;
g=electronic g factor;
β=Bohr magneton;
$\omega_I$ and $\omega_s$ (=657 $w_I$)=Larmor angular precession frequencies for the nuclear spins and electron spins;
r=ion-nucleus distance;
A=hyperfine coupling constant;
$\tau_c$ and $\tau_e$=correlation times for the dipolar and scalar interactions, respectively; and
h=Planck's constant See, e.g., Solomon, I. *Phys. Rev.* 99, 559 (1955) and Bloembergen, N. *J. Chem. Phys.* 27, 572, 595 (1957)

A few large particles will generally have a much greater effect than a larger number of much smaller particles, primarily due to a larger correlation time. If one were to make the iron oxide particles very large however, they might be toxic and embolize the lungs or activate the complement cascade system. Furthermore, it is not the total size of the particle that matters, but particularly the diameter of the particle at its edge or outer surface. The domain of magnetization or susceptibility effect falls off exponentially from the surface of the particle. Generally speaking, in the case of dipolar (through space) relaxation mechanisms, this exponential fall off exhibits an $r^6$ dependence. Literally interpreted, a water molecule that is 4 angstroms away from a paramagnetic surface will be influenced 64 times less than a water molecule that is 2 angstroms away from the same paramagnetic surface. The ideal situation in terms of maximizing the contrast effect would be to make the iron oxide particles hollow, flexible and as large as possible. Up until now it has not been possible to do this; furthermore, these benefits have probably been unrecognized until now. By coating the inner or outer surfaces of the microspheres with the contrast agents, even though the individual contrast agents, e.g., iron oxide nanoparticles or paramagnetic ions, are relatively small structures, the effectiveness of the contrast agents may be greatly enhanced. In so doing, the contrast agents may function as an effectively much larger sphere wherein the effective domain of magnetization is determined by the diameter of the microsphere and is maximal at the surface of the microsphere. These agents afford the advantage of flexibility, i.e., compliance. While rigid microspheres might lodge in the lungs or other organs and cause toxic reactions, these flexible microspheres slide through the capillaries much more easily.

Furthermore, the microsphere based contrast media of the present invention can be used to measure pressures non-invasively by NMR in vivo. As noted above, the magnetic domain depends upon the diameter of the microspheres. As the microspheres encounter regions of higher pressure in vivo, due to their flexibility, they decrease in diameter and relaxivity then decreases. By measuring $1/T2^*$ (the effect on the non-refocused relaxation rate) or signal intensity one can then infer the effects on pressure non-invasivley in vivo.

Specifically, as shown in the accompanying figures, these magnetically active microspheres may be used for estimating pressure by magnetic resonance imaging. The microspheres increase the bulk susceptibility and accordingly increase $T_2$ relaxation but even more so for $T_2^*$ relaxation. Because the effects of static field gradients are mainly compensated in spin echo experiments (by virtue of the 180° Radiofrequency refocusing pulse) the effect of the bubbles is less marked on $T_2$ than $T_2^*$ weighted pulse sequences where static field effects are not compensated. Increasing pressure results in loss of microsphere or microsphere disruption (for more soluble gases) as well as a decrease in microsphere diameter. Accordingly $1/T_2$ decreases with increasing pressure. After release of pressure some of the remaining microspheres reexpand and $1/T_2$ increases again slightly. Microspheres composed of about 80% PFP with 20% air show enhanced stability and a slight fall in $1/T_2$ with pressure which returns to baseline after release of pressure (i.e., the micropheres are stable but show a slight $1/T_2$ pressure). When gradient echo images are obtained and signal intensity measured these effects are much more marked. Signal intensity increases with increasing pressure ($1/T_2^*$ decreases with increased pressure). Because the experiment is performed relatively quickly (it takes less than a tenth the time to perform the gradient echo images than to measure $T_2$). The duration of exposure to pressure is much less and the nitrogen microspheres return nearly to baseline after pressure release (i.e. there is very little loss of microspheres). Accordingly the signal intensity on gradient echo falls back nearly to baseline at return to ambient pressure. Thus, for measurement of pressure by MRI or ultrasound the bubbles can either be designed to fall apart with increasing pressure or to be stable but decrease bubble diameter with increasing pressure. Because an MRI bubble radius affects $1/T_2^*$, this relationship can be used to estimate pressure by MRI.

Thus the present invention further provides a method for determining the pressure in localized tissue of a patient comprising administering to the localized tissue gas filled microspheres, scanning said localized tissue using magnetic resonance imaging to ascertain 1/T2, 1/T2* or signal intensity values, and comparing said 1/T2, 1/T2* or signal intensity values to other known 1/T2, 1/T2* or signal intensity values to estimate the pressure in said localized tissue. The known 1/T2, 1/T2*, or signal intensity values may be a preadministration (prior to administration to the patient) 1/T2, 1/T2*, or signal intensity value taken at a known pressure, temperature and/or microsphere radius, or may be a 1/T2, 1/T2* or signal intensity value taken at another localized tissue of a patient Thus, after a comparison of the 1/T2, 1/T2* or signal intensity values, a pressure estimate may be made of the absolute pressure in the localized tissue of interest, or of a change in pressure between the localized tissue of interest and another localized tissue.

Similarly, as one skilled in the art would recognize, once armed with the present disclosure, the foregoing process for measuring pressure may also be advantageously employed in determining the temperature in localized tissue of a patient. Thus, the present invention additionally provides a method for determining the temperature in localized tissue of a patient comprising administering to the localized tissue gas filled microspheres, scanning said localized tissue using magnetic resonance imaging to ascertain $1/T2$, $1/T2^*$ or signal intensity values, and comparing said $1/T2$, $1/T2^*$ or signal intensity values to other known $1/T2$, $1/T2^*$ or signal intensity values to estimate the temperature in said localized tissue.

Methods of Preparation

The stabilized gas filled microspheres used in the present invention may be prepared by a number of suitable methods. These are described below separately for the case where the microspheres are gas filled, and where they are gaseous precursor filled, although microspheres having both a gas and gaseous precursor are part of the present invention.

-Utilizing a Gas

A preferred embodiment comprises the steps of agitating an aqueous solution comprising a stabilizing compound, preferably a lipid, in the presence of a gas at a temperature below the gel to liquid crystalline phase transition temperature of the lipid to form gas filled microspheres. The term agitating, and variations thereof, as used herein, means any motion that shakes an aqueous solution such that gas is introduced from the local ambient environment into the aqueous solution. The shaking must be of sufficient force to result in the formation of microspheres, particularily stabilized microspheres. The shaking may be by swirling, such as by vortexing, side-to-side, or up-and-down motion. Different types of motion may be combined. Also, the shaking may occur by shaking the container holding the aqueous lipid solution, or by shaking the aqueous solution within the container without shaking the container itself.

Further, the shaking may occur manually or by machine. Mechanical shakers that may be used include, for example, a shaker table such as a VWR Scientific (Cerritos, Calif.) shaker table, or a Wig-L-Bug® Shaker from Crescent Dental Mfg. Ltd., Lyons, Ill., which has been found to give excellent results. It is a preferred embodiment of the present invention that certain modes of shaking or vortexing be used to make stable microspheres within a preferred size range. Shaking is preferred, and it is preferred that this shaking be carried out using the Wig-L-Bug® mechanical shaker. In accordance with this preferred method, it is preferred that a reciprocating motion be utilized to generate the gas filled microspheres. It is even more preferred that the motion be reciprocating in the form of an arc. It is still more preferred that the motion be reciprocating in the form of an arc between about 2° and about 20°, and yet further preferred that the arc be between about 5° and about 8°. It is most preferred that the motion is reciprocating between about 6° and about 7°, most particularly about 6.5°. It is contemplated that the rate of reciprocation, as well as the arc thereof, is critical to determining the amount and size of the gas filled microspheres formed. It is a preferred embodiment of the present invention that the number of reciprocations, i.e., full cycle oscillations, be within the range of about 1000 and about 20,000 per minute. More preferably, the number of reciprocations or oscillations will be between 2500 and 8000. The Wig-L-Bug®, referred to above, is a mechanical shaker which provides 2000 pestle strikes every 10 seconds, i.e., 6000 oscillations every minute. Of course, the number of oscillations is dependent upon the mass of the contents being agitated, with the larger the mass, the fewer the number of oscillations). Another means for producing shaking includes the action of gas emitted under high velocity or pressure.

It will also be understood that preferably, with a larger volume of aqueous solution, the total amount of force will be correspondingly increased. Vigorous shaking is defined as at least about 60 shaking motions per minute, and is preferred. Vortexing at least 60–300 revolutions per minute is more preferred. Vortexing at 300–1800 revolutions per minute is most preferred. The formation of gas filled microspheres upon shaking can be detected visually. The concentration of lipid required to form a desired stabilized microsphere level will vary depending upon the type of lipid used, and may be readily determined by routine experimentation. For example, in preferred embodiments, the concentration of 1,2-dipalimitoyl-phosphatidylcholine (DPPC) used to form stabilized microspheres according to the methods of the present invention is about 0.1 mg/ml to about 30 mg/ml of saline solution, more preferably from about 0.5 mg/ml to about 20 mg/ml of saline solution, and most preferably from about 1 mg/ml to about 10 mg/ml of saline solution. The concentration of distearoylphosphatidylcholine (DSPC) used in preferred embodiments is about 0.1 mg/ml to about 30 mg/ml of saline solution, more preferably from about 0.5 mg/ml to about 20 mg/ml of saline solution, and most preferably from about 1 mg/ml to about 10 mg/ml of saline solution.

In addition to the simple shaking methods described above, more elaborate, but for that reason less preferred, methods can also be employed, e.g., liquid crystalline shaking gas instillation processes, and vacuum drying gas instillation processes, such as those described in U.S. Ser. No. 076,250, filed Jun. 11, 1993, which is incorporated herein by reference, in its entirety. When such processes are used, the stabilized microspheres which are to be gas filled, may be prepared prior to gas installation using any one of a variety of conventional liposome preparatory techniques which will be apparent to those skilled in the art. These techniques include freeze-thaw, as well as techniques such as sonication, chelate dialysis, homogenization, solvent infusion, microemulsification, spontaneous formation, solvent vaporization, French pressure cell technique, controlled detergent dialysis, and others, each involving preparing the microspheres in various fashions in a solution containing the desired active ingredient so that the therapeutic, cosmetic or other agent is encapsulated in, enmeshed in, or attached the resultant polar-lipid based microsphere. See, e.g., Madden et al, *Chemistry and Physics of Lipids,* 1990 53, 37–46, the disclosure of which is hereby incorporated herein by reference in its entirety.

The gas filled microspheres prepared in accordance with the methods described above range in size from below a micron to over 100µ in size. In addition, it will be noted that after the extrusion and sterilization procedures, the agitation or shaking step yields gas filled microspheres with little to no residual anhydrous lipid phase (Bangham, A. D., Standish, M. M, & Watkins, J. C. (1965) *J. Mol. Biol.* 13, 238–252) present in the remainder of the solution. The resulting gas filled microspheres remain stable on storage at room temperature for a year or even longer.

The size of gas filled microspheres can be adjusted, if desired, by a variety of procedures including microemulsification, vortexing, extrusion, filtration, sonication, homogenization, repeated freezing and thawing cycles, extrusion under pressure through pores of defined size, and similar methods. It may also be desirable to use the microspheres of the present invention as they are formed, without any attempt at further modification of the size thereof.

The gas filled microspheres may be sized by a simple process of extrusion through filters; the filter pore sizes control the size distribution of the resulting gas filled microspheres. By using two or more cascaded, i.e., a stacked set of filters, e.g., 10μ followed by 8μ, the gas filled microspheres have a very narrow size distribution centered around 7–9 μm. After filtration, these stabilized gas filled microspheres remain stable for over 24 hours.

The sizing or filtration step may be accomplished by the use of a filter assembly when the suspension is removed from a sterile vial prior to use, or even more preferably, the filter assembly may be incorporated into the syringe itself during use. The method of sizing the microspheres will then comprise using a syringe comprising a barrel, at least one filter, and a needle; and will be carried out by a step of extracting which comprises extruding said microspheres from said barrel through said filter fitted to said syringe between said barrel and said needle, thereby sizing said microspheres before they are administered to a patient in the course of using the microspheres as MRI contrast agents in accordance with the present invention. The step of extracting may also comprise drawing said microspheres into said syringe, where the filter will function in the same way to size the microspheres upon entrance into the syringe. Another alternative is to fill such a syringe with microspheres which have already been sized by some other means, in which case the filter now functions to ensure that only microspheres within the desired size range, or of the desired maximum size, are subsequently administered by extrusion from the syringe.

Figure 2:
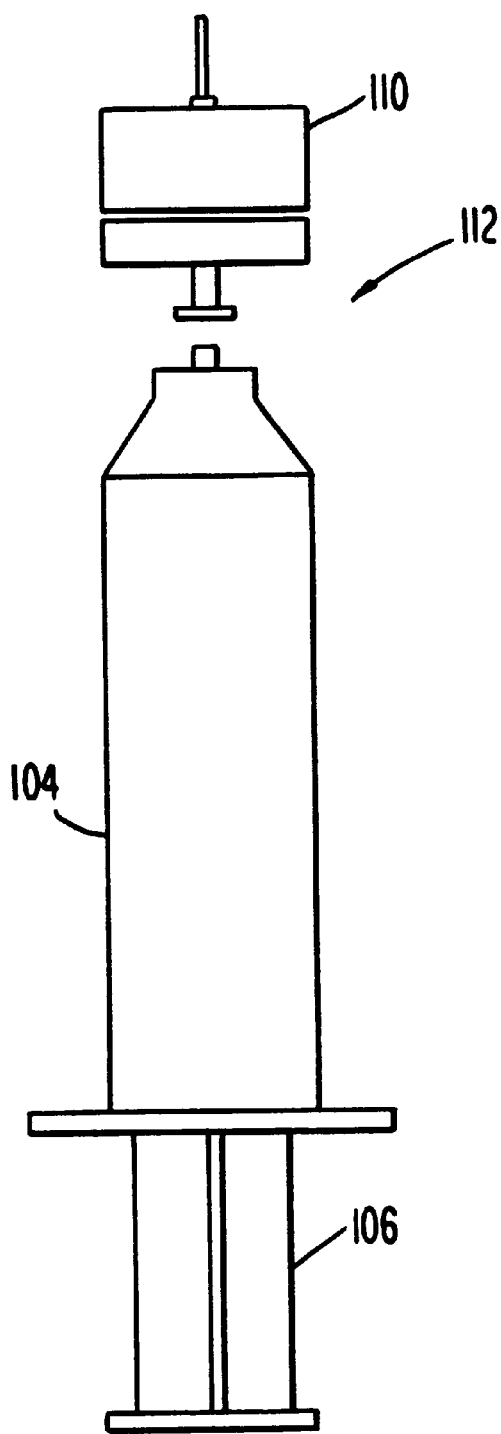
FIG. 2 is a diagrammatic representation of an apparatus for filtering and/or dispensing an MRI contrast medium comprising stabilized gas filled microspheres of the present invention.

Typical of the devices which can be used for carrying out the sizing or filtration step, is the syringe and filter combination shown in FIG. 2. This device consists of a cascade filter housing 10, which may be fitted directly onto a syringe 12, comprising a barrel 4 and a plunger 6, thereby allowing cascade filtration at the point of use.

Figure 3:
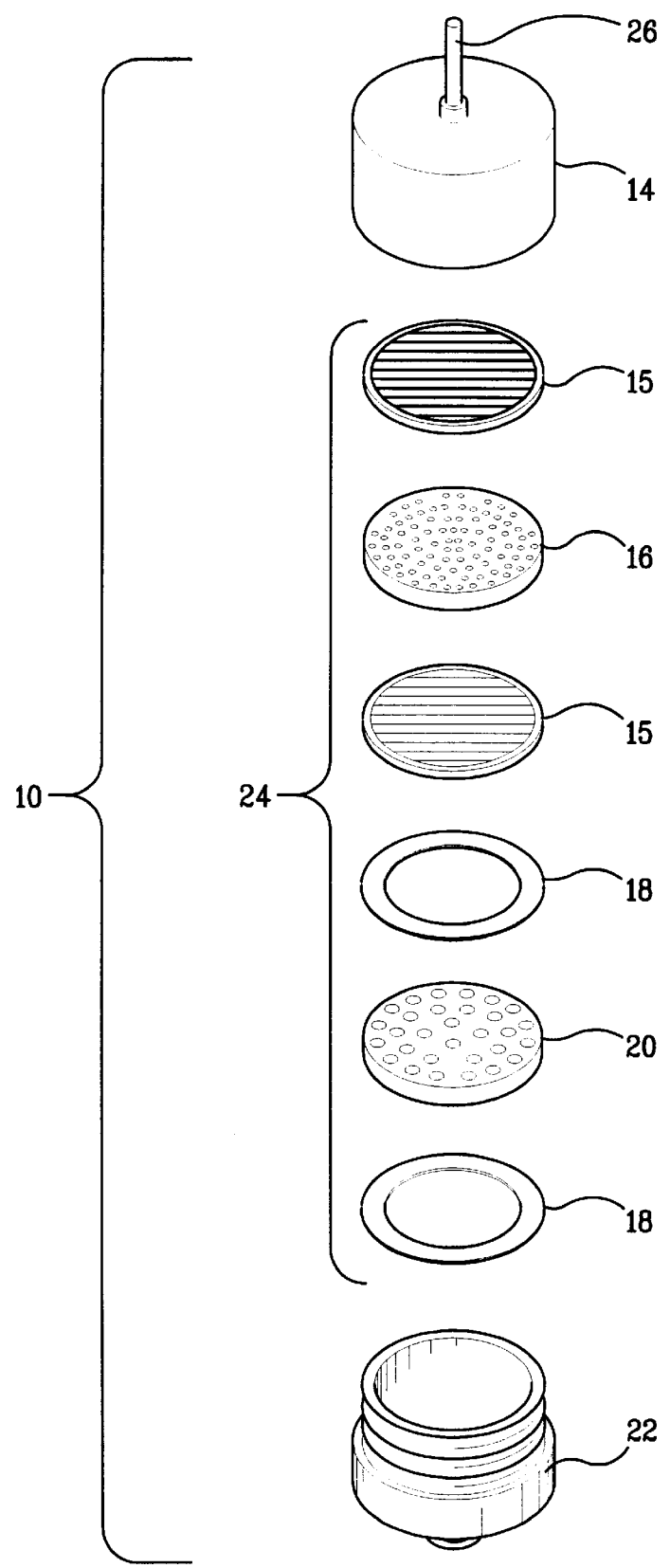
FIG. 3 is an exploded view of a portion of the apparatus of FIG. 2.

FIG. 3 shows further detail regarding the filter. The filter housing 10 comprises a cascade filter assembly 24, incorporated between a lower collar 22, having male threads, and a female collar 14, having female threads. The lower collar 22 is fitted with a Luer lock that allows it to be readily secured to the syringe 12 and the upper collar 14 is fitted with a needle 26. An exploded view of the cascade filter assembly 24, is also shown in FIG. 3. It comprises two successive filters 16 and 20, with filter 20 being disposed upstream of filter 16. In a preferred embodiment, the upstream filter 20 is a "NUCLEPORE" 10 μm filter and the downstream filter 16 is a "NUCLEPORE" 8 μm filter. Two 0.15 mm metallic mesh discs 15 are preferably installed on either side of the filter 16. In a preferred embodiment, the filters 16 and 20 are spaced apart a minimum of 150 μm by means of a Teflon™ O-ring, 18.

In preferred embodiments, the stabilizing compound solution or suspension is extruded through a filter and the said solution or suspension is heat sterilized prior to shaking. Once gas filled microspheres are formed, they may be filtered for sizing as described above. These steps prior to the formation of gas filled microspheres provide the advantages, for example, of reducing the amount of unhydrated stabilizing compound, and thus providing a significantly higher yield of gas filled microspheres, as well as providing sterile gas filled microspheres ready for administration to a patient. For example, a mixing vessel such as a vial or syringe may be filled with a filtered stabilizing compound, especially lipid suspension, and the suspension may then be sterilized within the mixing vessel, for example, by autoclaving. Gas may be instilled into the lipid suspension to form gas filled microspheres by shaking the sterile vessel. Preferably, the sterile vessel is equipped with a filter positioned such that the gas filled microspheres pass through the filter before contacting a patient.

The first step of this preferred method, extruding the stabilizing, especially lipid, solution through a filter, decreases the amount of unhydrated compound by breaking up the dried compound and exposing a greater surface area for hydration. Preferably, the filter has a pore size of about 0.1 to about 5 μm, more preferably, about 0.1 to about 4 μm, even more preferably, about 0.1 to about 2 μm, and most preferably, about 1 μm. Unhydrated compound, especially lipid, appears as amorphous clumps of non-uniform size and is undesirable.

The second step, sterilization, provides a composition that may be readily administered to a patient for MRI imaging. Preferably, sterilization is accomplished by heat sterilization, preferably, by autoclaving the solution at a temperature of at least about 100° C., and more preferably, by autoclaving at about 100° C. to about 130° C., even more preferably, about 110° C. to about 130° C., even more preferably, about 120° C. to about 130° C., and most preferably, about 130° C. Preferably, heating occurs for at least about 1 minute, more preferably, about 1 to about 30 minutes, even more preferably, about 10 to about 20 minutes, and most preferably, about 15 minutes.

If desired, alternatively the first and second steps, as outlined above, may be reversed, or only one of the two steps employed.

Where sterilization occurs by a process other than heat sterilization at a temperature which would cause rupture of the gas filled microspheres, sterilization may occur subsequent to the formation of the gas filled microspheres, and is preferred. For example, gamma radiation may be used before and/or after gas filled microspheres are formed.

-Utilizing a Gaseous Precursor

In addition to the aforementioned embodiments, one can also use gaseous precursors contained in the lipid-based microspheres that can, upon activation by temperature, light, or pH, or other properties of the tissues of a host to which it is administered, undergo a phase transition from a liquid entrapped in the lipid-based microspheres, to a gaseous state, expanding to create the stabilized, gas filled microspheres used in the present invention. This technique is described in detail in patent application Ser. Nos. 08/160, 232, filed Nov. 30, 1993, and 08/159,687, filed Nov. 30, 1993, both of which are incorporated herein by reference in their entirety. The techniques for preparing gaseous precursor filled microspheres are generally similar to those described for the preparation of gas filled microspheres herein, except that a gaseous precursor is substituted for the gas.

The preferred method of activating the gaseous precursor is by temperature. Activation or transition temperature, and like terms, refer to the boiling point of the gaseous precursor, the temperature at which the liquid to gaseous phase transition of the gaseous precursor takes place. Useful gaseous precursors are those gases which have boiling points in the range of about −100° C. to 70° C. The activation temperature is particular to each gaseous precursor. An activation temperature of about 37° C., or human body temperature, is preferred for gaseous precursors of the present invention. Thus, a liquid gaseous precursor is activated to become a gas at 37° C. However, the gaseous precursor may be in liquid or gaseous phase for use in the methods of the present invention. The methods of preparing the MRI contrast agents used in the present invention may be carried out below the boiling point of the gaseous precursor such that a liquid is incorporated into a microsphere. In addition, the said methods may be performed at the boiling point of the gaseous precursor such that a gas is incorporated into a microsphere. For gaseous precursors having low temperature boiling points, liquid precursors may be emulsified using a microfluidizer device chilled to a low temperature. The boiling points may also be depressed using solvents in liquid media to utilize a precursor in liquid form. Further, the methods may be performed where the temperature is increased throughout the process, whereby the process starts with a gaseous precursor as a liquid and ends with a gas.

The gaseous precursor may be selected so as to form the gas in situ in the targeted tissue or fluid, in vivo upon entering the patient or animal, prior to use, during storage, or during manufacture. The methods of producing the temperature-activated gaseous precursor-filled microspheres may be carried out at a temperature below the boiling point of the gaseous precursor. In this embodiment, the gaseous precursor is entrapped within a microsphere such that the phase transition does not occur during manufacture. Instead, the gaseous precursor-filled microspheres are manufactured in the liquid phase of the gaseous precursor. Activation of the phase transition may take place at any time as the temperature is allowed to exceed the boiling point of the precursor. Also, knowing the amount of liquid in a droplet of liquid gaseous precursor, the size of the microspheres upon attaining the gaseous state may be determined.

Alternatively, the gaseous precursors may be utilized to create stable gas filled microspheres which are pre-formed prior to use. In this embodiment, the gaseous precursor is added to a container housing a suspending and/or stabilizing medium at a temperature below the liquid-gaseous phase transition temperature of the respective gaseous precursor. As the temperature is then exceeded, and an emulsion is formed between the gaseous precursor and liquid solution, the gaseous precursor undergoes transition from the liquid to the gaseous state. As a result of this heating and gas formation, the gas displaces the air in the head space above the liquid suspension so as to form gas filled lipid spheres which entrap the gas of the gaseous precursor, ambient gas (e.g., air) or coentrap gas state gaseous precursor and ambient air. This phase transition can be used for optimal mixing and stabilization of the MRI contrast medium. For example, the gaseous precursor, perfluorobutane, can be entrapped in the biocompatible lipid or other stabilizing compound, and as the temperature is raised, beyond 4° C. (boiling point of perfluorobutane) stabilizing compound entrapped fluorobutane gas results. As an additional example, the gaseous precursor fluorobutane, can be suspended in an aqueous suspension containing emulsifying and stabilizing agents such as glycerol or propylene glycol and vortexed on a commercial vortexer. Vortexing is commenced at a temperature low enough that the gaseous precursor is liquid and is continued as the temperature of the sample is raised past the phase transition temperature from the liquid to gaseous state. In so doing, the precursor converts to the gaseous state during the microemulsification process. In the presence of the appropriate stabilizing agents, surprisingly stable gas filled microspheres result.

Accordingly, the gaseous precursors may be selected to form a gas filled microsphere in vivo or may be designed to produce the gas filled microsphere in situ, during the manufacturing process, on storage, or at some time prior to use.

As a further embodiment of this invention, by preforming the liquid state of the gaseous precursor into an aqueous emulsion and maintaining a known size, the maximum size of the microbubble may be estimated by using the ideal gas law, once the transition to the gaseous state is effectuated.

For the purpose of making gas filled microspheres from gaseous precursors, the gas phase is assumed to form instantaneously and no gas in the newly formed microsphere has been depleted due to diffusion into the liquid (generally aqueous in nature). Hence, from a known liquid volume in the emulsion, one actually would be able to predict an upper limit to the size of the gaseous microsphere.

Pursuant to the present invention, an emulsion of a stabilizing compound such as a lipid, and a gaseous precursor, containing liquid droplets of defined size may be formulated, such that upon reaching a specific temperature, the boiling point of the gaseous precursor, the droplets will expand into gas filled microspheres of defined size. The defined size represents an upper limit to the actual size because factors such as gas diffusion into solution, loss of gas to the atmosphere, and the effects of increased pressure are factors for which the ideal gas law cannot account.

The ideal gas law and the equation for calculating the increase in volume of the gas bubbles on transition from the liquid to gaseous states is as follows:

$$PV=nRT$$

where
P=pressure in atmospheres
V=volume in liters
n=moles of gas
T=temperature in ° K.
R=ideal gas constant=22.4 L atmospheres deg$^{-1}$ mole$^{-1}$ With knowledge of volume, density, and temperature of the liquid in the emulsion of liquids, the amount (e.g., number of moles) of liquid precursor as well as the volume of liquid precursor, a priori, may be calculated, which when converted to a gas, will expand into a microsphere of known volume. The calculated volume will reflect an upper limit to the size of the gas filled microsphere, assuming instantaneous expansion into a gas filled microsphere and negligible diffusion of the gas over the time of the expansion.

Thus, for stabilization of the precursor in the liquid state in an emulsion wherein the precursor droplet is spherical, the volume of the precursor droplet may be determined by the equation:

$$\text{Volume (sphere)} = 4/3 \, \pi r^3$$

where
r=radius of the sphere

Thus, once the volume is predicted, and knowing the density of the liquid at the desired temperature, the amount of liquid (gaseous precursor) in the droplet may be determined. In more descriptive terms, the following can be applied:

$$V_{gas}=4/3 \, \pi(r_{gas})^3$$

by the ideal gas law, $$PV=nRT$$

substituting reveals, $$V_{gas}=nRT/P_{gas}$$

or, (A) $n = 4/3 \, [\pi r_{gas}^3] \, P/RT$ amount $n = 4/3 \, [\pi r_{gas}^3] \, P/RT] * MW_n$ Converting back to a liquid volume (B) $V_{liq} = [4/3 \, [\pi r_{gas}^3] \, P/RT] * MW_n/D]$ where D=the density of the precursor Solving for the diameter of the liquid droplet, (C) diameter$/2 = [3/4\pi [4/3*[\pi r_{gas}^3] \, P/RT] \, MW_n/D]^{1/3}$ which reduces to Diameter$= 2[[r_{gas}^3] \, P/RT \, [MW_n/D]]^{1/3}$ As a further means of preparing microspheres of the desired size for use as MRI contrast agents in the present invention, and with a knowledge of the volume and especially the radius of the stabilizing compound/precursor liquid droplets, one can use appropriately sized filters in order to size the gaseous precursor droplets to the appropriate diameter sphere.

A representative gaseous precursor may be used to form a microsphere of defined size, for example, 10µ diameter. In this example, the microsphere is formed in the bloodstream of a human being, thus the typical temperature would be 37° C. or 310° K. At a pressure of 1 atmosphere and using the equation in (A), $7.54 \times 10^{-17}$ moles of gaseous precursor would be required to fill the volume of a 10µ diameter microsphere.

Using the above calculated amount of gaseous precursor, and 1-fluorobutane, which possesses a molecular weight of 76.11, a boiling point of 32.5° C. and a density of 0.7789 grams/mL$^{-1}$ at 20° C., further calculations predict that $5.74 \times 10^{-15}$ grams of this precursor would be required for a 10µ microsphere. Extrapolating further, and armed with the knowledge of the density, equation (B) further predicts that $8.47 \times 10^{-16}$ mLs of liquid precursor are necessary to form a microsphere with an upper limit of 10µ.

Finally, using equation (C), an emulsion of lipid droplets with a radius of 0.0272µ or a corresponding diameter of 0.0544µ need be formed to make a gaseous precursor filled microsphere with an upper limit of a 10µ microsphere.

An emulsion of this particular size could be easily achieved by the use of an appropriately sized filter. In addition, as seen by the size of the filter necessary to form gaseous precursor droplets of defined size, the size of the filter would also suffice to remove any possible bacterial contaminants and, hence, can be used as a sterile filtration as well.

This embodiment for preparing gas filled microspheres used as MRI contrast agents in the methods of the present invention may be applied to all gaseous precursors activated by temperature. In fact, depression of the freezing point of the solvent system allows the use gaseous precursors which would undergo liquid-to-gas phase transitions at temperatures below 0° C. The solvent system can be selected to provide a medium for suspension of the gaseous precursor. For example, 20% propylene glycol miscible in buffered saline exhibits a freezing point depression well below the freezing point of water alone. By increasing the amount of propylene glycol or adding materials such as sodium chloride, the freezing point can be depressed even further.

The selection of appropriate solvent systems may be explained by physical methods as well. When substances, solid or liquid, herein referred to as solutes, are dissolved in a solvent, such as water based buffers for example, the freezing point is lowered by an amount that is dependent upon the composition of the solution. Thus, as defined by Wall, one can express the freezing point depression of the solvent by the following equation:

$$lnx_a = ln \, (1-x_b) = \Delta H_{fus}/R(1/T_o - 1/T)$$

where:
$x_a$=mole fraction of the solvent
$x_b$=mole fraction of the solute
$\Delta H_{fus}$=heat of fusion of the solvent
$T_o$=Normal freezing point of the solvent The normal freezing point of the solvent results from solving the equation. If $x_b$ is small relative to $x_a$, then the above equation may be rewritten:

$$x^b = \Delta H_{fus}/R[T-T_o/T_oT] = \Delta H_{fus} \Delta T/RT_o^2$$

The above equation assumes the change in temperature $\Delta T$ is small compared to $T_2$. The above equation can be simplified further assuming the concentration of the solute (in moles per thousand grams of solvent) can be expressed in terms of the molality, m. Thus, $$X_b = m/[m+1000/m_a] = mMa/1000$$

where:
Ma=Molecular weight of the solvent, and
m=molality of the solute in moles per 1000 grams.

Thus, substituting for the fraction $x_b$:

$$\Delta T = [M_a RT_o^2/1000 \Delta H_{fus}]m$$

or $\Delta T = K_f m$, where $$K_f = M_a RT_o^2/1000 \Delta H_{fus}$$

$K_f$ is referred to as the molal freezing point and is equal to 1.86 degrees per unit of molal concentration for water at one atmosphere pressure. The above equation may be used to accurately determine the molal freezing point of gaseous-precursor filled microsphere solutions used in the present invention.

Hence, the above equation can be applied to estimate freezing point depressions and to determine the appropriate concentrations of liquid or solid solute necessary to depress the solvent freezing temperature to an appropriate value.

Methods of preparing the temperature activated gaseous precursor-filled microspheres include:

(a) vortexing an aqueous suspension of gaseous precursor-filled microspheres used in the present invention; variations on this method include optionally autoclaving before shaking, optionally heating an aqueous suspension of gaseous precursor and lipid, optionally venting the vessel containing the suspension, optionally shaking or permitting the gaseous precursor microspheres to form spontaneously and cooling down the gaseous precursor filled microsphere suspension, and optionally extruding an aqueous suspension of gaseous precursor and lipid through a filter of about 0.22µ, alternatively, filtering may be performed during in vivo administration of the resulting microspheres such that a filter of about 0.22µ is employed;

(b) a microemulsification method whereby an aqueous suspension of gaseous precursor-filled microspheres of the present invention are emulsified by agitation and heated to form microspheres prior to administration to a patient; and (c) forming a gaseous precursor in lipid suspension by heating, and/or agitation, whereby the less dense gaseous precursor-filled microspheres float to the top of the solution by expanding and displacing other microspheres in the vessel and venting the vessel to release air; and (d) in any of the above methods, utilizing a sealed vessel to hold the aqueous suspension of gaseous precursor and stabilizing compound such as biocompatible lipid, said suspension being maintained at a temperature below the phase transition temperature of the gaseous precursor, followed by autoclaving to move the temperature above the phase transition temperature, optionally with shaking, or permitting the gaseous precursor microspheres to form spontaneously, whereby the expanded gaseous precursor in the sealed vessel increases the pressure in said vessel, and cooling down the gas filled microsphere suspension.

Freeze drying is useful to remove water and organic materials from the stabilizing compounds prior to the shaking gas instillation method. Drying-gas instillation methods may be used to remove water from microspheres. By pre-entrapping the gaseous precursor in the dried microspheres (i.e., prior to drying) after warming, the gaseous precursor may expand to fill the microsphere. Gaseous precursors can also be used to fill dried microspheres after they have been subjected to vacuum. As the dried microspheres are kept at a temperature below their gel state to liquid crystalline temperature, the drying chamber can be slowly filled with the gaseous precursor in its gaseous state, e.g., perfluorobutane can be used to fill dried microspheres composed of dipalmitoylphosphatidylcholine (DPPC) at temperatures between 4° C. (the boiling point of perfluorobutane) and below 40° C., the phase transition temperature of the biocompatible lipid. In this case, it would be most preferred to fill the microspheres at a temperature about 4° C. to about 5° C.

Preferred methods for preparing the temperature activated gaseous precursor-filled microspheres comprise shaking an aqueous solution having a stabilizing compound such as a biocompatible lipid in the presence of a gaseous precursor at a temperature below the gel state to liquid crystalline state phase transition temperature of the lipid. The present invention also contemplates the use of a method for preparing gaseous precursor-filled microspheres comprising shaking an aqueous solution comprising a stabilizing compound such as a biocompatible lipid in the presence of a gaseous precursor, and separating the resulting gaseous precursor-filled microspheres for MRI imaging use. Microspheres prepared by the foregoing methods are referred to herein as gaseous precursor-filled microspheres prepared by a gel state shaking gaseous precursor instillation method.

Conventional, aqueous-filled liposomes of the prior art are routinely formed at a temperature above the phase transition temperature of the lipids used to make them, since they are more flexible and thus useful in biological systems in the liquid crystalline state. See, for example, Szoka and Papahadjopoulos, *Proc. Natl. Acad. Sci.* 1978, 75, 4194–4198. In contrast, the microspheres made according to preferred embodiments described herein are gaseous precursor-filled, which imparts greater flexibility, since gaseous precursors after gas formation are more compressible and compliant than an aqueous solution. Thus, the gaseous precursor-filled microspheres may be utilized in biological systems when formed at a temperature below the phase transition temperature of the lipid, even though the gel phase is more rigid.

The methods contemplated by the present invention provide for shaking an aqueous solution comprising a stabilizing compound such as a biocompatible lipid in the presence of a temperature activated gaseous precursor. Shaking, as used herein, is defined as a motion that agitates an aqueous solution such that gaseous precursor is introduced from the local ambient environment into the aqueous solution. Any type of motion that agitates the aqueous solution and results in the introduction of gaseous precursor may be used for the shaking. The shaking must be of sufficient force to allow the formation of a suitable number of microspheres after a period of time. Preferably, the shaking is of sufficient force such that microspheres are formed within a short period of time, such as 30 minutes, and preferably within 20 minutes, and more preferably, within 10 minutes. The shaking may be by microemulsifying, by microfluidizing, for example, swirling (such as by vortexing), side-to-side, or up and down motion. In the case of the addition of gaseous precursor in the liquid state, sonication may be used in addition to the shaking methods set forth above. Further, different types of motion may be combined. Also, the shaking may occur by shaking the container holding the aqueous lipid solution, or by shaking the aqueous solution within the container without shaking the container itself. Further, the shaking may occur manually or by machine. Mechanical shakers that may be used include, for example, a shaker table, such as a VWR Scientific (Cerritos, Calif.) shaker table, a microfluidizer, Wig-L-Bug™ (Crescent Dental Manufacturing, Inc., Lyons, Ill.), which has been found to give particularly good results, and a mechanical paint mixer, as well as other known machines. Another means for producing shaking includes the action of gaseous precursor emitted under high velocity or pressure. It will also be understood that preferably, with a larger volume of aqueous solution, the total amount of force will be correspondingly increased. Vigorous shaking is defined as at least about 60 shaking motions per minute, and is preferred. Vortexing at least 1000 revolutions per minute, an example of vigorous shaking, is more preferred. Vortexing at 1800 revolutions per minute is most preferred.

The formation of gaseous precursor-filled microspheres upon shaking can be detected by the presence of a foam on the top of the aqueous solution. This is coupled with a decrease in the volume of the aqueous solution upon the formation of foam. Preferably, the final volume of the foam is at least about two times the initial volume of the aqueous lipid solution; more preferably, the final volume of the foam is at least about three times the initial volume of the aqueous solution; even more preferably, the final volume of the foam is at least about four times the initial volume of the aqueous solution; and most preferably, all of the aqueous lipid solution is converted to foam.

The required duration of shaking time may be determined by detection of the formation of foam. For example, 10 ml of lipid solution in a 50 ml centrifuge tube may be vortexed for approximately 15–20 minutes or until the viscosity of the gaseous precursor-filled microspheres becomes sufficiently thick so that it no longer clings to the side walls as it is swirled. At this time, the foam may cause the solution containing the gaseous precursor-filled microspheres to raise to a level of 30 to 35 ml.

The concentration of stabilizing compound, especially lipid required to form a preferred foam level will vary depending upon the type of stabilizing compound such as biocompatible lipid used, and may be readily determined by one skilled in the art, once armed with the present disclosure. For example, in preferred embodiments, the concentration of 1,2-dipalimitoylphosphatidylcholine (DPPC) used to form gaseous precursor-filled microspheres according to methods contemplated by the present invention is about 20 mg/ml to about 30 mg/ml saline solution. The concentration of distearoylphosphatidylcholine (DSPC) used in preferred embodiments is about 5 mg/ml to about 10 mg/ml saline solution.

Specifically, DPPC in a concentration of 20 mg/ml to 30 mg/ml, upon shaking, yields a total suspension and entrapped gaseous precursor volume four times greater than the suspension volume alone. DSPC in a concentration of 10 mg/ml, upon shaking, yields a total volume completely devoid of any liquid suspension volume and contains entirely foam.

It will be understood by one skilled in the art, once armed with the present disclosure, that the lipids and other stabilizing compounds used as starting materials, or the microsphere final products, may be manipulated prior and subsequent to being subjected to the methods contemplated by the present invention. For example, the stabilizing compound such as a biocompatible lipid may be hydrated and then lyophilized, processed through freeze and thaw cycles, or simply hydrated. In preferred embodiments, the lipid is hydrated and then lyophilized, or hydrated, then processed through freeze and thaw cycles and then lyophilized, prior to the formation of gaseous precursor-filled microspheres.

According to the methods contemplated by the present invention, the presence of gas, such as and not limited to air, may also be provided by the local ambient atmosphere. The local ambient atmosphere may be the atmosphere within a sealed container, or in an unsealed container, may be the external environment. Alternatively, for example, a gas may be injected into or otherwise added to the container having the aqueous lipid solution or into the aqueous lipid solution itself in order to provide a gas other than air. Gases that are not heavier than air may be added to a sealed container while gases heavier than air may be added to a sealed or an unsealed container. Accordingly, the present invention includes co-entrapment of air and/or other gases along with gaseous precursors.

As already described above in the section dealing with the stabilizing compound, the preferred methods contemplated by the present invention are carried out at a temperature below the gel state to liquid crystalline state phase transition temperature of the lipid employed. By "gel state to liquid crystalline state phase transition temperature", it is meant the temperature at which a lipid bilayer will convert from a gel state to a liquid crystalline state. See, for example, Chapman et al., *J. Biol. Chem.* 1974, 249, 2512–2521.

Hence, the stabilized microsphere precursors described above, can be used in the same manner as the other stabilized microspheres used in the present invention, once activated by application to the tissues of a host, where such factors as temperature or pH may be used to cause generation of the gas. It is preferred that this embodiment is one wherein the gaseous precursors undergo phase transitions from liquid to gaseous states at near the normal body temperature of said host, and are thereby activated by the temperature of said host tissues so as to undergo transition to the gaseous phase therein. More preferably still, this method is one wherein the host tissue is human tissue having a normal temperature of about 37° C., and wherein the gaseous precursors undergo phase transitions from liquid to gaseous states near 37° C.

All of the above embodiments involving preparations of the stabilized gas filled microspheres used in the present invention, may be sterilized by autoclave or sterile filtration if these processes are performed before either the gas instillation step or prior to temperature mediated gas conversion of the temperature sensitive gaseous precursors within the suspension. Alternatively, one or more antibactericidal agents and/or preservatives may be included in the formulation of the contrast medium, such as sodium benzoate, all quaternary ammonium salts, sodium azide, methyl paraben, propyl paraben, sorbic acid, ascorbylpalmitate, butylated hydroxyanisole, butylated hydroxytoluene, chlorobutanol, dehydroacetic acid, ethylenediamine, monothioglycerol, potassium benzoate, potassium metabisulfite, potassium sorbate, sodium bisulfite, sulfur dioxide, and organic mercurial salts. Such sterilization, which may also be achieved by other conventional means, such as by irradiation, will be necessary where the stabilized microspheres are used for imaging under invasive circumstances, e.g., intravascularly or intraperitonealy. The appropriate means of sterilization will be apparent to the artisan instructed by the present description of the stabilized gas filled microspheres and their use. The contrast medium is generally stored as an aqueous suspension but in the case of dried microspheres or dried lipidic spheres the contrast medium may be stored as a dried powder ready to be reconstituted prior to use.

Methods of Use

The novel stabilized gas filled microspheres, useful as contrast media in magnetic resonance imaging (MRI), will be found to be suitable for use in all areas where MRI is employed. However, the stabilized microspheres are particularly useful for perfusion imaging and may also be utilized to obtain non-invasive pressure information in vivo.

In accordance with the present invention there is provided a method of imaging a patient generally, and/or in specifically diagnosing the presence of diseased tissue in a patient. The imaging process of the present invention may be carried out by administering a contrast medium of the invention to a patient, and then scanning the patient using magnetic resonance imaging to obtain visible images of an internal region of a patient and/or of any diseased tissue in that region. By region of a patient, it is meant the whole patient or a particular area or portion of the patient. The contrast medium may be particularly useful in providing images of the cardiovascular region or the gastrointestinal region, but can also be employed more broadly such as in imaging the vasculature or in other ways as will be readily apparent to those skilled in the art. Cardiovacular region, as that phrase is used herein, denotes the region of the patient defined by the heart and the vasculature leading directly to and from the heart. The phrase gastrointestinal region or gastrointestinal tract, as used herein, includes the region of a patient defined by the esophagus, stomach, small and large intestines and rectum. The phrase vasculature, as used herein, denotes the blood vessels (arteries, veins, etc.) in the body or in an organ or part of the body. The patient can be any type of mammal, but most preferably is a human.

As one skilled in the art would recognize, administration of the stabilized gas filled microspheres used in the present invention may be carried out in various fashions, such as intravascularly, orally, rectally, etc., using a variety of dosage forms. When the region to be scanned is the cardiovascular region, administration of the contrast medium of the invention is preferably carried out intravascularly. When the region to be scanned is the gastrointestinal region, administration of the contrast medium of the invention is preferably carried out orally or rectally. The useful dosage to be administered and the particular mode of administration will vary depending upon the age, weight and the particular mammal and region thereof to be scanned, and the particular contrast medium of the invention to be employed. Typically, dosage is initiated at lower levels and increased until the desired contrast enhancement is achieved. Various combinations of the stabilized gas filled microspheres may be used to modify the relaxation behavior of the medium or to alter properties such as the viscosity, osmolarity or palatability (in the case of orally administered materials). In carrying out the magnetic resonance imaging method of the present invention, the contrast medium can be used alone, or in combination with other diagnostic, therapeutic or other agents. Such other agents include excipients such as flavoring or coloring materials. The magnetic resonance imaging techniques which are employed are conventional and are described, for example, in D. M. Kean and M. A. Smith, *Magnetic Resonance Imaging: Principles and Applications,* (William and Wilkins, Baltimore 1986). Contemplated MRI techniques include, but are not limited to, nuclear magnetic resonance (NMR) and electronic spin resonance (ESR). The preferred imaging modality is NMR.

As noted above, the routes of administration and areas of usefulness of the gas filled microspheres are not limited merely to the blood volume space, i.e., the vasculature. MRI can be achieved with the gas filled microspheres used in the present invention if the microspheres are ingested by mouth so as to image the gastrointestinal tract. Alternatively, rectal administration of these stabilized gas microspheres can result in excellent imaging of the lower gastrointestinal tract including the rectum, descending colon, transverse colon, and ascending colon as well as the appendix. It may be possible to achieve imaging of the jejunum and conceivably the ileum via this rectal route. As well, direct intraperitoneal administration may be achieved to visualize the peritoneum. It is also contemplated that the stabilized gas microspheres may be administered directly into the ear canals such that one can visualize the canals as well as the Eustachian tubes and, if a perforation exists, the inner ear. It is also contemplated that the stabilized gas microspheres may be administered intranasally to aid in the visualization of the nasal septum as well as the nasal sinuses by MRI.

Other routes of administration of the microsphere contrast agents of the present invention, and tissue areas whose imaging is enhanced thereby include, but are not limited to 1) intranasally for imaging the nasal passages and sinuses including the nasal region and sinuses and sinusoids; 2) intranasally and orally for imaging the remainder of the respiratory tract, including the trachea, bronchus, bronchioles, and lungs; 3) intracochlearly for imaging the hearing passages and Eustachian tubes, tympanic membranes and outer and inner ear and ear canals; 4) intraocularly for imaging the regions associated with vision; 5) intraperitoneally to visualize the peritoneum; and 6) intravesicularly, i.e., through the bladder, to image all regions of the genitourinary tract via the areas thereof, including, but not limited to, the urethra, bladder, ureters, kidneys and renal vasculature and beyond, e.g., to perform cystography or to confirm the presence of ureteral reflux.

It has also been discovered that it is possible to use the gas filled microspheres used in the present invention to monitor the temperature of localized tissue by the use of gaseous precursor-filled stabilized microspheres in MRI. As already described, the magnetic domains of the spin=½ sensitive nuclei are altered at the interface between the gas and the surrounding aqueous-based media, e.g., blood. It has been discovered that, as the gaseous precursors are moved through their liquid-to-gas phase transition temperature, the magnetic domains are altered. This can be visualized on MRI as a grey scale image, or by mapping the bulk susceptibility of the tissue. With prior knowledge of the liquid-to-gas phase transition temperature, one can then determine the extent of heating of localized tissue by the visualization of the bubbles by MRI. Thus, the present invention includes a method for determining the temperature of localized tissue within the body of a human or animal subject by means of stabilized gas filled microspheres, comprising the steps of (a) preparing a stabilized microspheres precursor by agitating an aqueous suspension of a lipid in the presence of one or more gaseous precursors which undergo phase transitions from liquid to gaseous states in response to increased temperatures, optionally in the presence of a gas, whereby a said precursor comprising microspheres filled with liquid phase gaseous precursor is formed; (b) administering said stabilized microspheres precursor prepared in the preceding step to the tissue of said subject; (c) activation of said gaseous precursor by increasing its temperature so that it undergoes transition to the gaseous phase, together with contemporaneous magnetic resonance imaging of said tissue; and (d) observing that magnetic resonance image enhancement occurs at the phase transition temperature of the gaseous precursor, thereby determining the temperature of said localized tissue. The increase in temperature of said gaseous precursor can take place as a result of natural heating by said tissue to which it has been administered, or it can be the result of heating by the use of ultrasound, microwave energy, or other sources of energy applied to said localized tissue.

Although MRI is currently capable of being used to measure vascular flow rates, to date there has been no suggestion of its use for measuring pressures within the bodies of humans or other mammals. It is yet another aspect of the present invention to accomplish such an objective by using the gas filled microspheres of the present invention and MRI technology. It is contemplated that by using flexible gas filled microspheres as described herein, that it will be possible to non-invasively measure pressures in vivo by MRI. Since $1/T2^*$ is proportional to the radius of the microspheres to the third power or even potentially the sixth power, and since the gas filled microspheres function as elastic bubbles, as they encounter higher regions of pressure, the bubbles will compress and their radii will correspondingly decrease with increasing pressure. And, as a result, $1/T2^*$ will also decrease. Thus, by using T2 or $T2^*$ weighted MR imaging pulse sequences and either directly, or indirectly monitoring $1/T2^*$ in different parts of the body, e.g., arteries and veins, it will be possible to obtain non-invasive measurements of pressure.

Accordingly, a method for determining the pressure of localized tissue within the body of a human or animal subject by means of stabilized gas filled microspheres, would comprise the steps of (a) preparing said stabilized microspheres by agitating an aqueous suspension of a stabilizing compound in the presence of one or more gases and/or gaseous precursors, whereby said microspheres are formed; (b) administering said stabilized microspheres prepared in the preceding step to the tissue of said subject; (c) magnetic resonance imaging said tissue and observing the $1/T2^*$, which is proportional to the radius of said microspheres, and the radii of said microspheres, which will correspondingly decrease with increasing pressure, also causing the $1/T2^*$ to decrease; (d) monitoring $1/T2^*$ in a different part of the body; and (e) by a comparison of the $1/T2^*$ values and the proper calculation, determining the pressure of said localized tissue.

As already mentioned further above, FIGS. 1A and B shows a representative photomicrograph of stabilized gas filled microspheres used in the present invention. As shown in this photomicrograph, the mean diameter of the microspheres is about 7μ. The microspheres are formed from one or more lipid monolayers or bilayers composed of saturated dipalmitoyl-phosphatidylcholine. It will be understood, however, that other lipids may also be utilized. It is preferred, nevertheless, that the alkyl groups of the lipids thus selected be saturated and that the chains be from 16 or 18 carbon atoms in length. Most preferred are alkyl chains having 16 carbon atoms. The resulting gas filled microspheres are quite stable, and even relatively diffusible and soluble gases, such as air, can be stabilized by such liposomal membranes.

FIG. 2 illustrates an apparatus for filtering and/or dispensing an MRI contrast medium comprising stabilized gas filled microspheres of the present invention. This device consists of a cascade filter which may be fitted directly onto a syringe, thereby allowing cascade filtration at the point of use.

FIG. 3 shows further detail regarding the filter. The filter housing comprises a cascade filter assembly incorporated between a lower collar having male threads, and a female collar having female threads. The lower collar can be readily secured to the syringe and the upper collar is fitted with a needle. An exploded view of the cascade filter assembly is also shown in FIG. 3. It comprises two successive filters and in a preferred embodiment, the upstream filter is a "NUCLEPORE" 10 μm filter and the downstream filter is a "NUCLEPORE" 8 μm filter. Two 0.15 mm metallic mesh discs are preferably installed on either side of the downstream filter. In a preferred embodiment, the filters and are spaced apart a minimum of 150 μm by means of a Teflon™ O-ring.

Figure 4:
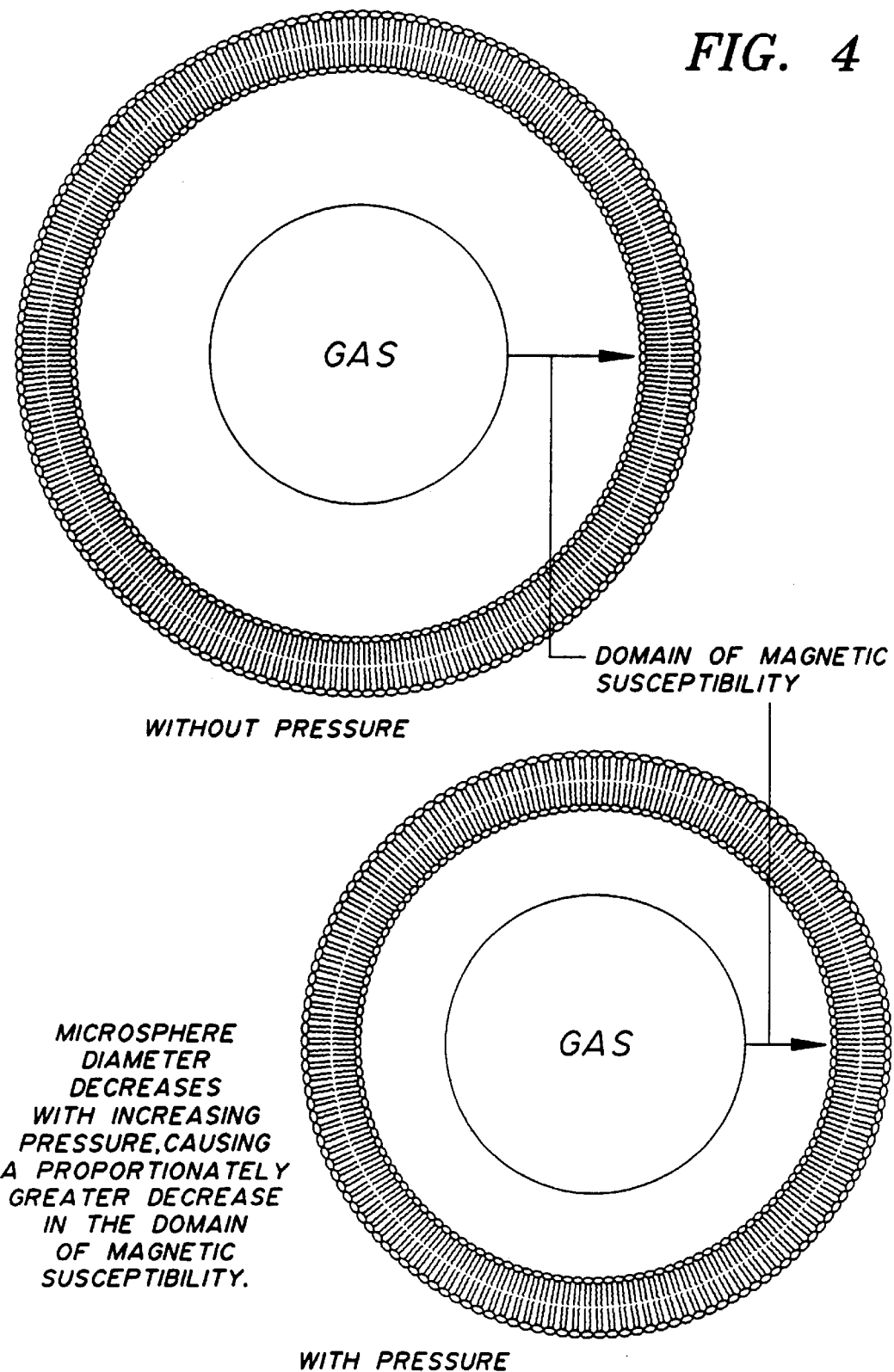
FIG. 4 is a graphic representation of the effect of gas filled microsphere diameter on the domain of magnetization surrounding said microsphere. The domain of magnetization (i.e., domain of magnetic susceptibility) is shown by the region traversed by the arrows. As is shown in the figure, the susceptibility effect or magnetic domain caused by the microsphere has a relationship to microsphere diameter. Microsphere diameter decreases with increasing pressure, causing a proportionately greater decrease in the domain of magnetic susceptibility. For elastic pressure sensitive microspheres, this phenomenon of microsphere diameter/susceptibility dynamics can be utilized to non-invasively assess pressure in vivo by MRI.

FIG. 4 is a diagrammatic representation of the effect of the signal intensity of the microspheres on aqueous samples. High speed fast GRASS imaging was performed on a 1.5 Tesla GE Signa, (Milwaukee, Wis). Samples containing 5, 2.5 and 1.25 mg per ml of lipid entrapping air, xenon and neon, i.e., all three concentrations for each sample, were prepared. Briefly, the gas filled microspheres were prepared from an aqueous suspension of 5 mg per ml of dipalmitoylphosphatidylcholine in a buffer prepared from 8 parts normal saline with 1 part glycerol and 1 part propylene glycol. A 30 ml glass bottle with a rubber stopper was filled with each respective gas and vortexed for 10 minutes using a Vortex Genie-2 (Scientific Industries Inc., Bohemia, N.Y.) at the highest power setting, 6.5. The resultant stabilized microspheres were sized using an Accusizer optical particle sizer (Particle Sizing Systems, Santa Barbara, Calif.) and a Reichert-Jung Model 150 optical microscope (Cambridge Instruments, Inc., Buffalo, N.Y.). Half of the microspheres from each sample were extruded by hand using a syringe through an 8μ filter (Nuclepore, Pleasanton, Calif.). The microspheres prepared without extrusion had a mean size of about 20μ. The microspheres which were extruded had a mean size of about 10μ. A portion of each of the samples of stabilized microspheres was then put into 25 cc syringes, partially filling the syringes. A further portion of each sample was diluted 1:2 with normal saline, and a still further portion of each sample was diluted 1:4 with normal saline. The samples containing the nonextruded microspheres were larger than the extruded microspheres and the larger microspheres were noted to rise very rapidly towards the top of the solution after vigorous shaking.

The invention is further demonstrated in the following working examples representing actual reductions to practice of the present invention. The examples, however, are not intended to in any way limit the scope of the present invention.

EXAMPLES

Example 1

Magnetic Resonance Imaging Procedures Using Gas Filled Microspheres

One Sprague Dawley rat (approx. 500 gms) was anesthetized with 0.55 mL of 8:5:2, v:v:v, xylazine 20 mg mL$^{-1}$, Ketamine 10 mg mL$^{-1}$, and Acepromazine 100 mg mL$^{-1}$. Magnetic resonance imaging was performed on a Bruker Biospec 4.7 Tesla magnet (Bruker Industries, Boston, Mass.) equipped with a Gradient Insert and Radiofrequency (RF) coil. Precontrast imaging was performed with a GRASS Imaging gradient echo fast imaging (GEFl) with a time of repetition (TR) of 32 msec and a time of echo (TE) of 8 msec. The sedated rat was placed head first into the magnet probe and pre-contrast spin-echo images were obtained using the gradient insert and RF coil. The following parameters were employed: Field of View=4 cm, Slice=3 mm, TE=5 msec, TR=32 msec, Number of acquisitions=1. The data was stored as a 128×128 matrix.

The rat was catheterized with a 23 gauge butterfly catheter via the tail vein. Upon determining the patency of the vein, 2.0 mL of gas filled microspheres were injected via slow IV push (duration approximately 10 sec). The complete image required approximately 8 seconds. The image obtained with gas filled microspheres was significant for a profound darkening of the blood vessels in the brain, presumably outlining the circulations through the meningeal circulation. It is further noted that delayed imaging, i.e., after approximately 20 seconds, revealed restoration of the signal intensity through the blood vessels, indicative of the ability of this contrast agent to act as a first pass susceptibility agent.

Example 2

Gas Filled Microspheres As Susceptibility Agents In A Phantom Model For MRI

The procedures as described above in Example 1 were carried out. To a 20 cc syringe was added 10 cc of a control mixture consisting of glycerol:normal saline (1:2, v:v). To a second syringe was added 2.5 mL of gas filled microspheres mixed with 7.5 mL of a glycerol:normal saline (1:2, v:v) mixture. Relative to the control, the gas filled microspheres sample was significant for producing a darkening of the MRI image at the top of the scan, indicative of a susceptibility agent that has floated to the top. Vigorous shaking of the gas filled microspheres sample was then found to be significant for producing a more uniform darkening of the test sample imaging relative to the control. After five minutes, the sample was then re-scanned. This time the test sample was found to be significant for the same darkening of the image at the top relative to control, once again indicative of activity as a susceptibility agent.

Example 3

Gas Filled Microspheres

A 20 ml solution of 10 mg per ml lipid in an 8:1:1 vol normal saline:glycerol:propylene glycol was prepared using an 82 mole percent dipalmitoylphosphatidylcholine (DPPC): 10 mole percent dipalmitoylpshosphatidic acid (DPPA): 8 mole percent dipalmitoylphosphatidylethanolamine-PEG 8,000 mixtures of lipids (all lipids from Avanti Polar Lipids, Alabaster, Ala). The lipids were shaken on a vortexer [VWR Genie-2 (120V, 0.5 amp, 60 Hz.) Scientific Industries, Inc., Bohemia, N.Y.] for 10 minutes creating a foam height of about 100 cc. The above was then mixed with a 0.5% by weight suspension of xanthan gum in 800 cc of water to yield a final volume of about 900 cc. The resulting contrast medium composed of gas filled microspheres formulated from the foregoing lipids was judged to have good contrast and to be suitable for ingestion for contrast of the gastrointestinal (GI) tract.

Example 4
Gas Filled Microspheres

The procedures in Example 3 above were repeated except that distearoylphosphatidylcholine (DSPC) was used instead of DPPC. The resulting microspheres was judged to be superior to the DPPC microspheres and again highly suitable for ingestion as a GI MRI contrast agent.

Example 5
Gas Filled Microspheres

The procedures used above in Examples 3 and 4 were repeated, except that nitrogen gas was used instead of air. The resulting microspheres were judged to be somewhat more stable that those which utilized air, i.e., a larger amount of the foam height was retained upon incubation at 40° C. for the DPPC microspheres and at 50° C. for the DSPC microspheres, when nitrogen gas was used to prepare the microspheres, than when air was used.

Example 6
Gas Filled Microspheres As Susceptibility Agents In a Phantom Model For MRI Samples of the microsphere based GI contrast media prepared in Examples 3–5 were assessed as MRI contrast agents by scanning phantoms in clinical MRI imaging devices. Three different devices were tested, 0.5 and 1.5 Tesla GE Signa magnets (GE Medical Systems, Milwaukee, Wis.) and a 4.7 Tesla Bruker, Biospec II (Bruker, Billerica, Mass.). T1 weighted pulse sequences were tested including T1 weighted spin echo sequences, TR=250 msec/TE=12 msec, T2 weighted fast spin echo pulse sequences (0.5 and 1.5 Tesla only) TR=4000 msec with TE=19 (echo train=4) and 105 msec (echo train=16) and T2 weighted spin echo pulse sequences TR=2,500 msec and TE=25, 50, 75, 100, 125 and 150 msec using a bandwidth of 8 kilohertz. The T2 weighted spin echo pulse sequences were repeated using a bandwidth of 32 kilohertz. Gradient echo pulse sequences were also tested using a TR of 50 msec and TE of 5, 10, 15, 20, 25, 30 and 35 msec using a flip angle of 30 degrees and a bandwidth of 8 kilohertz; the foregoing was repeated with a bandwidth of 32 kilohertz.

The resultant images showed field-strength dependent contrast with decreased signal in the phantom due to the stabilized microspheres most evident on the 4.7 Tesla magnet and in turn more evident on the images at 1.5 Tesla than at 0.5 Tesla. The contrast effect was progressively more pronounced on more highly T2 weighted images, i.e., the longer the echo time the greater the degree of signal loss. Little effect was shown on the T1 weighted images at 0.5 Tesla but progressively more signal loss was evident even on the T1 weighted images at 1.5, and even more at 4.7 Tesla. On the spin echo images changing the bandwidth had no appreciable effect; but on the gradient echo images the degree of signal loss was much more pronounced on the extended read-out, i.e., narrow bandwidth 8 kilohertz images, than on the 32 kilohertz images. Greater contrast was shown on the gradient echo images in general than on the spin echo images. The contrast effect caused by the gas filled microspheres was about the same for the air and nitrogen gas filled microsphere preparations.

Example 7
Gas Filled Microspheres Containing A Paramagnetic Contrast Agent

Microspheres were prepared as in Example 4 except that a solution of 0.75 millimolar manganese chloride was added to the suspension of xanthan gum and this was then mixed with the microspheres. MR imaging was repeated as in Example 6, and it was found that the degree of signal darkening, i.e., contrast effect, was even more marked than before. The contrast was, furthermore, found to be biphasic with increased signal intensity shown on the very shortest echo time T1 weighted images. By comparison, a phantom containing a solution of 0.75 millimolar manganese chloride was scanned; the degree of contrast caused by the manganese chloride solution alone was much less than that for the combined microsphere and paramagnetic particle suspension.

Example 8
Gas Filled Microspheres Prepared Using A Gaseous Precursor

In the foregoing examples of gastrointestinal MRI stabilized gas filled microsphere based contrast agents, the microspheres would be preformed prior to ingestion of the contrast agent. While this is highly effective, gaseous precursor based suspensions can be formulated so as to be more palatable and easily tolerated by the patient.

A precursor GI contrast agent formulation was prepared by mixing a 20 mg per ml concentration of lipids as described in Example 4 with 20 mg per ml of peanut oil and 600–1200 µL of bromochlorofluoromethane, an amount sufficient amount to generate approximately 0.15 L–0.30 L of gas. The above was mixed by vortexing for 10 minutes, although sonication could also have been used, and in turn 100 cc of the gaseous precursor emulsion was then mixed vigorously with 750 cc of a 0.85% suspension of xanthan gum which contained 3% by weight propyleneglycol and 3% by weight glycerol. The above was then scanned by magnetic resonance imaging at room temperature. On MRI the precursor suspension had little contrast compared to a control suspension of 0.85% xanthan gum in water.

A sample of the precursor contrast medium was then placed in a water bath at 40° C. and shaken intermittently Bubbles were noted to form in the emulsion. Because of the xanthan gum viscous suspension, the bubbles appeared to remain within the suspension rather than immediately floating to the top. On MRI the contrast medium was found to have similar contrast as that in Example 6.

Example 9
Gas Filled Microspheres Prepared Using A Gaseous Precursor

The same procedure as in Example 8 was used, except that 1,1 dichloro-1-fluoroethane was used in a sufficient quantity to generate 150 mLs of gas upon undergoing a phase transition at 38° C. (MW 116.95, bp 38° C., density= 125 g/mL).

Example 10
Gas Filled Microspheres

A 5 ml solution of 5 mg per ml lipid comprising 8:1:1 volume ratio of normal saline:glycerol:propylene glycol was prepared using a mixture of 77.5 mole percent DPPC+12.5 mole percent DPPA+10 mole percent of dipalmitoylphosphatidylethanolamine-polyethyleneglycol (DPPE-PEG 5000) a lipid covalently bound to a hydrophilic polymer. Air was evacuated from the 18 ml glass vial entrapping the lipids and the vial was filled with nitrogen to ambient pressure. The material was autoclaved at 121° C. and elevated pressure for 15 minutes and allowed to cool to room temperature. The vial was shaken on a Wig-L-Bug brand shaker for 2 minutes, yielding a thick foam of about 12 cc volume of gas filled microspheres. The size of the gas filled microspheres was determined by Accusizer and found to be as follows: mean size about $5\mu$ with 99.9% of the particles below 15 microns in size.

Example 11
Gas Filled Microspheres Prepared Using A Gasseous Precursor

Example 10 was substantially repeated except that instead of nitrogen the head space in the vial about the lipids was filled with perfluorobutane (decafluorobutane) to ambient pressure, autoclaved and shaken as described above, yielding a volume of gas filled microspheres of about 16 cc. The resultant size of the gas filled microspheres was found to be mean size about 5μ and 99.9% cut-off at about 25μ. A portion of these perfluorobutane microspheres was then placed in a 3 cc syringe and subjected to a single injection through a filter with 8μ filter pore size. The mean size of the resultant microspheres was about 3 to 4μ with 99.9% at about 11μ or below.

Example 12
Gas Filled Microspheres Prepared Using A Gaseous Precursor

The procedures above in Example 11 were repeated with octaperfluoro-cyclobutane, with substantially the same results being obtained as in Example 11.

Example 13
Gas Filled Microspheres Prepared Using A Gaseous Precursor

The procedures above in Example 11 were repeated, except that instead of the diluent 8:1:1 normal saline:glycerol:propyleneglycole normal saline with 5% by weight polyvinylalcohol (PVA, weight average molecular weight about 5,000) was used as the diluent. The same procedure was then followed for formation of the perfluorobutane filled microspheres. The mean size of the gas filled microspheres was about 3 to 4μ, but the 99.9% cut-off was even smaller at about 11μ without the filtration step.

Example 14
Gas Filled Microspheres Prepared Using A Gaseous Precursor

The procedures above in Example 11 were repeated except that 50 microliters of dodecaperfluoropentane (perfluoropentane, boiling point about 27° C.) was injected into the vial containing the liquid lipid suspension. In this case the air head space was not removed and the injection of the perfluoropentane was performed at −20° C. The vial was then autoclaved at 121° C. and elevated pressure for 15 minutes. The vial was then placed in a 30° C. incubator and the temperature allowed to equilibrate. The sample was shaken for 2 minutes on the Wig-L-Bug brand shaker and the entire vial was then filled with foam. A portion of this foam was withdrawn and it was noted that the contents within the vial were under increased pressure. A portion of this foam was sized yielding a mean size of 5.8μ, a 95% cut-off of 19.1μ and a 99.9% cut-off of about 75μ. When a portion of this foam was extruded through the syringe with the 8μ filter, the mean size was about 3 to 4μ with a 99.9% cut-off at about 10μ.

When the above procedures were repeated, except that the vial head space comprising air was evacuated prior to shaking the gaseous perfluoropentane, the mean size of the resultant microspheres was larger than when the microspheres were prepared under pressure with the head space comprising air.

Example 15
Effect of Different Gases on Size Distribution and MRI R2 Relaxivity of Gas Filled Microspheres Samples of gas filled microspheres prepared by agitating aqueous lipid solutions comprising 5 mg per mL of DPPC, DPPA and DPPE-PEG5000 in a mole ratio of 82%:10%:8%, respectively, in separate atmospheres of oxygen ($O_2$), air, nitrogen ($N_2$), xenon (rubidium enriched hyperpolarized), neon, argon, sulfur hexafluoride (SHF or $SF_6$), perfluoropropane (PFP) and perfluorobutane (PFB) gas. The samples were agitated using a Wig-L-Bug™ at 3300 RPM for 60 seconds. The resultant gas-filled liposome samples were then suspended in 4% methyl cellulose in normal saline, to prevent the liposomes from floating to the top during imaging experiments.

Portions of each sample were then placed in plastic syringes and held within a radial array phantom holder which included tubing, a pressure gauge and a syringmamometer, for magnetic resonance imaging. Samples containing 20%, 10%, 5%, 2.5%, 1.25% and 0.625% by volume of each gas were then scanned by magnetic resonance using a Brinker Biospec II 4.7 Tesla scanner (Bruker, Billerica, Mass.). T2 measurements were performed by scanning the samples with Spin Echo Sequences TR=800 msec and TE=30, 45, 60, 75 and 90 msec and gradient echo sequences for signal intensity measurements with TR=60 msec, TE=8 with a 40% flip. Signal intensities were measured by selecting region of interest on the CRT monitor. For T2 measurements the signal intensity data was plotted and the R2 (1/T2/mmol/L.sec−1) was determined for each gas by using the standard gas law to determine the millimolar concentrations of the gas and fitting the T/T2 data versus concentration.

Figure 5A:
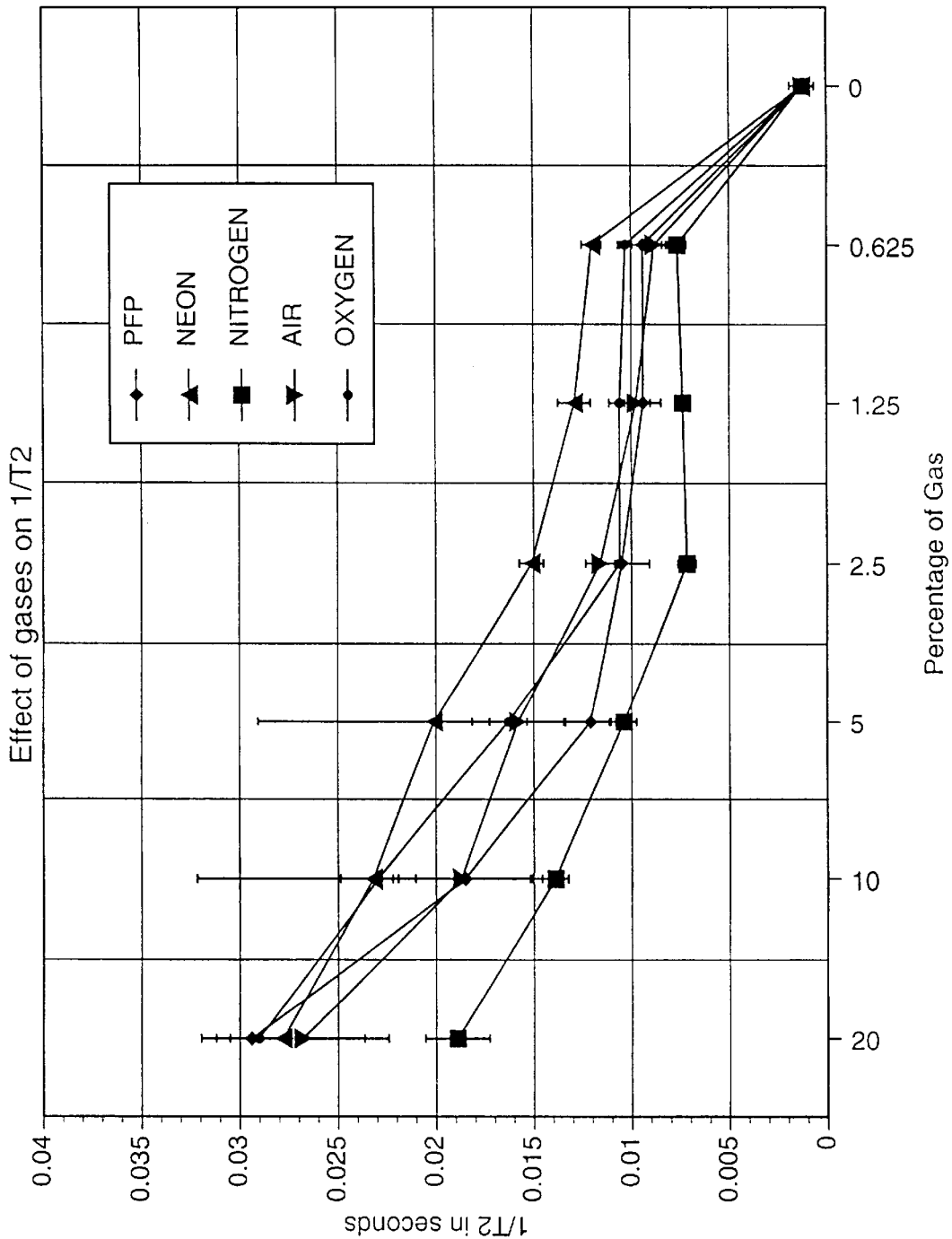
FIG. 5A shows the $1/T_2$ versus gas concentrations for perfluoropropane (PFP), neon, oxygen, air, and nitrogen gas.
Figure 5B:
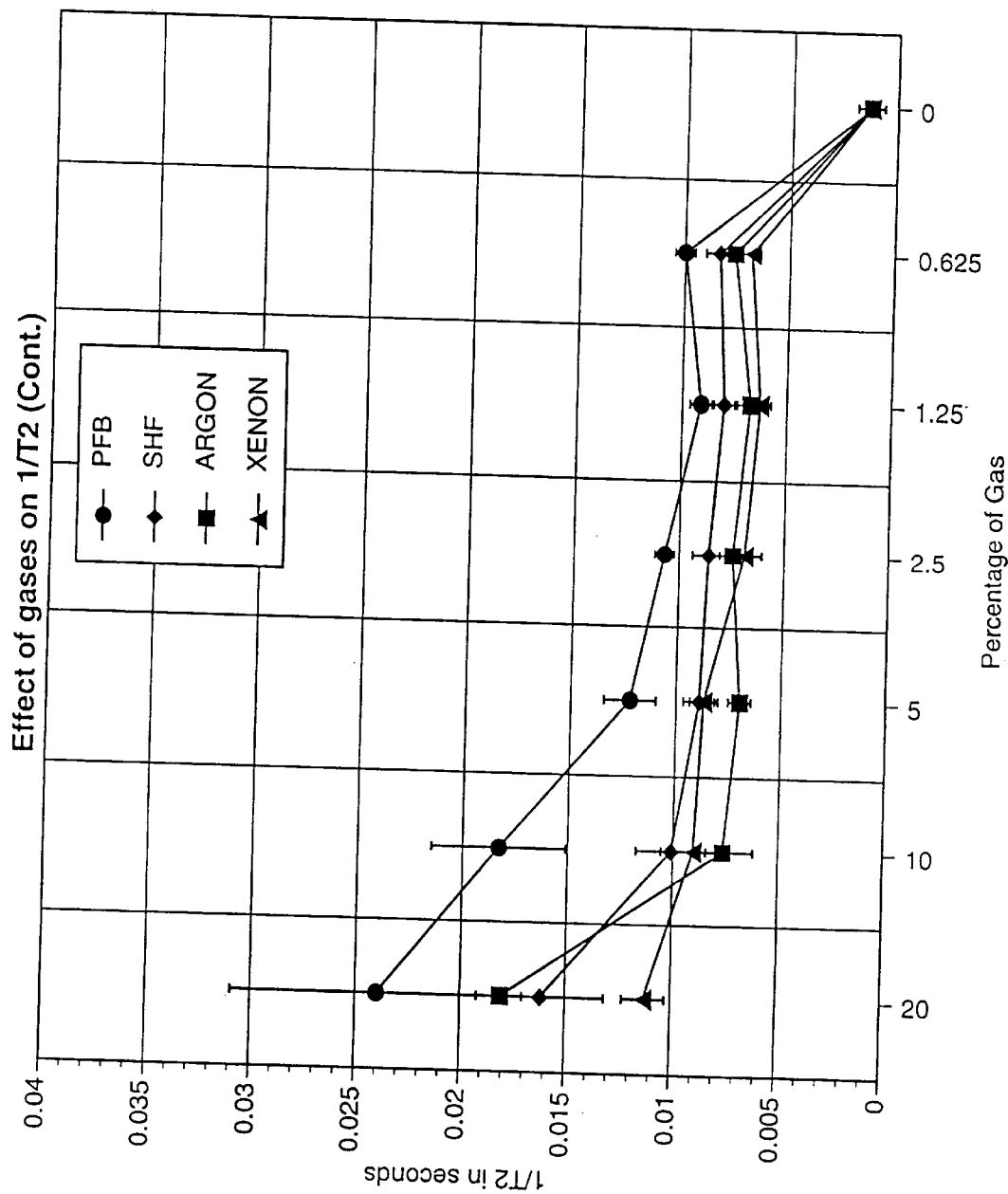
FIG. 5B shows the $1/T_2$ versus gas concentrations for xenon, argon, sulfur hexafluoride (SHF), and perfluorobutane (PFB) gas.

The effect on the various gases on $R_2$ and liposome sizes are shown in the table below. The relationships between $1/T_2$ versus gas concentrations for the different gases are shown in FIGS. 5A and 5B.

TABLE 3

Size Distribution and Relaxivity

| Gas | Number Weighted Distribution | Volume Weighted Distribution | R2 |
|---|---|---|---|
| $N_2$ | 6.96 +/− 0.63 | 31.08 +/− 7.42 | 474.6 +/− 59.9 |
| $SF_6$ | 4.31 +/− 0.13 | 44.25 +/− 1.23 | 319.3 +/− 42.5 |
| Xenon | 7.02 +/− 1.19 | 160.90 +/− 92.46 | 191.2 +/− 30.8 |
| Argon | 8.14 +/− 0.49 | 41.45 +/− 13.02 | 55.29 +/− 41.3 |
| Air | 6.05 +/− 1.05 | 23.28 +/− 0.41 | 1510.4 +/− 0.41 |
| PFP | 4.24 +/− 0.72 | 49.88 +/− 11.11 | 785 +/− 31.8 |
| $O_2$ | 7.26 +/− 0.98 | 30.99 +/− 3.90 | 732.4 +/− 73.9 |
| Neon | 7.92 +/− 0.71 | 26.20 +/− 1.03 | 595.1 +/− 97.2 |
| PFB | 5.88 +/− 0.36 | 51.25 +/− 3.97 | 580.1 +/− 45.5 |

Figure 6:
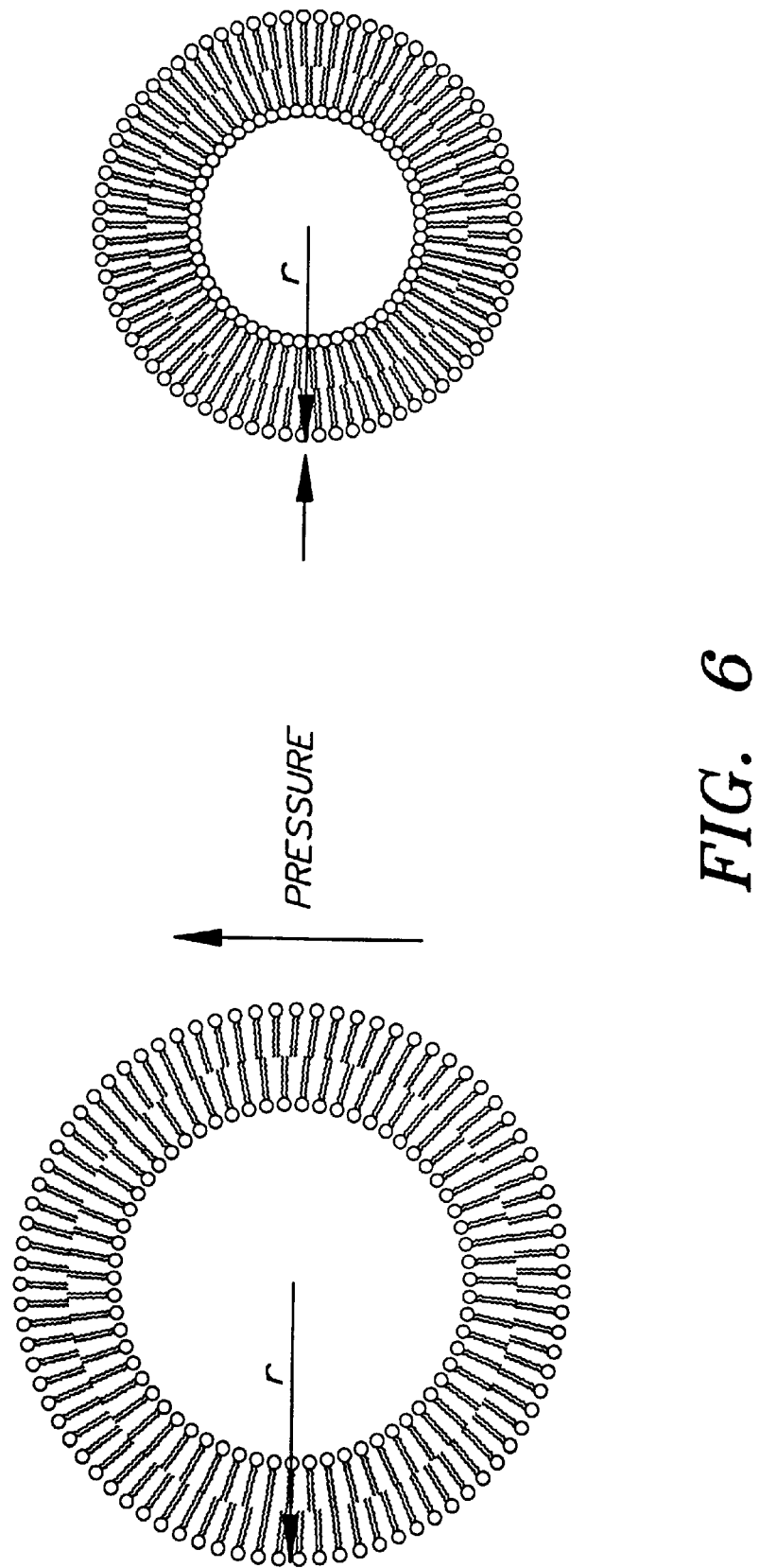
FIG. 6 provides a diagram of the effect of pressure on gas filled microsphere size.
Figure 7:
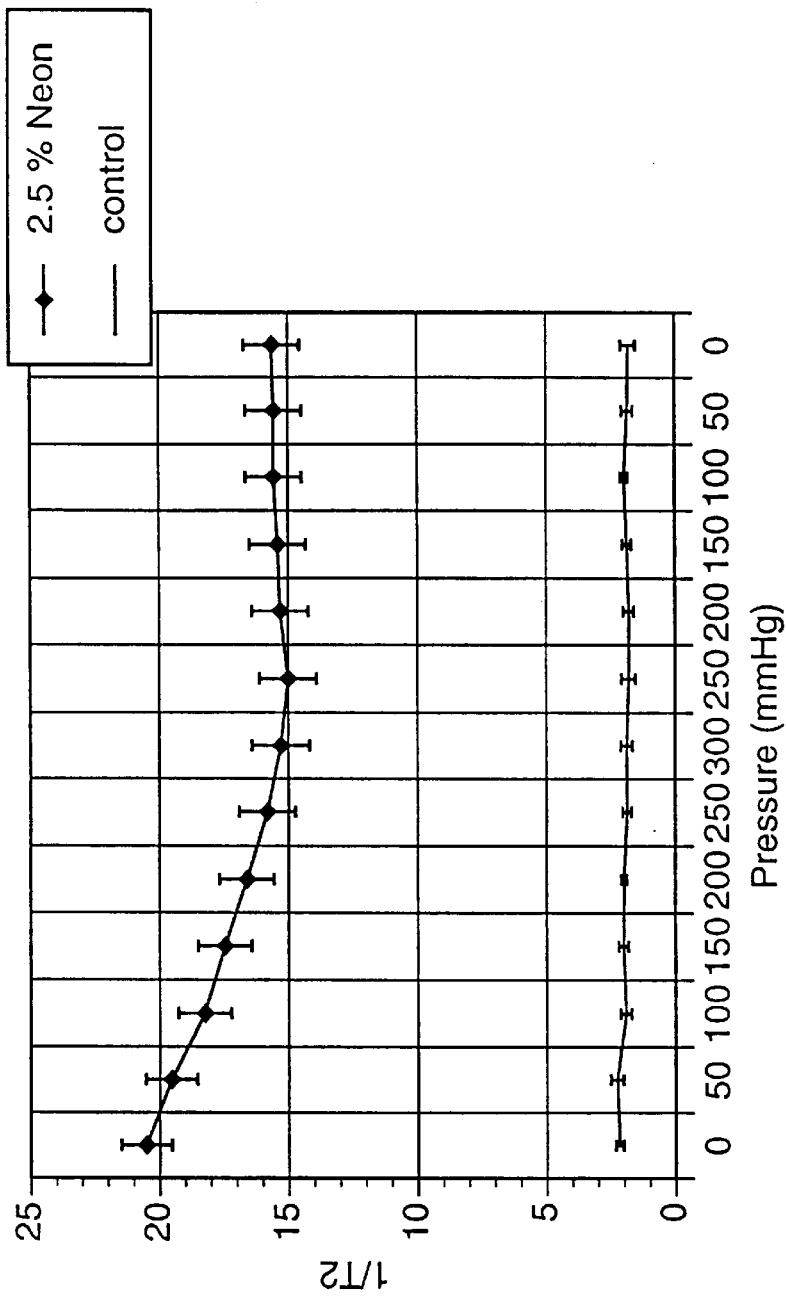
FIG. 7 is a graph showing the effect of pressure on 1/T2 (in seconds) of gas filled microspheres containing 2.5% by volume of neon, using ascending and decending pressures of 0, 50, 100, 150, 200, 250, and 300 mm Hg.
Figure 8:
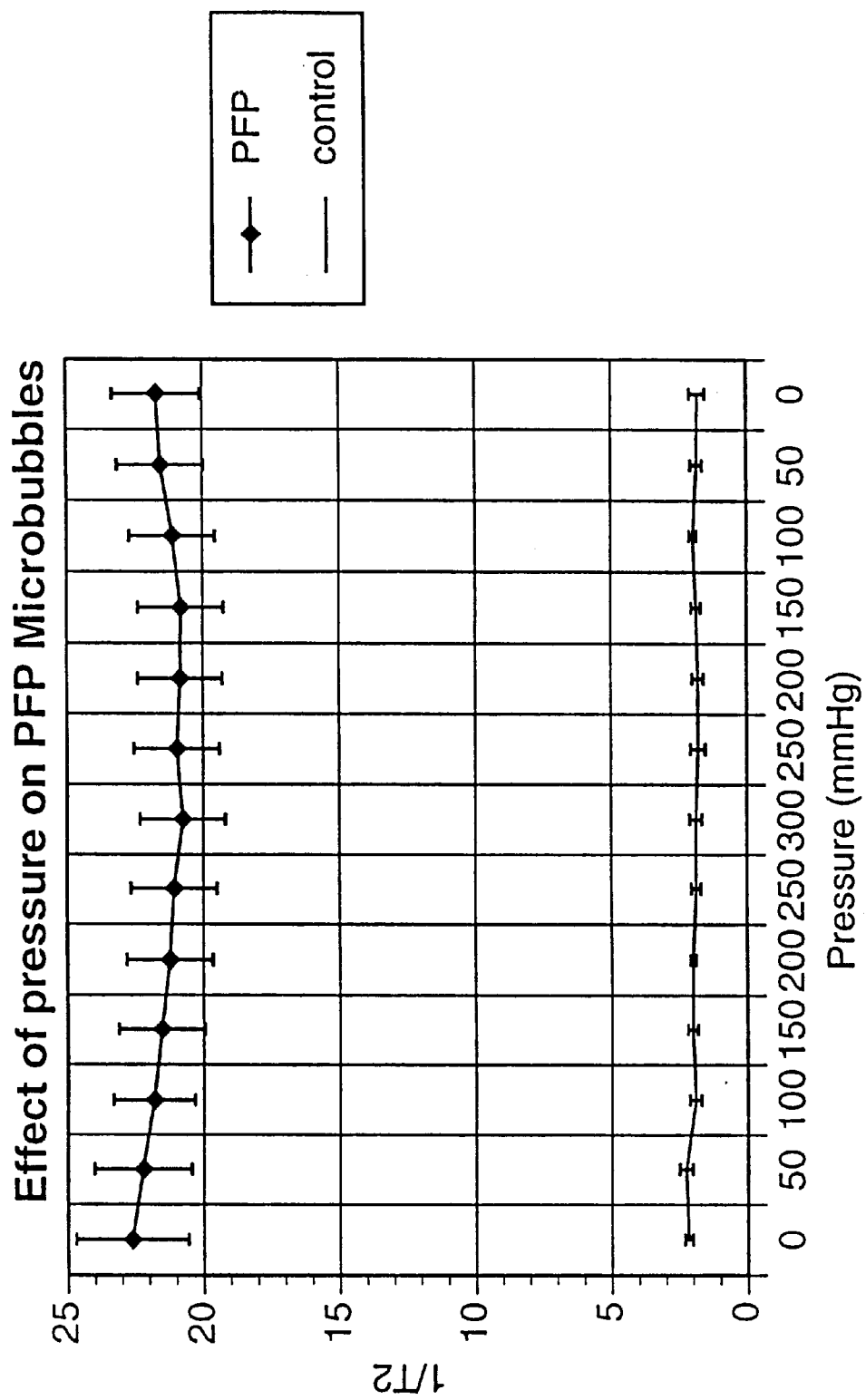
FIG. 8 is a graph showing the effect of pressure on 1/T2 (in seconds) of gas filled microspheres containing 2.5% by volume of perfluoropropane (PFP), using ascending and decending pressures of 0, 50, 100, 150, 200, 250, and 300 mm Hg.
Figure 9:
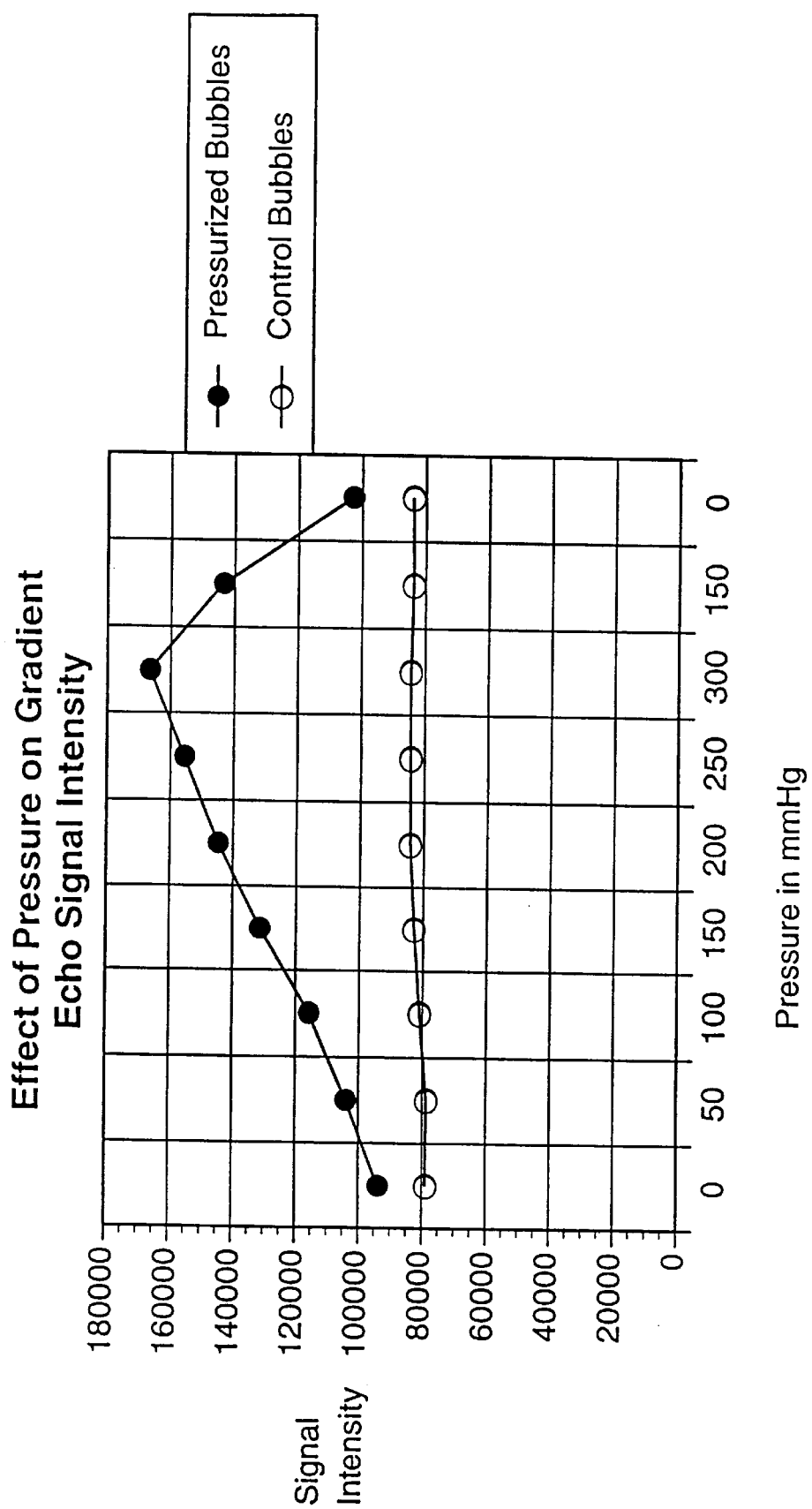
FIG. 9 is a graphical representation of the effect of pressure on signal intensity of a gradient echo pulse sequence using nitrogen gas filled microspheres, applying ascending and decending pressures of 0, 50, 100, 150, 200, 250, and 300 mm Hg.

Example 16
Effect of Pressure on MRI 1/T2 and Signal Intensity of Gas-Filled Liposomes The gas filled microspheres of Example 15 were scanned during exposure to pressures of 0, 50, 100, 150, 200, 250, and 300 mm of Hg. The results are shown in FIGS. 6–9. Specifically, FIG. 6 shows a diagram of the effect of pressure on gas-filled liposome size. FIG. 7 shows the effect on 1/T2 of 2.5% by volume neon and FIG. 8 shows the effect on 1/T2 of 2.5% by volume PFP upon exposure to pressure. FIG. 9 shows the effect on signal intensity in nitrogen gas-filled liposomes using a gradient echo pulse sequence upon exposure to pressure.

Example 17
Effect of Pressure on MRI 1/T2 and Signed Intensity of Gas-Filled Liposomes Ten cc of a suspension of gas-filled liposomes comprising of 20 mole % PFP, 70 mole % air and 10 mole % $^{17}O_2$ gas is injected into a patient with an aortic coarct. Gradient echo pulse sequences are performed by MRI and the signal intensities are measured as well as $1/T_2^*$ across the coarct. By looking at the increase in signal intensity or decrease in $1/T_2^*$ across the coarct a pressure gradient is estimated by magnetic resonance imaging.

The disclosures of each patent, patent application and publication cited or described in this document are hereby incorporated herein by reference, in their entirety.

Various modification of the invention, in addition to those described herein, will be apparent to those skilled in the art from the foregoing description. Such modifications are also intended to fall within the scope of the appended claims.

What is claimed is:

1. A method of providing an image of an internal region of a patient comprising (i) administering to the patient a gaseous precursor filled microsphere, wherein said microsphere contains substantially no sulfide linkages and consists essentially of one or more lipids, one or more lipids bearing polymers, or combinations thereof, (ii) allowing the gaseous precursor to undergo a phase transition from a liquid to a gas in the patient, and (iii) scanning the patient using magnetic resonance imaging to obtain visible images of said region.

2. A method for diagnosing the presence of a diseased tissue or region in a patient comprising (i) administering to the patient a gaseous precursor filled microsphere, wherein said microsphere contains substantially no sulfide linkages and consists essentially of one or more lipids, one or more lipids bearing polymers, or combinations thereof, (ii) allowing the gaseous precursor to undergo a phase transition from a liquid to a gas in the patient, and (iii) scanning the patient using magnetic resonance imaging to obtain visible images of any diseased tissue or region in the patient.

3. A method according to claim 1 or 2 wherein the region is the vasculature.

4. A method according to claim 1 or 2 wherein the region is the cardiovascular region.

5. A method according to claim 1 or 2 wherein the region is the gastrointestinal region.

6. A method according to claim 1 or 2 wherein the scanning is of the vasculature of the patient.

7. A method according to claim 1 or 2 wherein the scanning is of the cardiovascular region of the patient.

8. A method according to claim 1 or 2 wherein the scanning is of the gastrointestinal region of the patient.

9. A method according to claim 1 or 2 wherein the scanning is of a region of the patient selected from the following: intranasal tract; auditory canal; intraocular region; intraperitoneal region; kidneys; urethra; and genitourinary tract.

10. A method of claim 1 wherein said lipid is a phospholipid.

11. A method of claim 2 wherein said lipid is a phospholipid.

12. A method of claim 1 wherein said microsphere comprises a monolayer.

13. A method of claim 12 wherein said monolayer comprises a phospholipid.

14. A method of claim 2 wherein said microsphere comprises a monolayer.

15. A method of claim 14 wherein said monolayer comprises a phospholipid.

16. A method of claim 1 wherein said gaseous precursor is a perfluorocarbon.

17. A method of claim 11 wherein said gaseous precursor is selected from the group consisting of sulfur hexafluoride, perfluoromethane, perfluoroethane, perfluoropropane, perfluorocyclopropane, perfluorobutane, perfluorocyclobutane, perfluoropentane, perfluorocyclopentane, perfluorohexane, and perfluoroheptane.

18. A method of claim 17 wherein said gaseous precursor is perfluorohexane.

19. A method of claim 17 wherein said gaseous precursor is perfluoropropane.

20. A method of claim 17 wherein said gaseous precursor is selected from the group consisting of perfluoropentane, perfluorocyclopentane, perfluorohexane, and perfluoroheptane.

21. A method of claim 20 wherein said gaseous precursor is perfluoropentane.

22. A method of claim 1 wherein said microsphere is rehydrated from a lyophilized microsphere.

23. A method of claim 1 wherein said lipid microsphere comprises at least 70 mole percent of at least one lipid.

24. A method of claim 1 wherein said lipid microsphere comprises at least two lipids wherein said first lipid contains substantially no linkages to a polymer and comprises at least 70 mole percent of the total moles of the microsphere, and wherein said second lipid bears a hydrophilic polymer.

25. A method of claim 24 wherein said first lipid comprises: (i) a neutral lipid, and (ii) a negatively charged lipid, wherein the amount of said negatively charged lipid is greater than 1 mole percent of total lipids present.

26. A method of claim 25 wherein said negatively charged lipid is phosphatidic acid.

27. A method of claim 24 wherein the hydrophilic polymer of said second lipid is selected from the group consisting of polyethyleneglycol, polypropyleneglycol, polyvinylalcohol, and polyvinylpyrrolidone and copolymers thereof.

28. A method of claim 24 wherein the lipids comprise about 77.5 mole percent dipalmitoyl-phosphatidylcholine, about 12.5 mole percent of dipalmitoyl-phosphatidic-acid, and about 10 mole percent of dipalmitoylphosphatidylethanolamine-polyethyleneglycol 5000.

29. A method of claim 24 wherein the lipids comprise about 82 mole percent dipalmitoylphosphatidyl-choline, about 10 mole percent of dipalmitoylphosphatidic acid, and about 8 mole percent of dipalmitoylphosphatidyl-ethanolamine-polyethyleneglycol 5000.

30. A method of claim 2 wherein said gaseous precursor is a perfluorocarbon.

31. A method of claim 2 wherein said gaseous precursor is selected from the group consisting of sulfur hexafluoride, perfluoromethane, perfluoroethane, perfluoropropane, perfluorocyclopropane, perfluorobutane, perfluorocyclobutane, perfluoropentane, perfluorocyclopentane, perfluorohexane, and perfluoroheptane.

32. A method of claim 31 wherein said gaseous precursor is perfluorohexane.

33. A method of claim 31 wherein said gaseous precursor is perfluoropropane.

34. A method of claim 31 wherein said gaseous precursor is selected from the group consisting of perfluoropentane, perfluorocyclopentane, perfluorohexane, and perfluoroheptane.

35. A method of claim 31 wherein said gaseous precursor is perfluoropentane.

36. A method of claim 2 wherein said microsphere is rehydrated from a lyophilized microsphere.

37. A method of claim 2 wherein said lipid microsphere comprises at least 70 mole percent of at least one lipid.

38. A method of claim 2 wherein said lipid microsphere comprises at least two lipids wherein said first lipid contains substantially no linkages to a polymer and comprises at least 70 mole percent of the total moles of the microsphere, and wherein said second lipid bears a hydrophilic polymer.

39. A method of claim 38 wherein said first lipid comprises: (i) a neutral lipid, and (ii) a negatively charged lipid, wherein the amount of said negatively charged lipid is greater than 1 mole percent of total lipids present.

40. A method of claim 39 wherein said negatively charged lipid is phosphatidic acid.

41. A method of claim 38 wherein the hydrophilic polymer of said second lipid is selected from the group consisting of polyethyleneglycol, polypropyleneglycol, polyvinylalcohol, and polyvinylpyrrolidone and copolymers thereof.

42. A method of claim 38 wherein the lipids comprise about 77.5 mole percent dipalmitoyl-phosphatidylcholine, about 12.5 mole percent of dipalmitoyl-phosphatidic acid, and about 10 mole percent of dipalmitoylphosphatidylethanolamine-polyethyleneglycol 5000.

43. A method of claim 38 wherein the lipids comprise about 82 mole percent dipalmitoylphosphatidyl-choline, about 10 mole percent of dipalmitoylphosphatidic acid, and about 8 mole percent of dipalmitoylphosphatidyl-ethanolamine-polyethyleneglycol 5000.

* * * * *

UNITED STATES PATENT AND TRADEMARK OFFICE
CERTIFICATE OF CORRECTION

PATENT NO. : 5,922,304
DATED : July 13, 1999
INVENTOR(S) : Evan C. Unger

It is certified that error appears in the above-identified patent and that said Letters Patent is hereby corrected as shown below:

Title page,
[73] Assignee, please delete "Imarx" and insert -- ImaRx -- therefor.
[73] Assignee, please delete "Tucson, Ark". and insert -- Tucson, Ariz. -- therefor.
Under related U.S. Application Data, at [63], third line thereof, after "Jun. 11, 1993,", please insert -- Pat No. 5,580,575 --.
Under U.S. PATENT DOCUMENTS, second column, please delete "5,198,255" and insert -- 5,198,225 -- therefor.
Under U.S. PATENT DOCUMENTS, first column, please add the following references:

| | | | |
|---|---|---|---|
| -- 4,834,964 | 5/1989 | Rosen | 424/9 |
| 4,984,573 | 1/1991 | Leunbach | 128/653 |
| 5,362,477 | 11/1994 | Moore et al. | 424/9 |
| 5,485,839 | 1/1996 | Aida et al. | 128/653.1 |
| 5,339,814 | 8/1994 | Lasker | 128/653.4 |
| 5,545,396 | 8/1996 | Albert et al. | 424/93 |
| 5,593,680 | 1/1997 | Bara et al. | 424/401 |
| 5,686,102 | 11/1997 | Gross et al. | 424/450 |
| 5,716,597 | 2/1998 | Lohrmann et al. | 424/9.5 |
| 5,732,707 | 3/1998 | Widder et al. | 128/661.08 |
| 3,291,843 | 12/1996 | Fritz et al. | 260/614 |
| 3,557,294 | 1/1971 | Dear et al. | 424/342 |
| 4,427,649 | 1/1984 | Dingle et al. | 424/38 |
| 4,663,161 | 5,1987 | Mannino et al. | 424/89 |
| 4,918,065 | 4/1990 | Stindl et al. | 514/179 |
| 5,008,109 | 4/1991 | Tin | 424/422 |
| 5,107,842 | 4/1992 | Levene et al. | 128/662.02 |
| 5,196,348 | 3/1993 | Schweighardt et al. | 436/173 |
| 5,339,814 | 8/1994 | Lasker | 128/653.4 |
| 5,552,155 | 9/1996 | Bailey et al. | 424/450 |
| 5,679,459 | 10/1997 | Riess et al. | 428/402.2 |
| 5,711,933 | 1/1998 | Bichon et al. | 424/9.52 |
| 5,733,527 | 3/1998 | Schutt | 424/9.52 |
| 4,693,999 | 9/1987 | Axelsson et al. | 514/174 |
| 5,740,807 | 4/1998 | Porter | 128/662.02 |
| 5,569,448 | 10/1996 | Wong et al. | 424/9.45 |
| 5,804,162 | 9/1998 | Kabalnov et al. | 424/9.51 |

UNITED STATES PATENT AND TRADEMARK OFFICE
CERTIFICATE OF CORRECTION

PATENT NO. : 5,922,304  
DATED : July 13, 1999  
INVENTOR(S) : Evan C. Unger

Page 2 of 6

It is certified that error appears in the above-identified patent and that said Letters Patent is hereby corrected as shown below:

4,919,895    4/1990    Heldebrant et al.    422/129 --

Under FOREIGN PATENT DOCUMENTS, first column, please delete "72 255 A2" and insert -- 727 255 A2 -- therefor.

Under FOREIGN PATENT DOCUMENTS, second column, please add the following references:

| | | |
|---|---|---|
| -- WO 92/22298 | 12/1992 | WIPO |
| WO 94/00110 | 1/1994 | WIPO |
| WO 94/28873 | 12/1994 | WIPO |
| WO 98/00172 | 1/1998 | WIPO |
| WO 84/02909 | 8/1984 | WIPO |
| WO 92/15284 | 9/1972 | WIPO |
| WO 92/22249 | 12/1992 | WIPO |
| WO 95/24184 | 9/1995 | WIPO |
| WO 96/40281 | 12/1996 | WIPO |
| 2 700 952 | 8/1994 | France |
| 25 21 003 | 8/1976 | Germany |
| 0 614 656 A1 | 9/1994 | European Pat. Off. |
| 0 052 575 | 5/1982 | European Pat. Off. -- |

Under OTHER PUBLICATIONS, second column, at Shiina et al., please delete "Hyperthermiaby" and insert -- Hyperthermia by -- therefor.

Under OTHER PUBLICATIONS, second column, at Poznansky et al., please delete "Biologica" and insert -- Biological -- therefor.

Under OTHER PUBLICATIONS, second column, at Villanueva et al., please delete "Patters" and insert" -- Patterns -- therefor.

Under OTHER PUBLICATIONS, second column, please add the following references:

-- Fitzpatrick, et al., "Metal Ion Catalyzed Decarboxylation: Kinetics and Mechanism of the Oxidative Decarboxylation of Copper (II) Complexes of Aminomalonic Acid in Aqueous Solution", *Inorganic Chemistry*, Vol. 13, No. 3, pp. 568-574 (1974)

Thanassi, "Aminomalonic Acid: Spontaneous Decarboxylation and Reaction with 5-Deoxypyridoxal", *Biochemistry*, Vol 9, No. 3, pp. 525-532 (1970)

Stelmashok et al., *Koordinatsionnaya Khimiya*, Vol. 3, No. 4, pp. 524-527 (1977) (Russian and English language versions)

Mayhew et al., "High-Pressure Continuous-Flow System for Drug Entrapment in Liposomes", *Methods in Enzymology*, Vol. 149, pp. 64-77 (1987)

UNITED STATES PATENT AND TRADEMARK OFFICE
CERTIFICATE OF CORRECTION

PATENT NO.   : 5,922,304
DATED        : July 13, 1999
INVENTOR(S)  : Evan C. Unger It is certified that error appears in the above-identified patent and that said Letters Patent is hereby corrected as shown below:

Mayhew et al, "Characterization of Liposomes Prepared Using a Microemulsifier", *Biochimica et Biophysica Acta,*, Vol. 775, pp. 169-174 (1984)

Hope et al., "Production of large unilamellar vesicles by a rapid extrusion procedure. Characterization of size distribution, trapped volume, and ability to maintain a membrane potential", *Biochimica et Biophysica Acta*, Vol. 812, pp. 55-65 (1985)

Mayer et al., "Vesicles of Variable Size Produced by a Rapid Extrusion Procedure", *Biochimica et Biophysica Acta*, Vol. 858, pp. 161-168 (1986)

Cheng et al., "The Production and Evaluation of Contrast-Carrying Liposomes Made with an Automatic High Pressure System", *Investigative Radiology*, Vol. 22, No. 1, pp. 47-55 (1987)

Jain, et al., "Facilitated Transport", *Introduction to Biological Membranes*, Ch. 9, pp. 192-231 (J. Wiley and Sons, N.Y. 1980)

Nomura et al., "US Contrast Enhancement of Hepatic Tumor with Helium Gas Microbubbles: A Preliminary Report", *Jpn. J. Med. Ultrasonics*, Vol. 18, No. 5 (1991) (Japanese with English language abstract)

Lindner et al., "Myocardial Perfusion Characteristics and Hemodynamic Profile of MRX-115, a Venous Echocardiographic Contrast Agent, During Acute Myocardial Infraction,"*J. Am. Soc. of Echocardiography*, Vol. 11, No. 1, pp. 36-46 (1998)

Regen et al., "Polymerized Phosphatidylcholine Vesicles. Synthesis and Characterization,"*J. Am. Chem. Soc.*, Vol. 104, No. 3, pp. 191-195 (1982)

Wei et al., "Quantification of Myocardial Blood Flow With Ultrasound-Induced Destruction of Microbubbles Administered as a Constant Venous Infusion," *Circulation,*    Vol. 97, pp. 473-483 (1998)

Hynynen et al., "The Usefulness of a Contrast Agent and Gradient-Recalled Acquisition in a Steady-State Imaging Sequence for Magnetic Resonance Imaging-Guided Noninvasive Ultrasound Surgery," *Investigative Radiology*, Vol. 29, pp. 897-903 (Oct. 1994) --

UNITED STATES PATENT AND TRADEMARK OFFICE
CERTIFICATE OF CORRECTION

PATENT NO. : 5,922,304
DATED : July 13, 1999
INVENTOR(S) : Evan C. Unger

It is certified that error appears in the above-identified patent and that said Letters Patent is hereby corrected as shown below:

Column 2,
Line 4, after "Apr. 10, 1999," please add -- now abandoned, --.
Line 5, please delete "moire" and insert -- more -- therefor.

Column 5,
Line 34, delete "gasesous" and insert -- gaseous -- therefor.

Column 6,
Line 50, please delete "decending" and insert -- descending -- therefor.
Line 55, please delete "decending" and insert -- descending -- therefor.
Line 60, please delete "decending" and insert -- descending -- therefor.

Column 7,
Line 61, please delete "invention Such" and insert -- invention. Such -- therefor.

Column 8,
Line 3, please delete " 'IQ' " and insert -- "Q" -- therefor.

Column 9,
Line 20, please delete the second occurrence of "fluorinated".
Line 33, please delete "gasesous" and insert -- gaseous -- therefor.
Line 57, please delete the second occurrence of "that", at the end of the line,
and insert -- than -- therefor.

Column 13,
Line 13, please delete " 'ahead' " and insert -- "head" -- therefor.
Line 48, please delete "3phosphocholines" and insert -- 3-phosphocholines -- therefor.

Column 15,
Line 23, please delete "glucuroneide" and insert -- glucuronide -- therefor.
Line 54, please delete "trimethylammoium" and insert -- trimethylammonium --
therefor.

Column 22,
Line 30, please delete "R1 nd R2" and insert -- R1 and R2 -- therefor.

UNITED STATES PATENT AND TRADEMARK OFFICE
CERTIFICATE OF CORRECTION

PATENT NO. : 5,922,304
DATED : July 13, 1999
INVENTOR(S) : Evan C. Unger

Page 5 of 6

It is certified that error appears in the above-identified patent and that said Letters Patent is hereby corrected as shown below:

Column 23,
Lines 15-16, please delete the formula

"$1/T_1M = (2/15)\ S(S+1)\ y^2g^2\beta^2/r^6[3T_c/(1+\omega_1^{2+sc}T_c^2) + 7T_c/(1+\omega_s^{2+sc}T_c^2)] + (2/3)\ S(S+1)A^2/h^2\ [T_c/(1+\omega_s2T_c^2)]$"

and insert the formula

-- $1/T_1M = (2/15)\ S(S+1)\ y^2g^2\beta^2/r^6\ [\ 3T_c/(1+\omega_1^2T_c^2) + 7T_c/(1+\omega_s^2T_c^2)\ ] + (2/3)\ S(S+1)A^2/h^2\ [T_c/(1+\omega_s2T_c^2)]$ -- therefor.

Lines 20-21, please delete the formula

"$1/T_2M = (1/15)\ S(S+1)\ y^2g^2\beta^2/r^6[4T_c + 3T_c/(1+\omega_1^{2+sc}T_c^2) + 13T_c/(1+w_s^{2+sc}T_c^2)] + (1/3)\ S(S+1)A^2/h^2\ [T_c/(1+\omega_s2T_c^2)]$"

and insert the formula

-- $1/T_2M = (1/15)\ S(S+1)\ y^2g^2\beta^2/r^6[\ 4T_C + 3T_c/(1+\omega_1^2T_c^2) + 13T_c/(1+w_s^2T_c^2)] + (1/3)\ S(S+1)A^2/h^2\ [T_c/(1+\omega_s2T_c^2)]$ -- therefor.

Column 24,
Line 60, please delete "patient Thus" and insert -- patient. Thus -- therefor.

Column 26,
Line 12, please delete "dipalimitoyl" and insert -- dipalmitoyl -- therefor.

Column 34,
Line 67, please delete "dipalimitoylphosphatidylcholine" and insert
-- dipalmitoylphosphatidylcholine -- therefor.

Column 36,
Line 44, please delete "Cardiovacular" and insert -- Cardiovascular -- therefor.

Column 38,
Line 52, please delete "micropheres" and insert -- microspheres -- therefor.

UNITED STATES PATENT AND TRADEMARK OFFICE
CERTIFICATE OF CORRECTION

PATENT NO. : 5,922,304
DATED : July 13, 1999
INVENTOR(S) : Evan C. Unger

It is certified that error appears in the above-identified patent and that said Letters Patent is hereby corrected as shown below:

Column 43,
Line 2, please delete "Gasseous" and insert -- Gaseous -- therefor.
Line 27, please delete "propyleneglycole" and insert -- propyleneglycol -- therefor.

Column 45,
Line 61, Claim 17, please delete "claim 11" and insert -- claim 1 -- therefor.

Signed and Sealed this

Twenty-seventh Day of November, 2001

Attest: